US012751671B2

(12) United States Patent
Sipe et al.

(10) Patent No.: US 12,751,671 B2
(45) Date of Patent: Oct. 6, 2026

(54) SYSTEMS AND METHODS FOR CLASSIFYING MOTION OF A PATIENT WEARING AN AMBULATORY MEDICAL DEVICE

(71) Applicant: ZOLL MEDICAL CORPORATION, Chelmsford, MA (US)

(72) Inventors: Michael A. Sipe, Pittsburgh, PA (US); Steven J. Szymkiewicz, Bethel Park, PA (US); Shane S. Volpe, Saltsburg, PA (US); Gary A. Freeman, Waltham, MA (US)

(73) Assignee: ZOLL Mecial Corporation, Chelmsford, MA (US)

( * ) Notice: Subject to any disclaimer, the term of this patent is extended or adjusted under 35 U.S.C. 154(b) by 610 days.

(21) Appl. No.: 17/907,223

(22) PCT Filed: Mar. 19, 2021

(86) PCT No.: PCT/US2021/023248
§ 371 (c)(1),
(2) Date: Sep. 23, 2022

(87) PCT Pub. No.: WO2021/194888
PCT Pub. Date: Sep. 30, 2021

(65) Prior Publication Data
US 2023/0109648 A1 Apr. 6, 2023

Related U.S. Application Data
(60) Provisional application No. 62/993,841, filed on Mar. 24, 2020.

(51) Int. Cl.
*A61B 5/00* (2006.01)
*A61B 5/332* (2021.01)
(Continued)

(52) U.S. Cl.
CPC .............. *A61B 5/721* (2013.01); *A61B 5/332* (2021.01); *A61B 5/352* (2021.01); *A61N 1/3625* (2013.01);
(Continued)

(58) Field of Classification Search
CPC ......... A61B 5/721; A61B 5/332; A61B 5/352; A61B 2562/0219; A61N 1/3625; A61N 1/3925; A61N 1/3987; A61N 1/0484
See application file for complete search history.

(56) References Cited

U.S. PATENT DOCUMENTS 4,576,170 A 3/1986 Bradley et al.
4,580,572 A 4/1986 Granek
(Continued)

OTHER PUBLICATIONS

Twomey et al. " A Comprehensive Study of Activity Recognition Using Accelerometers" Informatics 5, 27 (2018) 37 pages.
(Continued)

*Primary Examiner* — Benjamin J Klein
*Assistant Examiner* — Thien Jason Tran
(74) *Attorney, Agent, or Firm* — Secant IP, P.L.L.C.

(57) ABSTRACT

A wearable medical device is provided. The device includes electrodes to receive electrical signals from a patient, monitor for a cardiac arrhythmia, and provide a therapeutic shock to the patient in response to detecting the arrhythmia. The device includes a user interface to receive patient input indicating initiation or termination of a high-noise activity. The device can include accelerometers to generate motion signals. The device includes a processor to monitor for initiation or termination of the high-noise activity based on a noise level in the electrical signals, the motion signals, and the patient input. The processor can cause, in response to the initiation of the high-noise activity, an arrhythmia detection process to execute in an activity-induced noise (AIN) robust mode, and cause, in response to the termination of the
(Continued)

high-noise activity, the arrhythmia detection process to execute in an AIN sensitive mode.

24 Claims, 31 Drawing Sheets

(51) Int. Cl.

| | |
|---|---|
| ***A61B 5/352*** | (2021.01) |
| ***A61N 1/04*** | (2006.01) |
| ***A61N 1/362*** | (2006.01) |
| ***A61N 1/39*** | (2006.01) |

(52) U.S. Cl.

CPC ......... *A61N 1/3925* (2013.01); *A61N 1/3987* (2013.01); *A61B 2562/0219* (2013.01); *A61N 1/0484* (2013.01)

(56) References Cited

U.S. PATENT DOCUMENTS

| | | | |
|---|---|---|---|
| 4,928,690 A | 5/1990 | Heilman | |
| 5,741,306 A | 4/1998 | Glegyak | |
| 5,944,669 A | 8/1999 | Kaib | |
| 6,065,154 A | 5/2000 | Hulings et al. | |
| 6,374,138 B1 | 4/2002 | Owen et al. | |
| 6,681,003 B2 | 1/2004 | Linder et al. | |
| 8,140,154 B2 | 3/2012 | Donnelly et al. | |
| 8,406,842 B2 | 3/2013 | Kaib et al. | |
| 11,246,538 B2 | 2/2022 | Mitchell | |
| 2010/0312131 A1* | 12/2010 | Naware | A61B 5/412 600/518 |
| 2015/0050972 A1 | 2/2015 | Sarrafzadeh et al. | |
| 2016/0074667 A1 | 3/2016 | Sullivan | |
| 2017/0087371 A1* | 3/2017 | Freeman | A61N 1/3625 |
| 2017/0196497 A1 | 7/2017 | Ray et al. | |
| 2018/0160912 A1* | 6/2018 | Martin | G16H 40/63 |
| 2019/0143133 A9 | 5/2019 | Foshee, Jr. | |

OTHER PUBLICATIONS

Ravi et al. "Activity Recognition from Accelerometer Data" AAAI. 3. 1541-1546 (2005).

Cahalin et al. "Heart rate recovery after the 6 min walk test rather than distance ambulated is a powerful prognostic indicator in heart failure with reduced and preserved ejection fraction: a comparison with cardiopulmonary exercise testing" European Journal of Heart Failure (2013) 15, 519-527.

International Search Report and Written Opinion for PCT Application No. PCT/US2021/023248 Date of Mailing: Jun. 22, 2021 (16 pages).

* cited by examiner

SYSTEMS AND METHODS FOR CLASSIFYING MOTION OF A PATIENT WEARING AN AMBULATORY MEDICAL DEVICE

CROSS-REFERENCE TO RELATED APPLICATIONS

This application claims priority under 35 U.S.C. § 120 as a national stage application of PCT Application No. PCT/GR2021/194888, titled "SYSTEM AND METHOD FOR CLASSIFYING MOTION OF A PATIENT WEARING AN AMBULATORY MEDICAL DEVICE" and filed Jun. 30, 2022, which claims priority under 35 U.S.C. § 119(e) to U.S. Provisional Application No. 62/993,841 titled "Systems and Methods for Classifying Motion of a Patient Wearing an Ambulatory Medical Device," filed Mar. 24, 2020, each of which is hereby incorporated herein by reference in its entirety.

BACKGROUND

The present disclosure is directed to classifying the motion of a patient wearing an ambulatory medical device and determining the impact of that motion on cardiac monitoring signals for the patient.

Heart failure, if left untreated, can lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for the support of life. It is generally useful to monitor heart failure patients to assess heart failure symptoms early and provide interventional therapies as soon as possible.

Patients who are at risk, have been hospitalized for, or otherwise are suffering from, adverse heart conditions can be prescribed a wearable cardiac monitoring and/or treatment device. In addition to the wearable device, the patient can also be given a battery charger and a set of rechargeable batteries. As the wearable device is generally prescribed for continuous or near-continuous use (e.g., only to be removed when bathing), the patient wears the device during all daily activities such as walking, sitting, climbing stairs, resting or sleeping, and other similar daily activities. During these activities one or more components of the wearable device can shift position or otherwise move that can cause noise or otherwise disrupt cardiac monitoring signals being measured and analyzed by the wearable device. It is therefore advantageous to determine a type of motion and determine what actions, if any, may be taken to address the noise or disruption based on the motion type.

SUMMARY

In an example, a wearable cardioverter/defibrillator apparatus for monitoring arrhythmias during different types of patient activities is provided. The apparatus includes a memory configured to store an arrhythmia detection process configurable to execute in one of an activity-induced noise (AIN) sensitive mode and an AIN robust mode, a user interface configured to receive patient input, one or more accelerometers configured to generate a plurality of motion signals representative of movement of a patient, and at least one processor coupled to the memory and the one or more accelerometers. The at least one processor is configured to: cause the arrhythmia detection process to execute in the AIN sensitive mode, determine initiation of a high-noise activity based on at least one of a) the plurality of motion signals and b) the patient input via the user interface, cause, in response to determining the initiation of the high-noise activity, the arrhythmia detection process to execute in the AIN robust mode, determine a termination of the high-noise activity, and cause, in response to determining the termination of the high-noise activity, the arrhythmia detection process to execute in the AIN sensitive mode.

Implementations of the wearable cardioverter/defibrillator apparatus can include one or more of the following features.

In the apparatus, the at least one processor can further be configured to determine the termination of the high-noise activity based on a predetermined time out condition occurring after a predetermined time period. In some examples, the predetermined time period includes at least one of thirty seconds, one minute, two minutes, five minutes, ten minutes, fifteen minutes, twenty minutes, and thirty minutes. In some additional examples, the at least one processor is configured to, when the predetermined time out condition occurs, prompt the patient to indicate whether the high-noise activity has terminated. In some examples, the at least one processor is configured to suspend determination of the termination of the high-noise activity for a second predetermined time period if the patient indicates that the high-noise activity has not terminated. In some additional examples, the second predetermined time period can include at least one of thirty seconds, one minute, two minutes, five minutes, ten minutes, fifteen minutes, twenty minutes, and thirty minutes.

In the apparatus, the at least one processor can be configured to determine the termination of the high-noise activity based on the patient input via the user interface.

In the apparatus, the at least one processor can be configured to determine termination of the high-noise activity based on the plurality of motion signals.

In the apparatus, the at least one processor can be configured to determine the initiation of a high-noise activity based upon the plurality of motion signals at least by determining the patient is performing one of a walking activity and a running activity.

In the apparatus, the at least one processor can be configured to determine that the patient is performing one of a walking activity and a running activity based on a classification of the plurality of motion signals using an artificial neural network based motion classifier.

In examples, the apparatus can further include one or more sensing electrodes configured to sense one or more electrical signals that are indicative of cardiac activity of the patient. In some examples, the processor can be further configured to receive the one or more electrical signals from the one or more sensing electrodes, determine electrocardiogram (ECG) data for the patient based upon the one or more electrical signals, determine what portion of the ECG data is noisy ECG data caused by patient activity, and determine the patient activity is a high-noise activity if the portion of ECG data that is noisy ECG data exceeds a predetermined noise threshold. In some examples, the predetermined noise threshold can include at least one of a detected ECG noise peak more than 25% greater than a calculated R-wave mean value, a detected noise peak more than 50% greater than a calculated R-wave mean value, and a detected noise peak more than 100% greater than a calculated R-wave mean value. In some additional examples, the predetermined noise threshold can include a threshold number of ECG noise peaks that are more than 25% greater than a calculated R-wave mean value in a predetermined period of time. In some examples, the threshold number of ECG noise peaks can include at least one of 3 peaks, 5 peaks, 10 peaks, and 15 ECG noise peaks. In some additional examples, the predetermined period of time can include at least one of 30 seconds, 45 seconds, 60 seconds, 75 seconds, 90 seconds, 3 minutes, 5 minutes, 10 minutes, 15 minutes, and 30 minutes. In some additional examples, the portion of the ECG data is transformed in a frequency domain, and wherein the predetermined noise threshold can include a dominant frequency of at least one of less than 1 Hz and in excess of 20 Hz.

In the apparatus, executing in the AIN sensitive mode can include monitoring a set of ECG metrics for the patient, the set of ECG metrics including at least two or more of heart rate, heart rate variability, premature ventricular contraction burden or counts, atrial fibrillation burden, pauses, heart rate turbulence, QRS height, QRS width, changes in ECG morphology, cosine R-T, QT interval, QT variability, T-wave width, T-wave alternans, T-wave amplitude, T-wave variability, R-wave amplitude, and ST segment changes. In some examples, executing in the AIN robust mode can include monitoring the patient for changes in one or more metrics in a subset of the set of ECG metrics for the patient. In some additional examples, the subset of the set of ECG metrics for the patient can include at least one of heart rate, QRS width, R-wave amplitude, and T-wave amplitude.

In another example, a second wearable cardioverter/defibrillator apparatus for monitoring arrhythmias during different types of patient activities is provided. The apparatus includes a memory storing an arrhythmia detection process configurable to execute in one of an AIN sensitive mode and an AIN robust mode, one or more accelerometers configured to generate a plurality of motion signals representative of movement of a patient, and at least one processor coupled to the memory and the one or more accelerometers. The at least one processor is configured to cause the arrhythmia detection process to execute in the AIN sensitive mode, analyze the plurality of motion signals to determine whether the patient is walking or running, cause, in response to determining that the patient is walking or running, the arrhythmia detection process to execute in the AIN robust mode, detect a life-threatening condition in the patient in response to the heart rate transgressing a predetermined heart rate threshold using the arrhythmia detection process executing in the AIN robust mode, provide a notification to the patient indicating that the patient should stop walking or running in response to detecting the life-threatening condition, confirm the life-threatening condition in the patient using the arrhythmia detection process executing in the AIN sensitive mode, and initiate a treatment to the patient on confirming the life-threatening condition in the patient.

Implementations of the second wearable cardioverter/defibrillator apparatus for monitoring arrhythmias during different types of patient activities can include one or more of the following features.

In the apparatus, the at least one processor can be configured to analyze the plurality of motion signals to determine if at least a portion of the plurality of motion signals exceed a motion threshold and to generate a motion classification based on the determination that at least a portion of the plurality of motion signals exceed the motion threshold. In some examples, the motion threshold can include a change in signal amplitude on at least one directional axis of the plurality of motion signals that exceeds 50% over a period of time, a change in signal on at least one directional axis of the plurality of motion signals that exceeds 100% over a period of time, and a change in signal on at least one directional axis of the plurality of motion signals that exceeds 150% over a period of time.

In the apparatus, the predetermined heart rate threshold can include at least one of 100 bpm, 110 bpm, 120 bpm, 130 bpm, 140 bpm, and 150 bpm.

In the apparatus, the at least one processor can further be configured to determine that the patient has terminated the walking or running. In some examples, the at least one processor can further be configured to determine that the patient has terminated walking or running based upon expiration of a predetermined time period. In some additional examples, the predetermined time period can include at least one of thirty seconds, one minute, two minutes, five minutes, ten minutes, fifteen minutes, twenty minutes, and thirty minutes. In some examples, the at least one processor can be configured to suspend confirming the life-threatening condition in the patient for a second predetermined time period if the patient indicates that the walking or running has not terminated. In some additional examples, the second predetermined time period can include at least one of thirty seconds, one minute, two minutes, five minutes, ten minutes, fifteen minutes, twenty minutes, and thirty minutes.

In another example, a wearable cardioverter/defibrillator apparatus for providing adaptive noise notifications based upon motion classification is provided. The apparatus includes a plurality of electrodes configured to monitor and treat a patient having a cardiac arrhythmia, one or more accelerometers configured to generate a plurality of motion signals of the patient, a memory including a motion classifier, the motion classifier being trained on motion signals annotated with motion classifications, and at least one processor operationally coupled to the plurality of electrodes, the one or more accelerometers, and the memory. The at least one processor is configured to extract one or more features relating to a current state or activity of the patient based on the plurality of motion signals, store in the memory a feature vector including the extracted one or more features, classify the plurality of motion signals by applying the motion classifier to the stored feature vector to generate a classification, and provide, based on the classification, an indication of whether the plurality of motion signals are indicative of at least one of the patient walking, the patient running, and the patient climbing stairs.

Implementations of the wearable cardioverter/defibrillator apparatus for providing adaptive noise notifications based upon motion classification can include one or more of the following features.

In the apparatus, the at least one processor can further be configured to suspend providing an arrhythmia alert to the patient for a first predetermined period of time if the patient is classified as walking during detection of an arrhythmia condition. In examples, the predetermined time period can include at least one of thirty seconds, one minute, two minutes, five minutes, ten minutes, fifteen minutes, twenty minutes, and thirty minutes.

In the apparatus, the plurality of electrodes can include one or more sensing electrodes configured to acquire ECG signals from the patient and the at least one processor is further configured to suspend providing an arrhythmia alert to the patient for a first predetermined period of time if the patient is classified as walking during detection of an arrhythmia condition and the ECG signals are noisy.

In the apparatus, the at least one processor can be configured to suspend providing a noise alert to the patient if the patient is classified as walking during detection of an arrhythmia condition.

In the apparatus, the at least one processor can be configured to provide a notification to the patient to stop any motion during recording of ECG information for the patient.

In the apparatus, extracting the one or more features can include calculating one or more of an entropy of the plurality of motion signals, a mean of the plurality of motion signals, a standard deviation of the plurality of motion signals, energy within one or more frequency bands of the plurality of motion signals, one or more wavelet coefficients of the plurality of motion signals, one or more correlations between directional components within the plurality of motion signals, angles between consecutive motion signals of the plurality of motion signals, jerk of the plurality of motion signals, and slippage of the plurality of motion signals.

In the apparatus, the classification can include confidence metrics indicative of whether the patient is walking, the patient is running, and the patient is climbing stairs.

In the apparatus, the at least one processor can be configured to provide an arrhythmia alert responsive to detection of an arrhythmia condition, receive input indicating the arrhythmia alert was a false alert, and prompt the patient to indicate an activity being performed by the patient during the arrhythmia alert.

In another example, a wearable medical device for monitoring arrhythmias during patient activity is provided. The device includes a plurality of electrodes configured to monitor for a cardiac arrhythmia and provide a therapeutic shock to a patient in response to detecting the cardiac arrhythmia, a user interface configured to receive patient input indicating one of initiation or termination of a high-noise activity, one or more accelerometers configured to generate a plurality of motion signals representative of movement of a patient indicative of whether the patient is engaged in the high-noise-activity, and at least one processor coupled to the memory and the one or more accelerometers. The at least one processor is configured to monitor for initiation or termination of the high-noise activity based on at least one of a) the plurality of motion signals and b) the patient input via the user interface indicating the initiation or termination of the high-noise activity, cause, in response to the initiation of the high-noise activity, the arrhythmia detection process to execute in the AIN robust mode, and cause, in response to the termination of the high-noise activity, the arrhythmia detection process to execute in the AIN sensitive mode.

Implementations of the wearable medical device for monitoring arrhythmias during patient activity can include one or more of the following features.

In the device, the at least one processor can be configured to determine the termination of the high-noise activity based on a predetermined time out condition occurring after a predetermined time period. In some examples, the predetermined time period can include at least one of thirty seconds, one minute, two minutes, five minutes, ten minutes, fifteen minutes, twenty minutes, and thirty minutes. In some additional examples, the at least one processor can be configured to, when the predetermined time out condition occurs, prompt the patient to indicate whether the high-noise activity has terminated. In some examples, the at least one processor can be configured to suspend determination of the termination of the high-noise activity for a second predetermined time period if the patient indicates that the high-noise activity has not terminated. In some additional examples, the second predetermined time period can include at least one of thirty seconds, one minute, two minutes, five minutes, ten minutes, fifteen minutes, twenty minutes, and thirty minutes.

In the device, the at least one processor can be configured to determine the termination of the high-noise activity based on the patient input via the user interface.

In the device, the at least one processor can be configured to determine termination of the high-noise activity based on the plurality of motion signals.

In the device, the at least one processor can be configured to determine the initiation of the high-noise activity based upon the plurality of motion signals at least by determining the patient is performing one of a walking activity and a running activity.

In the device, the at least one processor can be configured to determine that the patient is performing one of a walking activity and a running activity based on a classification of the plurality of motion signals using an artificial neural network based motion classifier.

In some examples, the device can further include one or more sensing electrodes configured to sense one or more electrical signals that are indicative of cardiac activity of the patient. In some examples, the processor can be further configured to receive the one or more electrical signals from the one or more sensing electrodes, determine ECG data for the patient based upon the one or more electrical signals, determine what portion of the ECG data is noisy ECG data caused by patient activity, and determine the patient activity is a high-noise activity if the portion of ECG data that is noisy ECG data exceeds a predetermined noise threshold. In some additional examples, the predetermined noise threshold can include at least one of a detected ECG noise peak more than 25% greater than a calculated R-wave mean value, a detected noise peak more than 50% greater than a calculated R-wave mean value, or a detected noise peak more than 100% greater than a calculated R-wave mean value. In some examples, the predetermined noise threshold can include a threshold number of ECG noise peaks that are more than 25% greater than a calculated R-wave mean value in a predetermined period of time. In some additional examples, the threshold number of ECG noise peaks can include at least one of 3 peaks, 5 peaks, 10 peaks, and 15 ECG noise peaks. In some examples, the predetermined period of time can include at least one of 30 seconds, 45 seconds, 60 seconds, 75 seconds, 90 seconds, 3 minutes, 5 minutes, 10 minutes, 15 minutes, and 30 minutes. In some examples, the portion of the ECG data can be transformed in a frequency domain, and wherein the predetermined noise threshold includes a dominant frequency of at least one of less than 1 Hz and in excess of 20 Hz.

In another example, a second wearable medical device for monitoring arrhythmias during patient activity is provided. The device includes a plurality of ECG sensing electrodes configured to monitor one or more electrical signals from a patient, a plurality of therapy electrodes configured to provide a therapeutic shock to the patient in response to detecting the cardiac arrhythmia, a user interface configured to receive patient input indicating one of initiation or termination of a high-noise activity, and at least one processor coupled to the memory and the one or more accelerometers. The at least one processor is configured to monitor for indication of initiation or termination of the high-noise activity based on at least one of a) a noise level in the one or more electrical signals from the patient transgressing a predetermined noise threshold and b) the patient input via the user interface indicating the initiation or termination of the high-noise activity, cause, in response to indication of the initiation of the high-noise activity, the arrhythmia detection process to execute in the AIN robust mode, and cause, in response to indication of the termination of the high-noise activity, the arrhythmia detection process to execute in the AIN sensitive mode.

Implementations of the second wearable medical device for monitoring arrhythmias during patient activity can include one or more of the following features.

In the device, the processor can further be configured to receive the one or more electrical signals from the one or more sensing electrodes, determine ECG data for the patient based upon the one or more electrical signals, determine what portion of the ECG data is noisy ECG data caused by patient activity, and determine the patient activity is a high-noise activity if the portion of ECG data that is noisy ECG data exceeds the predetermined noise threshold. In some examples, the noise threshold can include at least one of a detected ECG noise peak more than 25% greater than a calculated R-wave mean value, a detected noise peak more than 50% greater than a calculated R-wave mean value, or a detected noise peak more than 100% greater than a calculated R-wave mean value. In some additional examples, the noise threshold can include a threshold number of ECG noise peaks that are more than 25% greater than a calculated R-wave mean value in a predetermined period of time. In some examples, the threshold number of ECG noise peaks can include at least one of 3 peaks, 5 peaks, 10 peaks, and 15 ECG noise peaks. In some additional examples, the predetermined period of time can include at least one of 30 seconds, 45 seconds, 60 seconds, 75 seconds, 90 seconds, 3 minutes, 5 minutes, 10 minutes, 15 minutes, and 30 minutes. In some examples, the portion of the ECG data can be transformed in a frequency domain, and wherein the noise threshold includes a dominant frequency of at least one of less than 1 Hz and in excess of 20 Hz.

In the device, the at least one processor can be configured to determine the termination of the high-noise activity based on a predetermined time out condition occurring after a predetermined time period. In some examples, the predetermined time period can include at least one of thirty seconds, one minute, two minutes, five minutes, ten minutes, fifteen minutes, twenty minutes, and thirty minutes. In some additional examples, the at least one processor can be configured to, when the predetermined time out condition occurs, prompt the patient to indicate whether the high-noise activity has terminated. In some examples, the at least one processor can be configured to suspend determination of the termination of the high-noise activity for a second predetermined time period if the patient indicates that the high-noise activity has not terminated. In some additional examples, the second predetermined time period can include at least one of thirty seconds, one minute, two minutes, five minutes, ten minutes, fifteen minutes, twenty minutes, and thirty minutes.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples and are incorporated in and constitute a part of this specification but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1A:
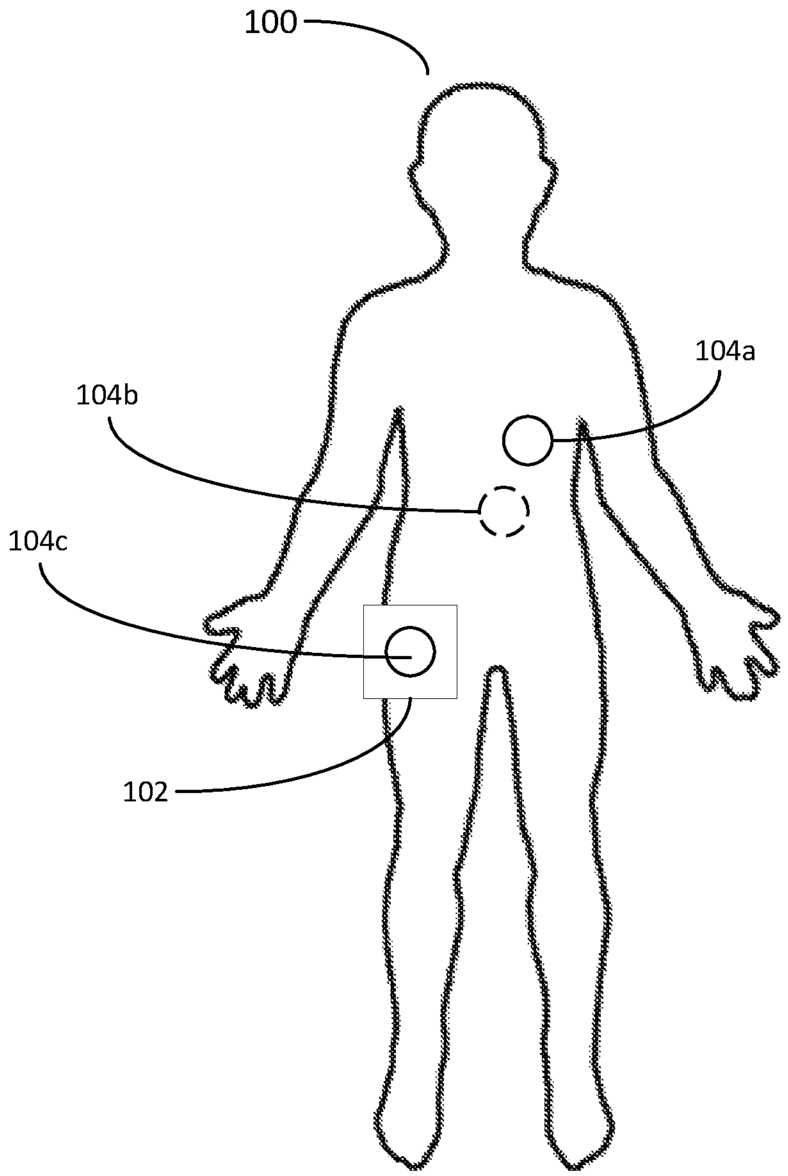
FIGS. 1A-1C illustrate sample motion sensor arrangements for a patient, in accordance with an example of the present disclosure.

Wearable medical devices, such as cardiac event monitoring and treatment devices, are used in clinical or outpatient settings to monitor and/or record various ECG and other physiological signals of a patient. These ECG and other physiological signals can be used to determine a current condition of a patient, monitor for arrhythmias, and provide treatment such as a defibrillation shock in the event of life-threatening arrhythmias.

During monitoring of a patient, the patient may engage in a high-noise, physical activity such as walking, running, climbing stairs, riding a bicycle, riding in a car, and other similar activities. During such an activity, sensors configured to monitor the ECG and other physiological signals of a patient may move against the patient's skin or detach from the patient's skin entirely. Such movement or detachment can cause noise in the output from the sensors. When monitoring the patient for a cardiac event such as an arrhythmia, any noise in, for example, ECG signals can potentially cause misdiagnosis of an arrhythmia or a missed arrhythmia experienced by the patient.

Misdiagnosis or missing an arrhythmia due to noise resulting from a physical activity can have several drawbacks. For example, if an arrhythmia is misdiagnosed due to noise caused by a physical activity, a patient may be improperly treated for an arrhythmia they are not experiencing. If the patient is engaging in an activity, the patient may not perceive an alarm or other warnings produced by the device before an improper treatment. In certain other scenarios, if an arrhythmia is misdiagnosed due to noise, the patient has to cease the physical activity to address the false alarm. If such false alarms occur frequently, the patient can develop alarm fatigue and lose confidence in the device. For instance, the patient may lose motivation to comply with device use guidelines and wear the device less often, thus putting herself or himself at risk. Similarly, if an arrhythmia is missed entirely, a patient will not be treated at all for an arrhythmia they are experiencing. It is therefore advantageous to determine a type of motion and determine what actions, if any, may be taken to address the noise or disruption based on the motion type with minimal disruption to the patient's normal daily routine.

To address these and other obstacles to successful execution of arrhythmia monitoring, systems and processes configured to classify motion data and modify arrhythmia monitoring based upon the motion classification are provided. For example, a wearable medical device such as a wearable cardioverter defibrillator (WCD) can include multiple ECG monitoring modes that can be selected by a processor based upon whether a patient wearing the medical device is participating in a high-noise activity. For example, the multiple ECG monitoring modes can include an activity-induced noise (AIN) sensitive mode where the full ECG signals are monitored for any cardiac events, such as arrhythmias. The multiple ECG monitoring modes can further include a second, noise robust monitoring mode such as an AIN robust mode that monitors a subset of ECG metrics, such as heart rate metrics or one or more QRS width metrics, during a high-noise activity. The devices as described herein can automatically switch from the AIN sensitive mode to an AIN robust mode, or vice versa, based on an analysis of the motion information from the patient and/or amount of noise on the ECG channel(s). Alternatively or in addition, the devices as described herein can switch from the AIN sensitive mode to an AIN robust mode, or vice versa, based on a user input indicating an initiation or termination of a high noise activity.

For example, a WCD for monitoring arrhythmias during different types of patient activities can include a memory configured to store parameters relating to an arrhythmia detection process, and a processor configured to execute the arrhythmia detection process based on such parameters. In certain implementations, the processor can cause the arrhythmia detection process to be configured to execute in one of an AIN sensitive mode and an AIN robust mode depending upon a physical activity of a patient and a signal noise level associated with the activity. AIN sensitive mode will be able to discern finer features in the ECG and thus be able to estimate more accurately the underlying state of the cardiovascular system, but only when the activity-induced noise levels are sufficiently low (e.g., below a predetermined threshold level set as described in further detail below). For example, the predetermined threshold level can be configured via one or more user configurable parameters input through a user interface during an initial set up or baselining phase of outfitting the patient with the WCD. For example, during the AIN sensitive mode, the WCD may perform detailed arrhythmia monitoring such as P-wave detection, measurement and analysis, such as PR interval and P-wave amplitude and morphology; small T-wave detection measurement and analysis, such as QT-interval measurements; ST segment measurement and analysis; U-wave detection and measurement; and associated one or more metrics relating to each of the foregoing or a combination of one or more of the foregoing. On the other hand, the AIN robust mode will remain accurate in the presence of AIN but shall be configured to not measure the finer ECG features and instead focus on a coarser estimate of the underlying state of the cardiovascular system. Such coarser estimated features can include: QRS detection and related RR interval measurements; QRS width measurements; larger R wave amplitude measurements; larger amplitude T-wave measurements; and associated one or more metrics relating to each of the foregoing or a combination of one or more of the foregoing. The WCD includes a processor that is configured to cause the arrhythmia detection process to execute in the AIN sensitive mode during normal wearing of the WCD. In some examples, the processor can determine initiation of a high-noise activity based on at least one of a) motion signals received from one or more motion sensors coupled to the processor and b) a patient input via a user interface operably coupled to the processor. In examples, if the processor detects a high-noise activity, the processor can cause the arrhythmia detection process to automatically execute in the AIN robust mode. Upon termination of the high-noise activity, the processor can cause the arrhythmia detection process to automatically revert back to the AIN sensitive mode. In some examples, the processor may be configured to have the AIN sensitive mode be the default operational mode at power-on or restart of the device, e.g., after the batteries have been replaced or recharged. In examples, a caregiver, a technician, a patient, or other such authorized person may cause the processor to have the AIN robust mode be the default operational mode at power-on or restart of the device. For example, the authorized person may interface with a user interface to modify a parameter indicating a default ECG monitoring mode in order to affect such operation.

In a similar example, a wearable medical device such as a WCD can further include determining whether a patient is potentially experiencing an arrhythmia when engaged in a high-noise activity. For example, the device can be monitoring the patient during the high-noise activity using the AIN robust monitoring mode. During the physical activity, the device may determine that the patient is potentially experiencing a cardiac event such as an arrhythmia. The device can provide a notification to the patient to stop the physical activity and the device can resume monitoring the patient using the AIN sensitive monitoring mode. Based upon monitoring the patient using the AIN sensitive mode, the device can treat the patient if needed. Such a process provides added verification that a patient is experiencing an arrhythmia using the AIN sensitive monitoring prior to treating.

For example, a WCD for monitoring arrhythmias during different types of patient activities can include an arrhythmia detection process configurable to execute in one of an AIN sensitive mode and an AIN robust mode as described above. The WCD can further include a processor that is configured to initially cause the arrhythmia process to operate in a default ECG monitoring mode, e.g., AIN sensitive mode. Upon detection that a patient is performing a physical activity such as walking or running, the processor can automatically cause the arrhythmia detection process to operate in the AIN robust mode. During the physical activity, if the arrhythmia detection process determines a possible life-threatening condition in the patient such as a potential arrhythmia, the processor can provide a notification to the patient indicating that the patient should pause or stop the physical activity. The processor can then cause the arrhythmia detection process to operate in the AIN sensitive mode to confirm the life-threatening condition. If the life-threatening condition is confirmed, the processor can initiate a treatment to the patient.

As an example, a wearable medical device for monitoring arrhythmias during patient activity is described herein. The device can include a plurality of electrodes configured to monitor for a cardiac arrhythmia and provide a therapeutic shock to a patient in response to detecting the cardiac arrhythmia. The device includes a user interface configured to receive patient input indicating one of initiation or termination of a high-noise activity. The device includes one or more accelerometers configured to generate a plurality of motion signals representative of movement of a patient indicative of whether the patient is engaged in the high-noise-activity. In the device, at least one processor is configured to monitor for indication of initiation or termination of the high-noise activity. The at least one processor can perform such monitoring based on at least one of the plurality of motion signals and the patient input via the user interface indicating the initiation or termination of the high-noise activity.

The at least one processor can cause, in response to indication of the initiation of the high-noise activity, the arrhythmia detection process to execute in the AIN robust mode. The at least one processor can be caused to automatically execute in the AIN robust mode based on the motion signals. Alternatively or in addition, the at least one processor can be caused to execute in the AIN robust mode based on a user input indicating that the patient is initiating the high-noise activity.

Further, in response to indication of the termination of the high-noise activity, the at least one processor can cause the arrhythmia detection process to execute in the AIN sensitive mode. The at least one processor can be caused to automatically execute in the AIN sensitive mode based on the motion signals. Alternatively or in addition, the at least one processor can be caused to execute in the AIN sensitive mode based on a user input indicating that the patient is terminating the high-noise activity.

In some examples, to accurately determine whether the patient is engaged in a physical activity that may cause high-noise, a motion classifier can be used to determine what type of activity the patient is engaging in. For example, measured motion data as collected by one or more accelerometers within the wearable medical device can be used to classify motion of the patient as, for example, walking, running, climbing stairs, and other similar physical activities.

For example, a WCD for providing adaptive noise notifications based upon motion classification can include one or more motion sensors configured to generate a plurality of motion signals related to a physical activity the patient is engaged in. A processor operably coupled to the one or more motion sensors can receive the motion signals and extract one or more motion features from the data. The processor can configure the extracted motion features into a motion feature vector and input the vector into a motion classifier. Based upon the output of the motion classifier, the processor can determine what activity the patient is currently engaged in. Based upon this determination, the processor can update or otherwise modify arrhythmia monitoring of the patient accordingly as described herein.

These examples, and various other similar examples of benefits and advantages of the techniques, processes, and approaches as provided herein, are described in additional detail below.

The various monitoring processes as described herein are implemented, in some examples, by data processing devices, such as computer systems and certain types of medical devices. For instance, some examples include a patient monitoring and treatment device. Patient monitoring and treatment devices are used to monitor and record various physiological or vital signals for a patient and provide treatment to a patient when necessary. For patients at risk of a cardiac arrhythmia, specialized cardiac monitoring and/or treatment devices such as a cardiac event monitoring device, a WCD, or a hospital wearable defibrillator can be prescribed to and worn by the patient for an extended period of time. For example, a patient having an elevated risk of sudden cardiac death, unexplained syncope, prior symptoms of heart failure, an ejection fraction of less than 45%, less than 35%, or other such threshold deemed of concern by a physician, and other similar patients in a state of degraded cardiac health can be prescribed a specialized cardiac monitoring and/or treatment device.

For example, a WCD such as the LifeVest® Wearable Cardioverter Defibrillator from ZOLL Medical Corporation (Chelmsford, MA), can be prescribed to the patient. As described in further detail below, such a device includes a garment that is configured to be worn about the torso of the patient. The garment can be configured to house various components such as ECG sensing electrodes, therapy electrodes, and one or more accelerometers configured to measure motion data for the patient. The components in the garment can be operably connected to a monitoring device that is configured to receive and process signals from the ECG sensing electrodes to determine a patient's cardiac condition and, if necessary, provide treatment to the patient using the therapy electrodes. Additionally, the monitoring device can be used to determine if the patient is engaging in a high-noise activity and to adjust the monitoring mode of the device accordingly.

Figure 1B:
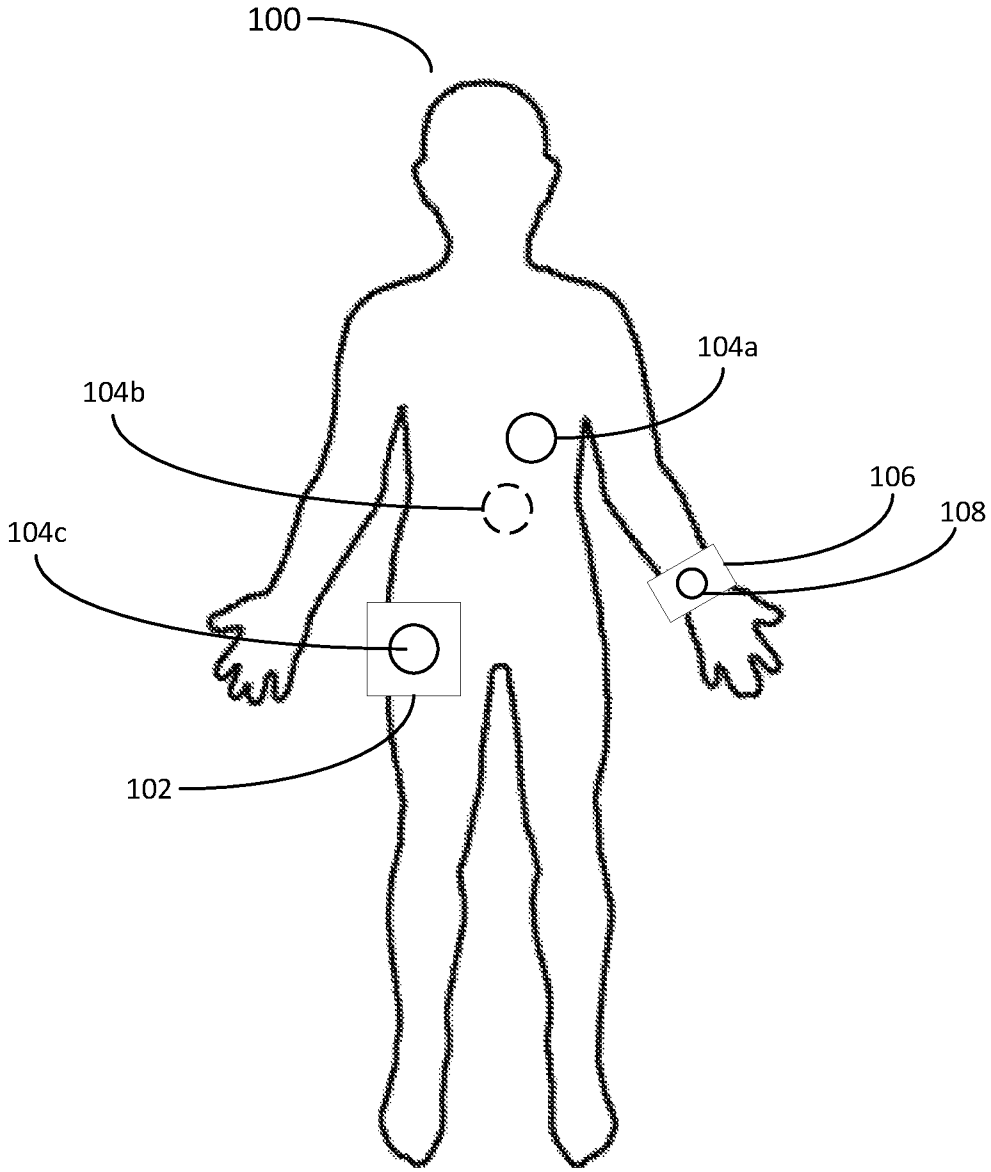
Figure 1C:
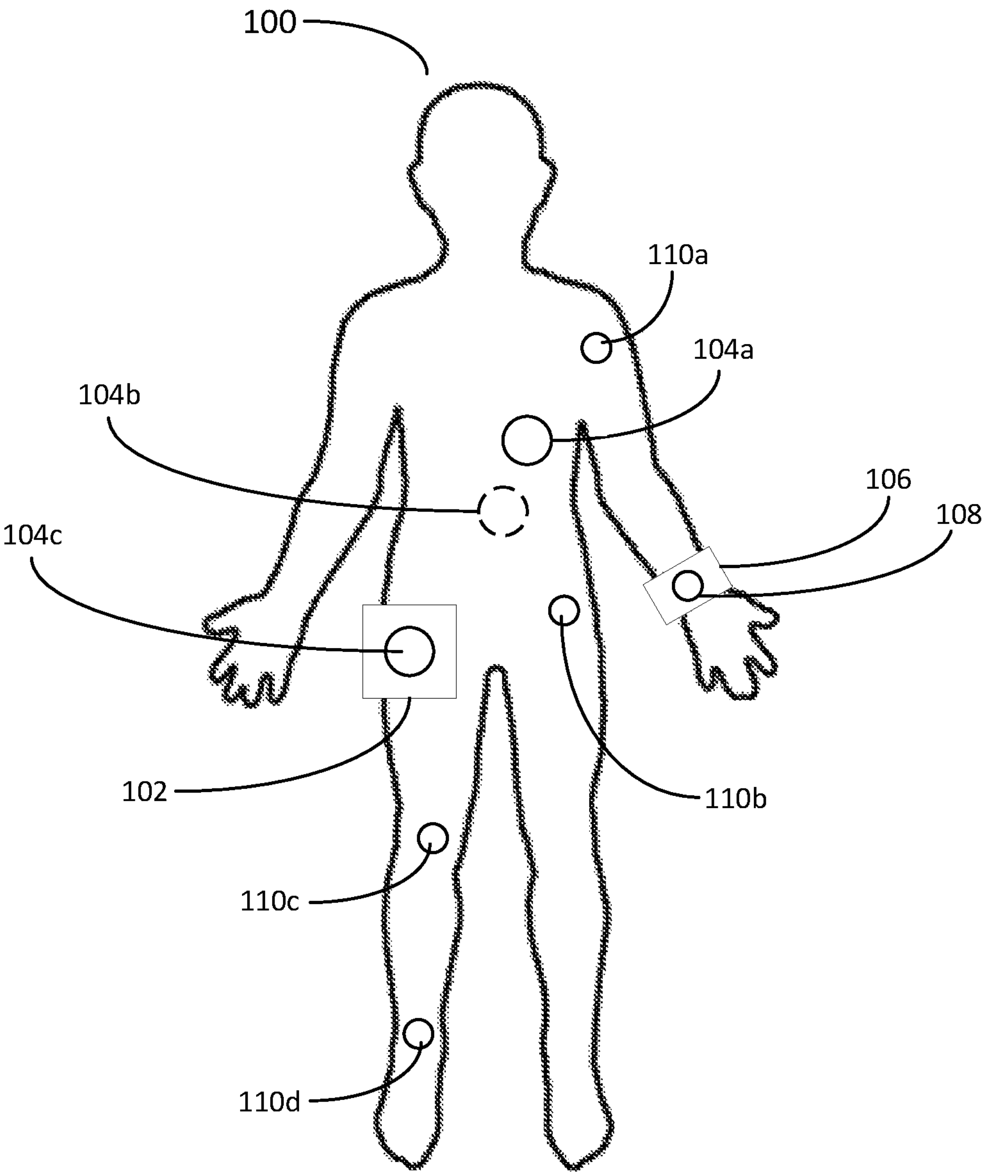

FIGS. 1A-1C illustrate various examples of a patient 100 wearing one or more motion sensors such as accelerometers as described herein. It should be noted that accelerometers are described herein as examples of motion sensors for illustrative purposes only. In certain implementations, additional motion sensors such as gyroscopes, magnetic sensors, pressure-based motion sensors, and other similar motion sensors can be used.

As shown in FIG. 1A, a patient can be prescribed an ambulatory medical device such as a WCD. The WCD can include a controller 102 that is operably connected to one or more sensing electrodes and therapy electrodes. Additional details of one example of the controller 102 can be found in the discussion of FIG. 3 below.

The WCD can also include one or more accelerometers or other motion sensors. As shown in FIG. 1A, the WCD can include three accelerometers 104*a*, 104*b*, and 104*c* (collectively referred to as accelerometers 104) positioned at various places on the body of patient 100. For example, accelerometer 104*a* can be positioned on the front of chest of the patient 100, the accelerometer 104*b* can be positioned on the back of the patient, and the accelerometer 104*c* can be integrated into the controller 102. Each of the accelerometers 104 can be configured to measure movement associated with the patient 100 and to output an electrical signal indicating a direction and magnitude of the movement of the patient.

It should be noted that the number and arrangement of the accelerometers 104 as shown in FIG. 1 is by way of example only. In certain implementations, the number and position of the accelerometers 104 can vary. Additionally, when included in a device such as a WCD, one or more of the accelerometers 104 can be integrated into components of the WCD. For example, as noted above, the accelerometer 104*c* can be integrated into a controller 102 of the WCD. Similarly, one or more of accelerometers 104*a* and 104*b* can be integrated into one or more components of a WCD. For example, the front accelerometer 104*a* can be integrated into, for example, a therapy electrode operably connected to the controller 102 and configured to provide a therapeutic shock to patient 100. In some implementations, the accelerometer 104*a* can be integrated into a sensing electrode configured to measure electrical signals produced by patient 100 and indicative of cardiac activity of the patient. Similarly, accelerometer 104*b* can be integrated into one or more components of a WCD such as a connection node, a sensing electrode, a therapy electrode, and other similar components of a WCD as described herein.

In addition to accelerometers associated with a WCD as described above in regard to FIG. 1A, a patient such as patient 100 can also wear additional accelerometers integrated into, for example a wearable motion detection device such as a fitness tracker. As shown in FIG. 1B, patient 100 can wear a wrist-worn motion tracking device 106. For example, the device 106 can be implemented as a fitness tracker configured to measure movement and translate the movement into indications of physical activities such as walking, running, climbing stairs, and other similar physical activity. In some examples, the device 106 can be implemented as a standalone fitness tracking device or be implemented into another device such as a smartwatch.

As further shown in FIG. 1B, the device 106 can include one or more additional accelerometers 108. In the example shown in FIG. 1B, the accelerometers 104 can be on the trunk or core of the patient 100 and can be configured to measure overall body movements while accelerometers 108 can be positioned on the wrist (or another similar extremity) and be configured to measure motion of the arm of the patient.

However, it should be noted that device 106 and accelerometers 108 are shown by way of example only. In some implementations, a patient such as patient 100 can wear additional accelerometers that are configured to collect additional motion data for the patient. For example, as shown in FIG. 1C, the patient 100 can wear additional accelerometers located on different portions of the patient's body such as left or right shoulder, 110*a*, left or right upper leg or left or right hip area 110*b*, left or right mid-leg or knee area 110*c*, and left or right lower leg 110*d* (collectively referred to as accelerometers 110). In some examples, the accelerometers 110 can be integrated into one or more articles of clothing or wearable garments such as a belt configured to go around the waist or chest of the patient 100, a brace or strap configured to go around the knee or ankle of the patient, and other similar articles of clothing or wearable garments. In examples, one or more of the accelerometers 110 can be wireless accelerometers. For example, a wireless accelerometer can include a tilt sensor such as part number MNS-9-W1-AC-TL from Monnit of Salt Lake City, Utah, USA.

It should be noted that the placement and number of accelerometers as shown in FIGS. 1A-1C are shown by way of example only. In actual implementation of the motion measuring and classification techniques as described herein, the number and position of the accelerometers can vary based upon the anticipated activity level of the patient, the type of activity the patient is expected to undertake, and other various factors.

To properly acquire and output a signal indicative of a patient's movement, an accelerometer such as those described above in FIGS. 1A-1C can be configured to output one or more output signals indicative of any detected movement or motion. As described herein, patient motion can cause noise and artifacts in ECG signals that interfere with automatic processing and interpretation of those signals. System awareness of such motion data can be useful for modifying signal interpretation (e.g., changing signal processing methods and/or ignoring particular noisy signals). When analyzing the motion data, it can be beneficial to determine is the patient moving (e.g., patient tracking), what type of physical activity is the patient engaged in, and is the patient motion or activity likely to cause noise or other artifacts in the ECG data? Each of these questions can be addressed by analyzing the output of one or more motion sensors such as a tri-axial accelerometer as described herein. In some examples, the motion data can be analyzed in a sliding time window between, for example, two and twenty seconds. The analysis can generate outputs in shorter time periods that the window duration, for example one second outputs, such that the windows overlap in time.

Figure 2:
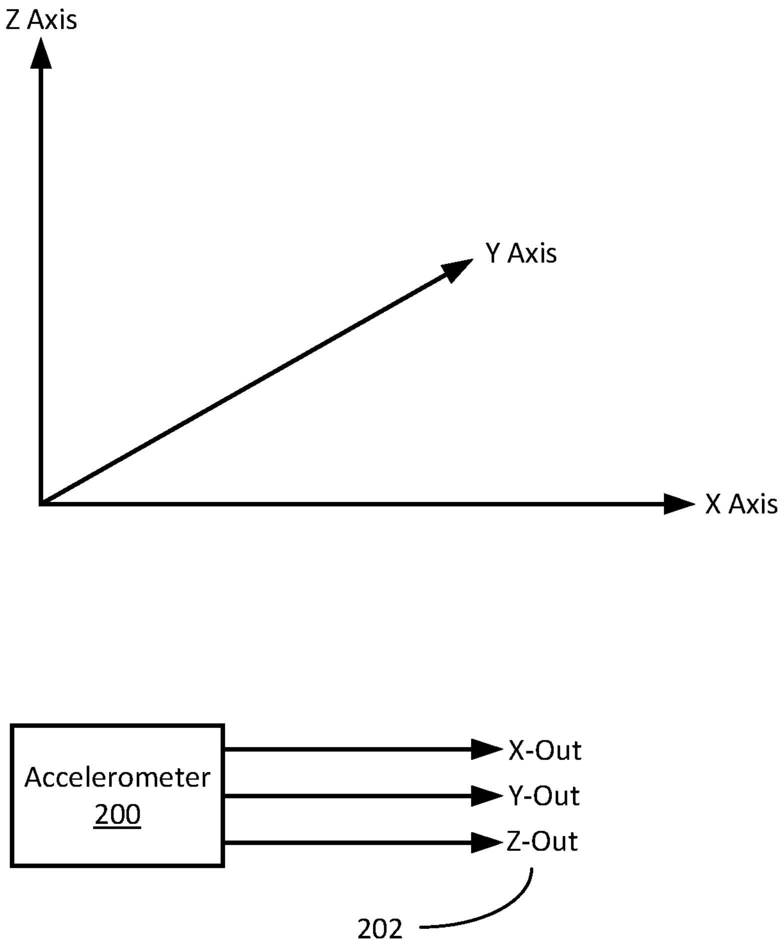
FIG. 2 illustrates the output of a sample accelerometer, in accordance with an example of the present disclosure.

For example, as shown in FIG. 2, an accelerometer 200 can be configured to measure movement in three axes: the x-axis, the y-axis, and the z-axis. Depending upon the orientation of the accelerometer 200 and the output configuration of the accelerometer, the individual axes can define movement of the accelerometer in a specific direction.

Additionally, as shown in FIG. 2, the accelerometer 200 can be configured to provide one or more outputs 202. In this example, the outputs 202 can include an X-out (i.e., a signal indicative of measured movement along the x-axis), a Y-out (i.e., a signal indicative of measured movement along the y-axis), and a Z-out (i.e., a signal indicative of measured movement along the z-axis).

In some implementations, an accelerometer such as accelerometer 200 can be configured to output an electrical signal on each output 202 having one or more controlled characteristics such as voltage. For example, the accelerometer 200 can be configured to output a signal on each output 202 between 0 and 5 volts. In some examples, the output voltage on each output 202 can be directly proportional to measured motion on the corresponding axis. For example, if the accelerometer 200 is configured to measure movement of acceleration as a measure of gravitational forces, the accelerometer can be configured to measure a specific range of g-forces such as −5 g to +5 g. In such an example, the output voltage on each output 202 can be directly proportional to the measured g-force on each axis. For example, of no g-forces are measure (i.e., the accelerometer 200 is at rest), each output signal 202 can be measured at 2.5 volts. If a movement having a positive g-force along an axis is measured, the voltage on the corresponding output 202 can increase. Conversely, if a movement having a negative g-force along an axis is measured, the voltage on the corresponding output 202 can decrease. Table 1 below shows sample voltage output levels for an accelerometer configured to measure between −5 g and +5 g and output a signal between 0 and 5 volts.

TABLE 1

| Measured G-Force | Output Voltage |
|---|---|
| −5 g | 0 volts |
| −4 g | 0.5 volts |
| −3 g | 1.0 volts |
| −2 g | 1.5 volts |
| −1 g | 2.0 volts |
| 0 g | 2.5 volts |
| 1 g | 3.0 volts |
| 2 g | 3.5 volts |
| 3 g | 4.0 volts |
| 4 g | 4.5 volts |
| 5 g | 5.0 volts |

It should be noted that sample g-force and voltage ranges as described above and shown in Table 1 are provided by way of example only for illustrative purposes. Depending upon the design and capabilities of the accelerometers used, the g-force ranges measured, and the corresponding output voltages can vary accordingly.

In certain implementations, raw data from an accelerometer can take the form of a time series of acceleration values in each of the x-axis, the y-axis, and the z-axis. As noted above, raw output from analog accelerometers can be a continuous voltage that is proportional to the acceleration (as shown in Table 1 above) or a square-wave where the duty cycle is proportional to the acceleration (e.g., pulse-width modulation). When using an analog accelerometer, additional circuitry such as an accelerometer interface as described below can be included to provide the acceleration data in a time series.

In certain implementations, the output for each time step for a set of motion data can be represented as a vector:

$$a = [a_x, a_y, a_z]$$

where $a_x$, $a_y$, and $a_z$ are the x-axis, y-axis, and z-axis components of acceleration as measured by the accelerometer. A time series of accelerometer magnitudes can thus be denoted as:

$$[\|a[t-NT]\|, \ldots, \|a[t-2T]\|, \|a[t-T]\|, \|a[t]\|]$$

where $\|a[t]\|$ is the magnitude of the acceleration vector at time t, T is the sampling period (e.g., 20 milliseconds), and N is the number of consecutive prior samples being analyzed.

Figure 3:
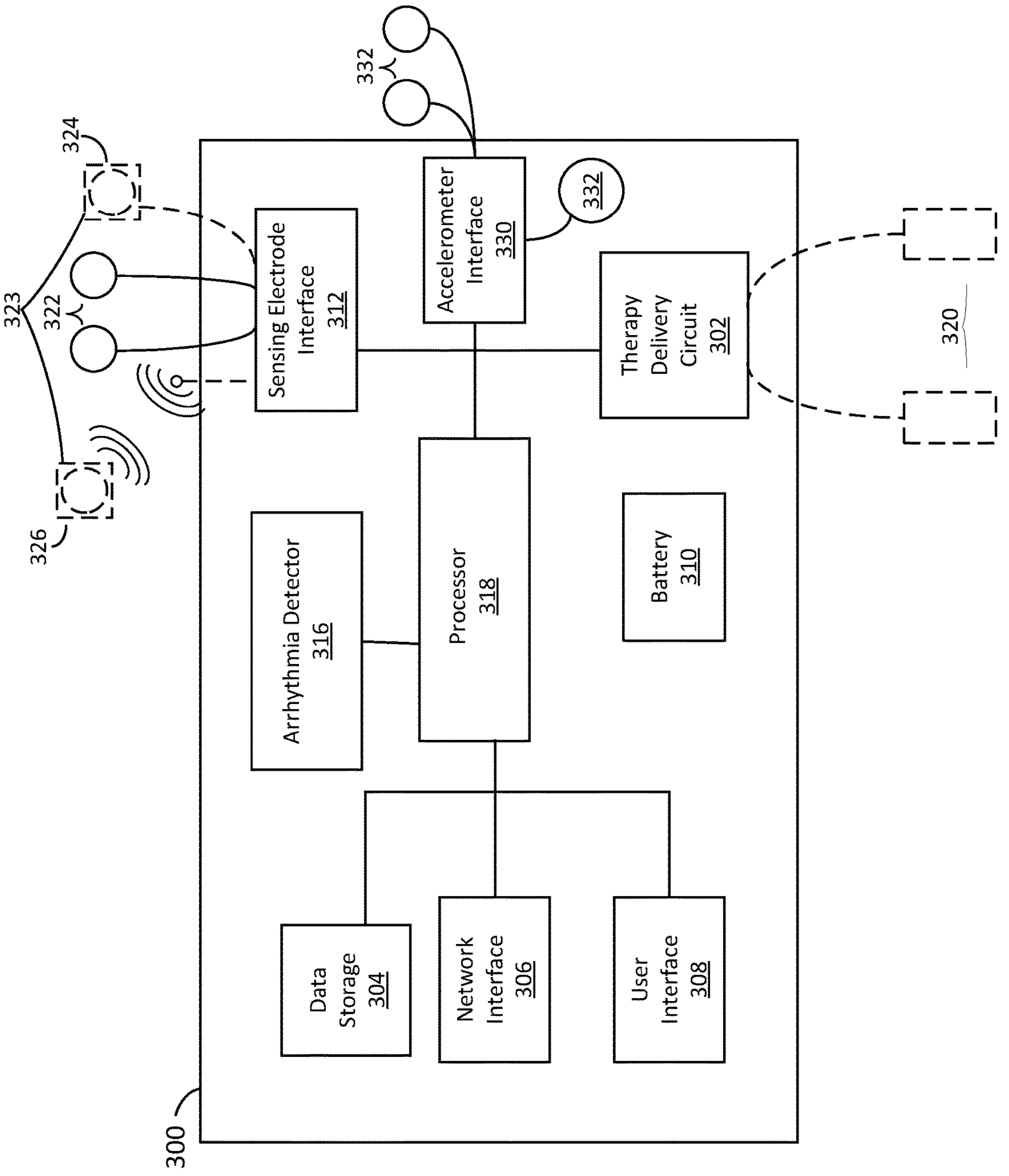
FIG. 3 illustrates a schematic view of a sample controller for a wearable medical device, in accordance with an example of the present disclosure.

FIG. 3 illustrates an example component-level view of the medical device controller 300 included in, for example, a wearable medical device such as a WCD. The medical device controller 300 is one example of the controller 102 shown in FIGS. 1A-1C and described above. As shown in FIG. 3, the medical device controller 300 can include a housing 301 configured to house therapy delivery circuitry 302 configured to provide one or more therapeutic shocks to the patient via at least two therapy electrodes 320, a data storage 304, a network interface 306, a user interface 308, at least one rechargeable battery 310 (e.g., within a battery chamber configured for such purpose), a sensor interface 312 (e.g., to interface with both ECG sensing electrodes 322 and non-ECG physiological sensors 323 such as vibrational sensors, lung fluid sensors, infrared and near-infrared-based pulse oxygen sensor, blood pressure sensors, among others), a cardiac event detector 316, and least one processor 318.

In some examples, the patient monitoring medical device can include a medical device controller 300 that includes like components as those described above but does not include the therapy delivery circuitry 302 and the therapy electrodes 320 (shown in dotted lines). That is, in certain implementations, the medical device can include only ECG monitoring components and not provide therapy to the patient. In such implementations, the construction of the patient monitoring medical device is similar in many respects as a WCD medical device controller 300 but need not include the therapy delivery circuitry 302 and associated therapy electrodes 320.

As further shown in FIG. 3, the controller 102 can further include an accelerometer interface 330 and a set of accelerometers 332. The accelerometer interface 330 can be operably coupled to each of the accelerometers 332 and configured to receive one or more outputs from the accelerometers. The accelerometer interface 330 can be further configured to condition the output signals by, for example, converting analog accelerometer signals to digital signals (if using an analog accelerometer), filtering the output signals, combining the output signals into a combined directional signal (e.g., combining each x-axis signal into a composite x-axis signal, combining each y-axis signal into a composite y-axis signal, and combining each z-axis signal into a composite z-axis signal). In some examples, the accelerometer interface 330 can be configured to filter the signals using a high-pass or band-pass filter to isolate the acceleration of the patient due to movement from the component of the acceleration due to gravity.

Additionally, the accelerometer interface 330 can configure the output for further processing. For example, the accelerometer interface 330 can be configured to arrange the output of an individual accelerometer 332 as a vector expressing the acceleration components of the x-axis, the y-axis, and the z-axis as received from each accelerometer. The accelerometer interface 330 can be operably coupled to the processor 318 and configured to transfer the output signals from the accelerometers 332 to the processor for further processing and analysis.

As described above, one or more of the accelerometers 332 can be integrated into one or more components of a medical device. For example, as shown in FIG. 3, an accelerometer 332 can be integrated into the controller 300. In some examples, an accelerometer 332 can be integrated into one or more of a therapy electrode 320, a sensing electrode 322, a physiological sensor 323, and into other components of a medical device.

As noted above, when a patient is engaged in a high-noise physical activity, patient movement can cause activity-induced noise in signals received from the ECG sensing electrodes. This activity-induced noise can cause an arrhythmia detection process to incorrectly identify an arrhythmia. As such, as described herein, a medical device controller can be configured to monitor for motion data from, for example, an accelerometer interface as described above, the motion data indicative of movement of the patient, coordinate the motion data with any measured or otherwise detected noise from the ECG sensing electrodes and, if there is noise being caused by movement of the patient, to adjust the monitoring of the patient's cardiac activity during the patient movement.

Figure 4:
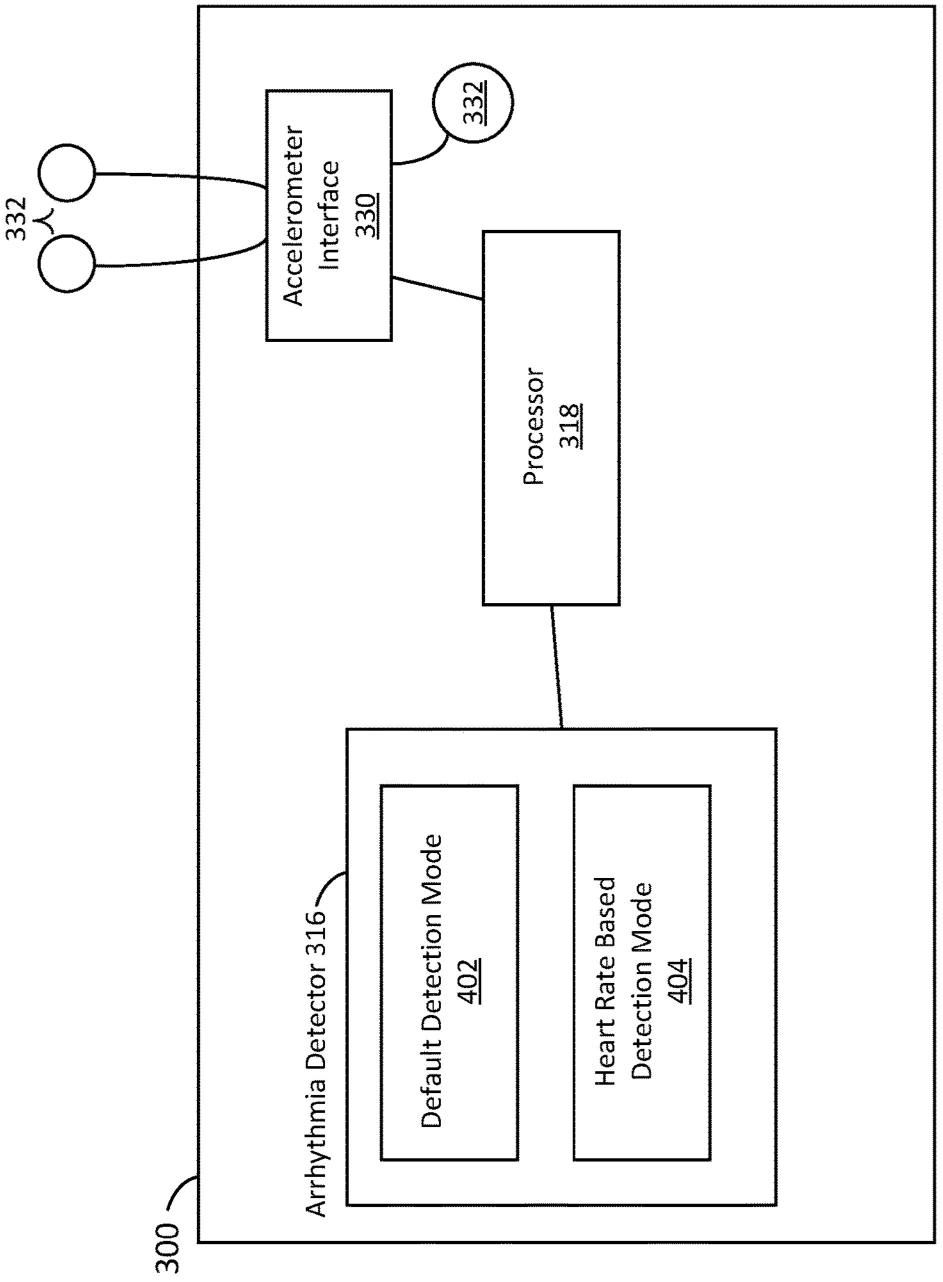
FIG. 4 illustrates a sample controller having multiple arrhythmia detection modes, in accordance with an example of the present disclosure.

As shown in FIG. 4, the arrhythmia detector 316 of medical device controller 300 can include multiple ECG monitoring and/or detection modes. For example, the arrhythmia detector 316 can include multiple arrhythmia detection processes. As shown in FIG. 4, the arrhythmia detector 316 can include an AIN sensitive mode 402 that includes a more exhaustive analysis of the patient's ECG signals for indication of any cardiac activity that may indicate that the patient is experiencing an arrhythmia. If the processor 318 has detected noise associated with certain predetermined patient activity, the processor can switch to an alternative monitoring mode of arrhythmia detection, such as the AIN robust mode. During high noise activities, the ECG signal data is unreliable for arrhythmia detection and as such the AIN sensitive mode may be prone to more false positives as compared to when not operating during high noise activities. For example, as shown in FIG. 4, the arrhythmia detector 316 can also include an AIN robust mode 404 that is configured to monitor the patient's heart rate during the high-noise activity to determine if the patient is likely to be experiencing an arrhythmia. During a high-noise activity, heart rate can be relatively reliably measured as compared to other cardiac metrics derived or otherwise determine based upon analysis of the patient's ECG signal. As such, during a high-noise activity where the ECG signal may be unreliable, heart rate monitoring provides a more reliable method of monitoring at least a portion of a patient's cardiac activity. In certain implementations, the patient's heart rate can be obtained by, for example, monitoring acoustic signals such as heart sounds, using an optical measurement technique such as photoplethysmography, extracting heart rate information from the ECG signal or other similar bio-electrical signals, and other similar heart rate measurement techniques. In some examples, alternatively or in addition to heart rate monitoring, in the AIN robust mode, the processor is configured to monitor for coarser estimates of the underlying state of the cardiovascular system. As noted above, such coarser estimated features can include: QRS detection and related RR interval measurements; QRS width measurements; larger R wave amplitude measurements; larger amplitude T-wave measurements; and associated one or more metrics relating to each of the foregoing or a combination of one or more of the foregoing. The determination of when to use a particular monitoring mode is described in greater detail in the discussions of FIGS. 5 and 6 below.

Figure 5:
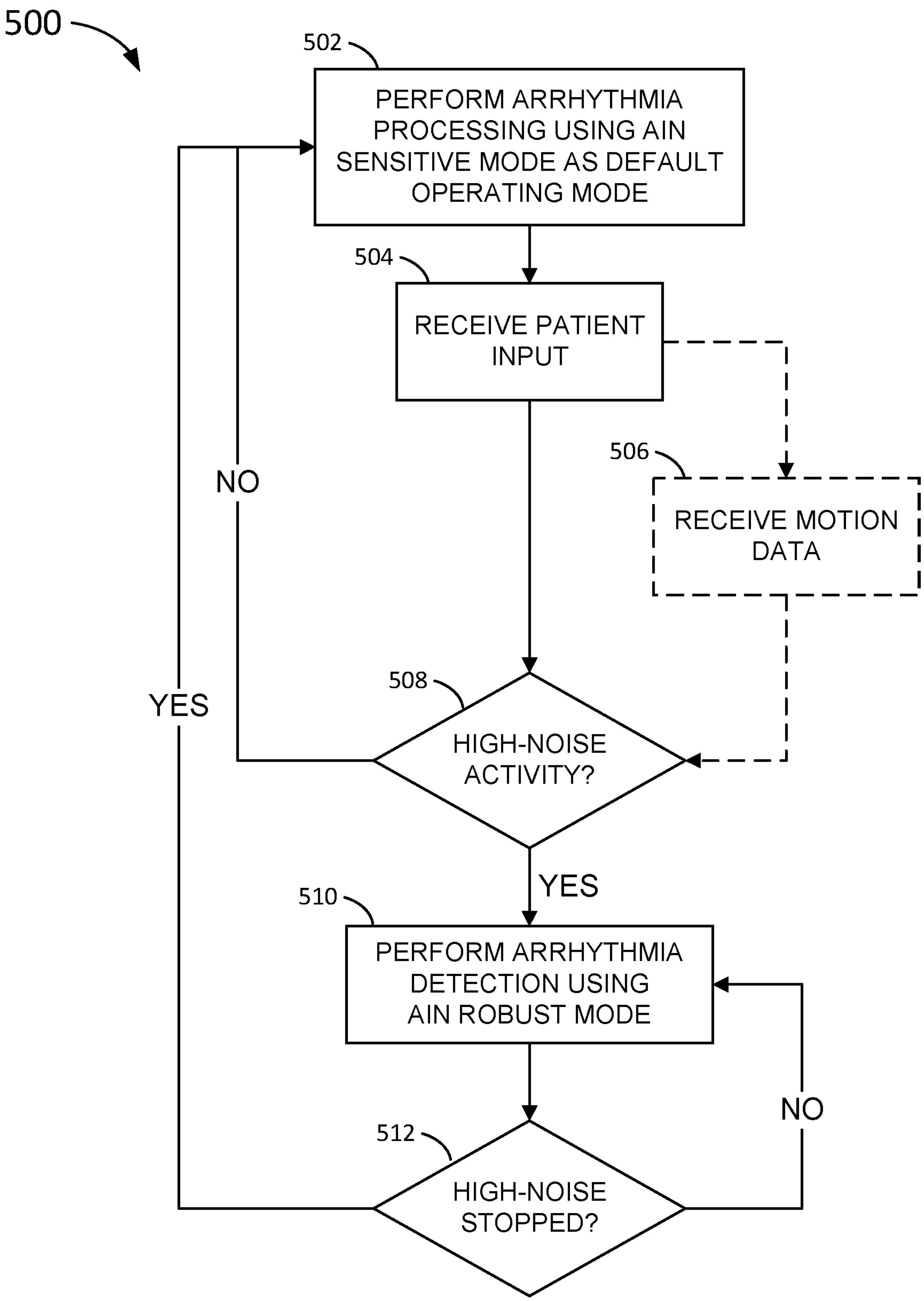
FIG. 5 illustrates a process flow for determining which monitoring mode to use when monitoring the patient for an arrhythmia, in accordance with an example of the present disclosure.

FIG. 5 illustrates a sample process for determining which monitoring mode to use for a particular patient wearing a medical device. For example, as noted above, an arrhythmia detector such as arrhythmia detector 316 can include multiple modes for monitoring a patient. Based upon the current physical activity of the patient, a processor such as processor 318 as described above can determine which particular monitoring mode to use.

As shown in FIG. 5, a process 500 includes the processor initially performing 502 arrhythmia processing using an AIN sensitive mode as the default operating mode. As described herein, default arrhythmia processing in AIN sensitive mode can include monitoring based on finer ECG parameter monitoring such as P-wave detection, measurement and analysis, such as PR interval and P-wave amplitude and morphology; small T-wave detection measurement and analysis, such as QT-interval measurements; ST segment measurement and analysis; U-wave detection and measurement; and associated one or more metrics relating to each of the foregoing or a combination of one or more of the foregoing. The processor can operate in the AIN sensitive mode to monitor the patient for any indications of abnormal cardiac behavior based on such finer ECG parameter monitoring. In some examples, while performing AIN sensitive mode 502, the processor can receive patient input, e.g., via a user interface on the WCD. For example, the patient input can include an indication that the patient is about to perform a physical activity that may introduce noise or other similar signal disturbances to the ECG signals as detected by the ECG sensors. If the patient has opted to provide such input, the WCD user interface can display a screen requesting the patient to specify the type of activity. For example, the user interface may display the following as options for the patient to select: aerobic activity, bicycling, walking, running, climbing stairs, travel within moving vehicle, or other activity type. If the patient selects the other activity type option, the user interface may prompt the patient to type in information regarding the nature of the activity. The patient's input regarding the other activity type may be useful in classifying future patient activities and/or behaviors using the machine learning based classification scheme as described below. In examples, the patient may be ready to initiate a brisk walk, or a bicycling activity. In some cases, the patient may be ready to initiate travel over a rocky terrain in a moving vehicle that may impart noise in the ECG signal. In some cases, the patient may be about to embark on a brisk climb up a series of stairs. Additionally or alternatively, the processor can optionally receive 506 motion data received from, for example, an accelerometer interface such as interface 330 as described above in addition to the patient input. In some examples, the processor can receive 506 the motion data directly from one or more accelerometers such as accelerometers 332 as described above.

In certain examples, the motion data can be received for each time point in a set of time points. For example, motion data can be received for each second that the patient is wearing the medical device. Based upon this, the processor can assign an activity label to the patient for each point in time, e.g., for each second. The activity label can include active or inactive. Additionally, when labeled as active, the activity label can further include an activity type such as walking, running, climbing stairs, and other similar activities.

As further shown in FIG. 5, the processor can analyze the user input and, if received, the motion data to determine 508 if the patient is performing a high-noise activity. In certain implementations, the processor can default to determining 508 that the patient is performing a high-noise activity in response to the user input. In some examples, the process can further analyze both the motion data and the user input to determine 508 if the user is performing a high-noise activity. For example, a high noise activity can include any activity during which the motion data exceeds a particular measured level above an accepted, configurable threshold. For example, a normal accepted threshold can be 1 g for particular patient. Any activity which causes the measured motion data to exceed the accepted threshold by, for example, a certain percentage can be classified as a high-noise event. For example, if a particular activity causes the measured motion data to exceed the accepted threshold by one of 50%, 100%, 150%, 200%, and other similar percentages, the activity can be classified as a high-noise activity.

In some implementations, to determine 508 if the patient is active and engaged in a potentially high-noise activity, the processor can measure the entropy of the magnitude of accelerometer outputs as included in the motion data for a given time t in a window of time (e.g., 20 seconds) leading up to time t. In some examples, the entropy can be computed by estimating a discrete probability density function (PDF) P (||a[t]||) from, for example, a histogram of the magnitudes of a filtered accelerometer output sequences in a window of N samples. The entropy can then be represented by:

$$H = -\sum_{i=0}^{N} P(\|a[t-iT]\|)\log P(\|a[t-iT]\|)$$

where H takes on values between zero (least active) and one (most active). A particular activity threshold can be set (e.g., 0.6) to determine if a patient is active or not. The activity threshold can be user-configurable via a user interface. For example, the threshold may be set to 0.6 by default, but a prescriber or other authorized person can adjust the threshold (e.g., change from 0.6 to 0.5 or 0.65, or 0.7). Based upon the likelihood that a patient is active (e.g., if the activity level transgresses the predetermined threshold), the processor can then deem the patient as likely being engaged in a high-noise activity.

In some examples, the processor determines 508 if the patient is engaged in a high-noise activity based upon analysis of artifacts in the patient's ECG signals. For example, in examples where an accelerometer is co-located with (or bonded to) sensing or therapy electrodes as described herein, such accelerometer can be configured to detect slippage of the electrodes with respect to the patient's body. In these examples, the patient's body is modeled as a rigid body. The processor can analyze each acceleration vector from each electrode to derive an overall acceleration vector for the patient's body in a similar manner as described above. If there is no electrode slippage, the overall acceleration vector will be in concordance with the individual electrode acceleration vectors. If slippage occurs, the individual electrode accelerations will fail to satisfy the rigid body constraints and will not be in concordance with the individual electrode acceleration vectors. For example, a predetermined threshold for such measurement can be normalized in a range from 0 to 1, indicative of an amount of deviation or slippage that is detected. On such a scale, a value of 0 corresponds to no slippage—the overall acceleration vector is substantially in concordance with the individual electrode acceleration vectors. On such a scale, a value of 1 is deemed to indicate that the overall acceleration vector is no longer in concordance with the individual electrode acceleration vectors. A predetermined threshold can be set (e.g., 0.6) to determine if a patient is active or not based on such a scale. The predetermined threshold can be user-configurable via a user interface. For example, the threshold may be set to 0.6 by default, but a prescriber or other authorized person can adjust the threshold (e.g., change from 0.6 to 0.5 or 0.65, or 0.7). Based upon the likelihood that a patient is active (e.g., if the monitored normalized slippage value transgresses the predetermined threshold), the processor can then deem the patient as likely being engaged in a high-noise activity. In this manner, in some examples, the processor can be configured to analyze an indication of slippage in addition to ECG noise to determine whether the patient is engaged in a potentially high-noise activity or if noise and artifacts in the ECG signals is being caused by sensor placement or position.

As further shown in FIG. 5, if the processor does not determine 508 that the patient is engaging in a high-noise activity, the processor can continue to perform 502 arrhythmia processing in the AIN sensitive mode. However, if the processor does determine 508 that the patient is engaging in a high-noise activity, the processor can perform 510 arrhythmia processing in the AIN robust mode, such as a heart rate detection mode. For example, the heart rate based arrhythmia detection can include monitoring the patient's heart rate to determine if the patient's heart rate is exceeding a certain threshold. For example, the processor can monitor the patient's heart rate to determine if the patient's heart rate has exceeded one of 100 bpm, 110 bpm, 120 bpm, 130 bpm, 140 bpm, 150 bpm, and other similar heart rates.

During the AIN robust arrhythmia detection, the processor can determine 512 if the high-noise activity has stopped. If the processor determines 512 that the high noise activity has not stopped, the processor can continue to perform 510 the AIN robust arrhythmia detection. If, conversely, the processor has determined 512 that the high-noise activity has stopped, the processor can again perform 502 the AIN sensitive mode arrhythmia processing.

In some examples, the processor can determine 512 that the high-noise activity has terminated based upon a predetermined time out condition occurring after a predetermined time period. In certain implementations, the predetermined time period can include one of 30 seconds, one minute, two minutes, five minutes, ten minutes, fifteen minutes, twenty minutes, thirty minutes, and other similar periods of time. Upon expiration of the predetermined time period, the processor can also prompt the patient to indicate whether the high-noise activity has terminated. In some examples, if the patient indicates that the high-noise activity has not terminated, the processor can suspend determining whether the high-activity noise has terminated for a second predetermined time period. In certain implementations, the second predetermined time period can include 30 seconds, one minute, two minutes, five minutes, ten minutes, fifteen minutes, twenty minutes, thirty minutes, and other similar periods of time. In some examples, if the patient indicates that the high-noise activity has completed, the processor can immediately return to performing 502 the AIN sensitive mode arrhythmia processing.

In certain implementations, the processor can be further configured to determine whether a received ECG signal is noisy based upon the motion data. For example, the processor can be configured to receive one or more electrical signals from one or more sensing electrodes on the patient's body and determine ECG data for the patient based upon the electrical signals. The processor can further coordinate the motion data with the ECG data to determine what portion of the ECG data is noisy ECG data caused by patient activity and, based upon the noisy ECG data, determine whether the patient activity is a high noise activity if the noisy ECG data exceeds a particular threshold. For example, if the ECG data includes a detected R-wave peak that is more than 25% greater than a calculated R-wave mean value for a set of previously detected R-wave peaks or a recorded median R-Wave peak measurement, the ECG data may be characterized as noisy. In some examples, if the ECG data includes a detected R-wave peak that is more than 50% greater than a calculated R-wave mean value for a set of previously detected R-wave peaks or a recorded median R-wave peak measurement, the ECG data may be characterized as noisy. In some other examples, if the ECG data includes a detected R-wave peak that is more than 100% greater than a calculated R-wave mean value for a set of previously detected R-wave peaks or a recorded median R-wave peak measurement, the ECG data may be characterized as noisy. In the above examples, the set of previously detected R-wave peaks can include, in certain implementations, a set of three peaks, five peaks, ten peaks, 15 peaks, 20 peaks, 25 peaks, and 30 peaks. In some examples, ECG data can be determined to be noisy ECG data if a threshold number of R peaks are more than, e.g., 25% greater than a calculated R-wave mean for a set of previously detected R-wave peaks recorded over a period of time. For example, the threshold number of R-wave peaks can be three peaks, five peaks, ten peaks, and 15 peaks. In some examples, the overall period of time can include at least one of 30 seconds, 45 seconds, 60 seconds, 75 seconds, 90 seconds, three minutes, five minutes, ten minutes, 15 minutes, and 30 minutes. For example, the processor can be configured to characterize the amount of noise in the ECG signal based on a normalized scale ranging from 0 to 1. On such a scale, a value of 0 corresponds to substantially minimal noise. For example, during an initial fitting of the device when the device is initially baselined (or, additionally or alternatively, during a subsequent re-baselining period), the patient can be asked to remain still, and the recorded ECG signal can be analyzed for noise content using the technique above. In examples, a re-baselining for calibrating the scale can be performed while the patient is asleep (e.g., based on time of date information indicating a time during the night period and/or lack of motion detected via the accelerometers). This initial or re-baselined state can be deemed to be 0 on the normalized scale. Conversely, a value of 1 is deemed to indicate that the ECG channel is too noisy to discern a usable ECG signal as noted in the examples above. A predetermined threshold can be set (e.g., 0.6) to determine if a patient is active or not based on such a scale. The predetermined threshold can be user-configurable via a user interface. For example, the threshold may be set to 0.6 by default, but a prescriber or other authorized person can adjust the threshold (e.g., change from 0.6 to 0.5 or 0.65, or 0.7). Based upon the likelihood that a patient is active (e.g., if the monitored ECG noise value transgresses the predetermined threshold), the processor can then deem the patient as likely being engaged in a high-noise activity.

In some examples, the processor can be configured to transform the ECG data into a frequency domain. In such examples, if the detected frequency measurement of the ECG data exceeds a predetermined noise threshold the ECG data can be considered to be noisy. For example, if the dominant frequency of the ECG frequency data is less than 1 Hz or in excess of 20 Hz, the processor can determine that the ECG data is noisy. In some examples, if the patient has noisy ECG data, the processor can provide a notification to the patient to stop any motion during recording of updated ECG data. For example, the processor can be configured to characterize the amount of noise in the frequency domain of the ECG signal based on a normalized scale ranging from 0 to 1. On such a scale, a value of 0 corresponds to substantially minimal noise. For example, during an initial fitting of the device when the device is initially baselined (or, additionally or alternatively, during a subsequent re-baselining period), the patient can be asked to remain still, and the recorded ECG signal can be analyzed for noise content using the frequency domain analysis technique above. In examples, a re-baselining for calibrating the scale can be performed while the patient is asleep (e.g., based on time of date information indicating a time during the night period and/or lack of motion detected via the accelerometers). This initial or re-baselined state can be deemed to be 0 on the normalized scale. Conversely, a value of 1 is deemed to indicate that the ECG channel is too noisy to discern a usable ECG signal as noted in the examples above. A predetermined threshold can be set (e.g., 0.6) to determine if a patient is active or not based on such a scale. The predetermined threshold can be user-configurable via a user interface. For example, the threshold may be set to 0.6 by default, but a prescriber or other authorized person can adjust the threshold (e.g., change from 0.6 to 0.5 or 0.65, or 0.7). Based upon the likelihood that a patient is active (e.g., if the monitored ECG noise value transgresses the predetermined threshold), the processor can then deem the patient as likely being engaged in a high-noise activity.

It should be noted that process 500 as shown in FIG. 5 is shown by way of example only and can be modified based upon implementation of the techniques as taught herein. For example, receiving 504 patient input as shown in process 500 can be an optional step and determination 508 of a high-noise activity can be limited to analysis of the received motion data. It should also be noted that process 500 is shown as initially monitoring a patient using the AIN sensitive arrhythmia processing mode by way of example only. In some examples, the monitoring process can initiate using the AIN robust arrhythmia processing mode and transition to the AIN sensitive arrhythmia processing mode upon determination that a high-noise activity has been completed.

Figure 6A:
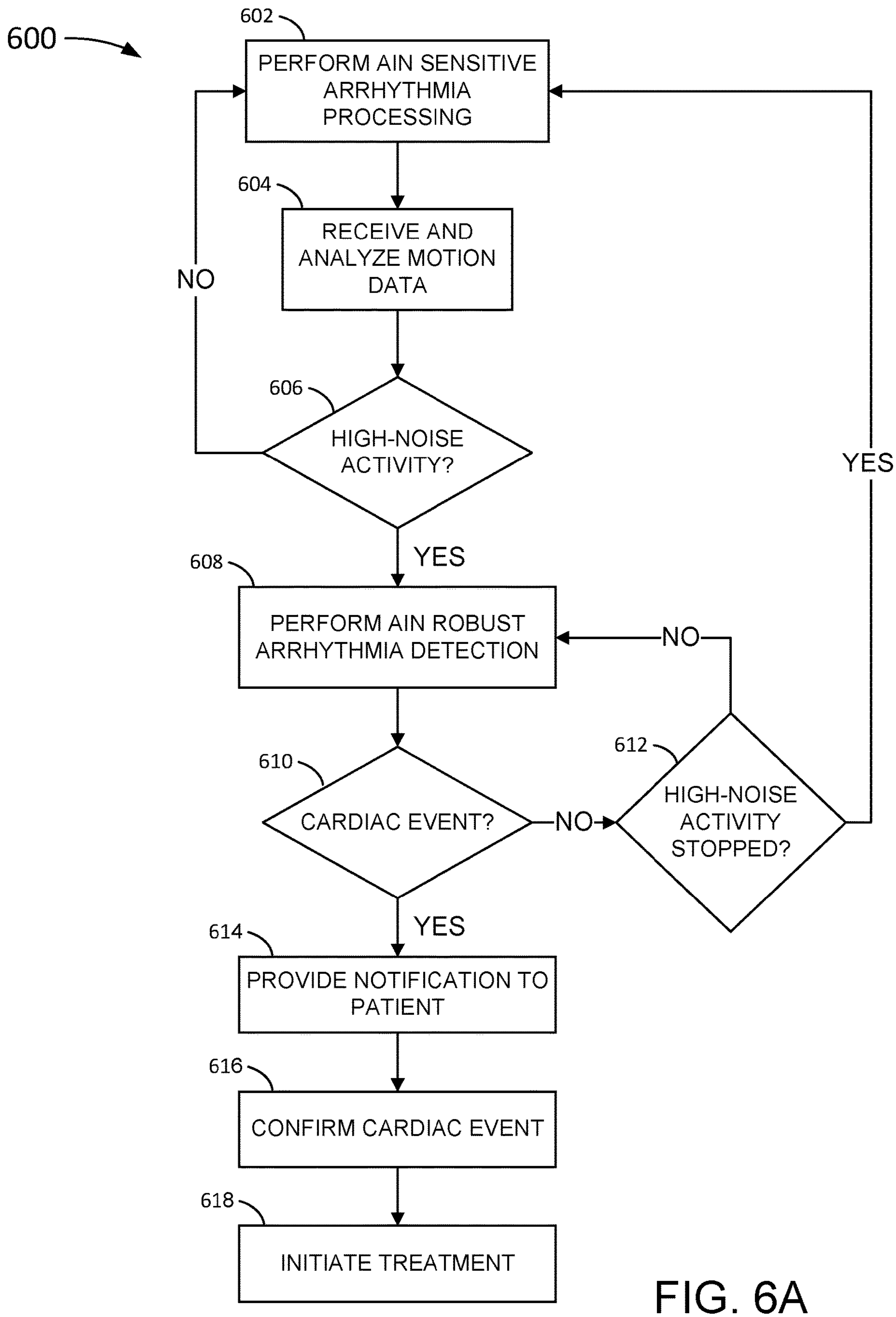
FIG. 6A illustrates a process flow for providing treatment to a patient experiencing an arrhythmia, in accordance with an example of the present disclosure.

FIG. 6A illustrates a process 600 for providing treatment to a patient that may be performing a high-noise activity. Similar to process 500, process 600 can start with the processor performing 602 arrhythmia processing in the AIN sensitive mode. During the processing, the processor can receive and analyze 604 motion data from an accelerometer interface or one or more accelerometers as described herein. Based upon the motion data, the processor can determine 606 if the patient is engaging in a high-noise activity such as walking, running, climbing the stairs, riding a bicycle, and other similar high-noise activities.

Figure 6B:
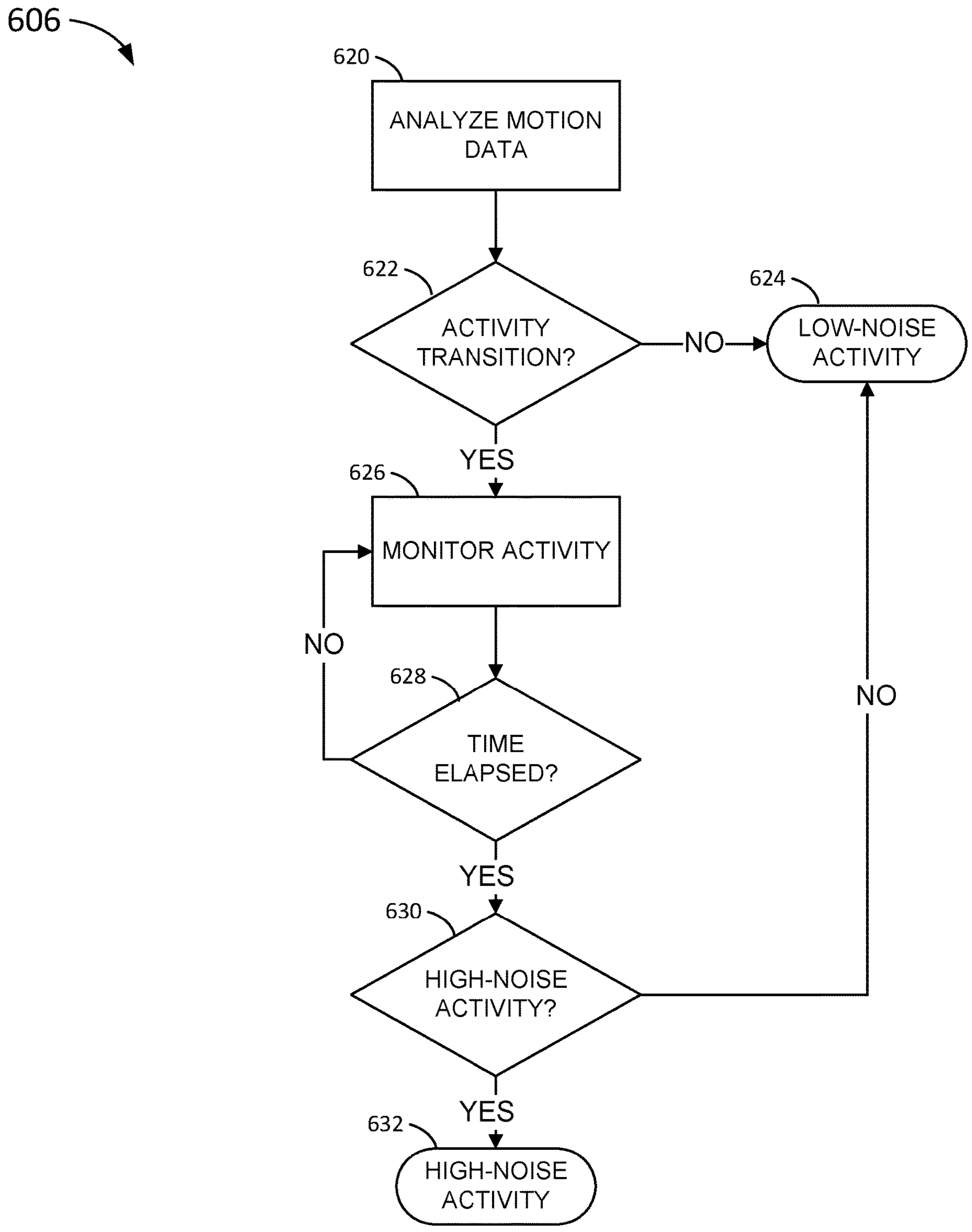
FIGS. 6B and 6C illustrate additional detail of the process flow as shown in FIG. 6A, in accordance with an example of the present disclosure.

FIG. 6B illustrates a more detailed process flow for determining 606 whether a patient is engaging in a high-noise activity. As shown in FIG. 6B, the processor can analyze 620 the received motion data to determine 622 if that patient has transitioned between activities. For example, the processor can store an indicator in memory of the current activity that the patient is engaged in. If the patient is sitting or otherwise stationary, the process can store an indicator in memory that indicates the patient is stationary or otherwise engaged in a low-noise activity. The processor can continue to analyze 620 the motion data until the processor determines 622 that there is a transition between activities. If the transition is from a first low-noise activity to another low-noise activity (e.g., transitioning from sitting to laying down), the processor can store an indication in memory that the patient is still engaged in a low-noise activity and return 624 an indication that the patient is engaged in a low-noise activity as an output of determination 606 as shown in FIG. 6A. However, if the processor determines 622 that the patient has transitioned from a low-noise activity to a potentially high-noise activity, the processor can monitor 626 the activity of the patient and, in certain implementations, initiate a transition timer. For example, the processor can use the transition timer to indicate that the high-noise activity is potentially a prolonged activity that may result in changing the operating or monitoring mode of the medical device as described herein.

As further shown in FIG. 6B, the processor can determine 628 if the transition timer has elapsed. For example, the transition timer can be set to measure a particular transition period that can be set to a default value or to a value selected by a physician or other similar medical professional when setting up a wearable medical device for a patient as described herein. In some examples, the transition period can be set by a technician or other caregiver helping the patient with the medical device. In certain implementations, the transition timer can have a default period of 15 seconds. In other examples, the transition timer can be set to a period of time from about 10 seconds to about 30 seconds.

If the processor determines 628 that the timer has not elapsed, the processor can continue to monitor 626 the patient's activity. If the processor does determine 628 that the timer has elapsed, the processor can determine 630 if the patient has continued to perform the high-noise activity. If the processor determines that the patient has not continued to perform the high-noise activity after the expiration of the transition timer, the processor can return 624 an indication that the patient is engaged in a low-noise activity as the output of determination 606 as shown in FIG. 6A. If the processor does determine 630 that the patient has continued to perform the high-noise activity after expiration of the transition timer, the timer can write an indication to the memory that the patient is engaged in a high-noise activity (e.g., including an activity classification/type such as walking, running, climbing stairs if available) and return 632 an indication that the patient is engaged in a high-noise activity as the output of determination 606 as shown in FIG. 6A.

It should be noted that the expanded description of determining 606 a high-noise activity as shown in FIG. 6B is provided by way of example only and can be modified and/or altered based upon the implementation of the motion identification and classification techniques as described herein.

Referring back to FIG. 6A, if the processor does not determine 606 that the patient is engaging in a high-noise activity, the processor can continue to perform 602 arrhythmia processing in the AIN sensitive mode. However, if the processor does determine 606 that the patient is engaging in a high-noise activity, the processor can perform 608 AIN robust mode arrhythmia detection, such as heart rate based arrhythmia detection.

As further shown in FIG. 6A, the processor can determine 610 if the patient is experiencing a cardiac event while performing the heart rate based arrhythmia processing. For example, the processor can monitor the patient's heart rate to determine if the patient's heart rate has exceeded one of 100 bpm, 110 bpm, 120 bpm, 130 bpm, 140 bpm, 150 bpm, and other similar heart rate thresholds. Based upon the patient's current heart rate, if the processor does not determine 610 that the patient is experiencing a cardiac event, the processor can determine 612 if the patient has stopped performing the high-noise activity.

Figure 6C:
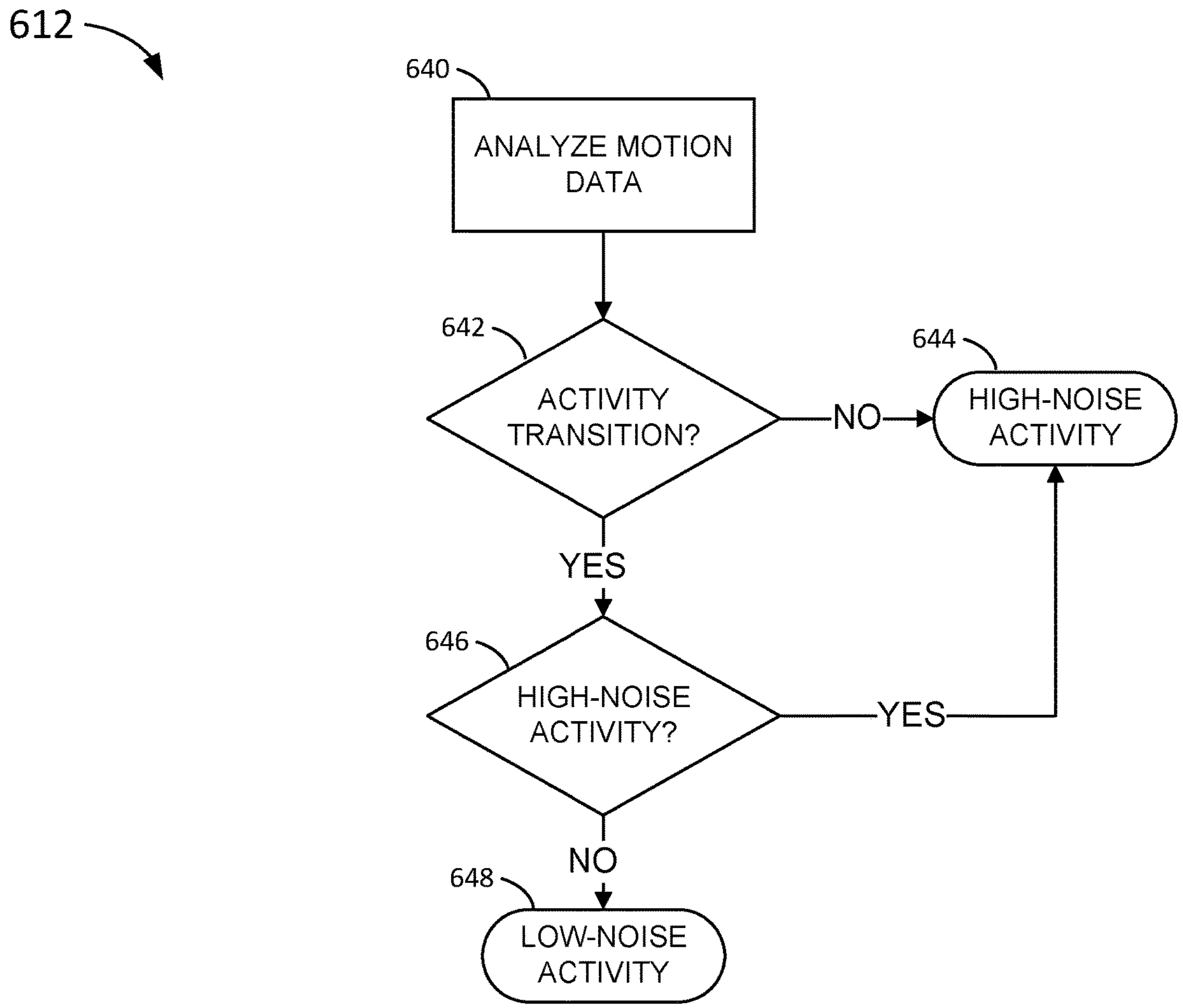

FIG. 6C illustrates a more detailed process flow for determining 612 whether a patient has stopped a high-noise activity. As shown in FIG. 6C, the processor can analyze 640 the received motion data to determine 642 if that patient has transitioned between activities. For example, if the processor determines 642 that there has been no transition from the high-noise activity, the processor can return 644 an indication that the patient is still engaged in the high-noise activity as the output of determination 612 as shown in FIG. 6A.

However, if the processor determines 642 that the patient has transitioned between activities, the processor can further determine 646 whether the new activity is a high-noise activity. If the processor determines 646 that the patient has transitioned from a high-noise activity to a low-noise activity, the processor can return 648 an indication that the patient is currently engaged in a low-noise activity as the output of determination 612 as shown in FIG. 6A. Conversely, if the processor determines 646 that the patient has transitioned from a first high-noise activity to a second high-noise activity (e.g., transitioned from walking to climbing stairs), the processor can return 644 an indication that the patient is currently engaged in a high-noise activity as the output of determination 612 as shown in FIG. 6A.

It should be noted that the expanded description of determining 612 whether high-noise activity has stopped as shown in FIG. 6C is provided by way of example only and can be modified and/or altered based upon the implementation of the motion identification and classification techniques as described herein. For example, the expanded description of determining 612 can include a transition timer similar to that as described above in the description of FIG. 6B when the processor is determining 642 whether the patient has transitioned between activities.

Referring back to FIG. 6A, if the processor does determine that the patient has stopped performing the high-noise activity, the processor can resume performing 602 the AIN sensitive arrhythmia processing. If the processor determines 612 that the patient has not stopped the high-noise activity, the processor can continue to perform 608 the AIN robust mode arrhythmia detection.

As further shown in FIG. 6A, if the processor does determine 610 that the patient is experiencing a cardiac event, the processor can provide 614 a notification to the patient to stop all physical activity. In certain implementations, the notification can include an audible alert, a text output on a user interface of the medical device, a vibrational or other similar tactile alert, a flashing visual alert, and combinations of these alerts.

Once the user has stopped the physical activity, or after expiration of a period of time after the notification, the processor can confirm 616 the cardiac event using, for example, the default and full arrhythmia processing. Based upon the AIN sensitive mode ECG processing results, the processor can initiate 618 treatment of the patient. In some examples, the processor can be configured to provide an arrhythmia alert to the patient and receive input from the patient indicating that the arrhythmia alert was a false alert during confirmation. In such an example, the processor can be further configured to prompt the patient to indicate an activity being performed during the arrhythmia alert. The patient's response to such a prompt can be used to evaluate against the relevant motion data. In an example, the false alert information and associated motion data can be used to further train the machine learning classifier to better identify the patient activity in the future.

It should be noted that process 600 as shown in FIG. 6A is shown by way of example only and can be modified based upon implementation of the techniques as taught herein. For example, the processor can be configured to prompt the patient during the high-noise activity to confirm that they are engaged in a physical activity such as walking or running.

In general, the QRS wave or complex has a QRS width that is between 0.06-0.12 seconds (60 ms to 120 ms), where in certain scenarios, a normal range is considered to be between 0.08-0.12 seconds (80 ms to 120 ms). In children and during physical activity, the QRS width may be shorter than the general width. Depolarization of the heart ventricles occurs almost simultaneously, via the bundle of His and Purkinje fibers. Any abnormality of conduction takes longer and causes widened QRS complexes. In example implementations, in the AIN robust mode, QRS complex including QRS width detection can be based on a modified Pan-Tompkins method, where the modification is implemented in selecting thresholds and signal noise values to reflect the high noise quality of the AIN. In example implementations herein, the QRS complex can be determined based on the modified Pan-Tompkins method as follows. A series of filters can be applied to the received ECG signal to highlight the frequency content of the rapid heart depolarization and remove background noise. Then, the processor can square the ECG signal to amplify the QRS contribution. Finally, the processor applies adaptive thresholds to detect the peaks of the filtered signal. For a signal sampled at a frequency of 200 Hz, filters with the following transfer functions can be used:

$$H(z) = \frac{(1 - z^{-6})^2}{(1 - z^{-1})^2}$$

$$H(z) = \frac{(-1/32 + z^{-16} - z^{-17} + z^{-32}/32)}{(1 - z^{-1})}$$

A derivative filter can be applied to provide information about the slope of the QRS. For a signal sampled at 200 Hz, the following transfer function can be applied:

$$H(z) = 0.1(-2z^{-2} - z^{-1} + z^{1} + 2z^{2})$$

The filtered signal is squared to enhance the dominant peaks (QRSs) and reduce the possibility of erroneously recognizing a T wave as an R peak. Then, a moving average filter is applied to provide information about the duration of the QRS complex. The number of samples to average is chosen in order to average on windows of 150 ms. The resulting signal is the integrated signal. In order to detect a QRS complex, the local peaks of the integrated signal are found. A peak can be identified as the point in which the signal changes direction (e.g., from an increasing direction to a decreasing direction). After each peak, the processor can be configured such that no peak is to be detected in the next 200 ms (e.g., a lockout time period). In examples, this is a physiological constraint due to the refractory period during which ventricular depolarization cannot occur even in the presence of a stimulus. Each fiducial mark is considered as a potential QRS. To reduce the possibility of wrongly selecting a noise peak as a QRS, each peak amplitude is compared to a threshold ($\text{Threshold}_I$) that takes into account the available information about already detected QRS and the AIN type noise level:

$$\text{Threshold}_I = \text{NoiseLevel}_I + 0.25(\text{SignalLevel}_I - \text{NoiseLevel}_I)$$

where $\text{NoiseLevel}_I$ is the running estimate of the AIN type noise level in the integrated signal and $\text{SignalLevel}_I$ is the running estimate of the signal level in the integrated signal.

The threshold is automatically updated after detecting a new peak, based on its classification as signal or AIN type noise peak:

$$\text{SignalLevel}_I = 0.125\text{PEAK}_I + 0.875\text{SignalLevel}_I (\text{if PEAK}_I \text{ is a signal peak})$$

$$\text{NoiseLevel}_I = 0.125\text{PEAK}_I + 0.875\text{NoiseLevel}_I (\text{if PEAK}_I \text{ is a noise peak})$$

where $\text{PEAK}_I$ is the new peak found in the integrated signal.

At the beginning of the QRS detection, a 2 second learning phase is needed to initialize $\text{SignalLevel}_I$ and $\text{NoiseLevel}_I$ as a percentage of the maximum and average amplitude of the integrated signal, respectively.

If a new $\text{PEAK}_I$ is under the $\text{Threshold}_I$, the AIN type noise level is updated. If $\text{PEAK}_I$ is above the $\text{Threshold}_I$, the algorithm implements a further check before confirming the peak as a true QRS, taking into consideration the information provided by the bandpass filtered signal.

In the filtered signal the peak corresponding to the one evaluated on the integrated signal is searched and compared with a threshold, calculated in a similar way to the previous step:

$$\text{Threshold}_F = \text{NoiseLevel}_F + 0.25(\text{SignalLevel}_F - \text{NoiseLevel}_F)$$

$$\text{SignalLevel}_F = 0.125\text{PEAK}_F + 0.875\text{SignalLevel}_F (\text{if PEAK}_F \text{ is a signal peak})$$

$$\text{NoiseLevel}_F = 0.125\text{PEAK}_F + 0.875\text{NoiseLevel}_F (\text{if PEAK}_F \text{ is a noise peak})$$

where the final F stands for filtered signal.

Once the QRS complex is successfully recognized, the heart rate for use in the AIN robust mode is computed as a function of the distance in seconds between two consecutive QRS complexes (or R peaks):

$$HR[bpm] = \frac{60}{RR[s]}$$

where bpm stands for beats per minute.

In examples, in the AIN robust mode, along with the peak, the processor can measure a width of the peak waves as the QRS width. In implementations, a threshold width can be based on determining over the course of a predetermined number of QRS complexes (e.g., 5 to 10 QRS complexes, user configurable), an average width that exceeds a predetermined QRS width threshold. For example, the pre-configured QRS width threshold may be set to be 120 ms. A caregiver or other authorized person may, via a user interface configure a QRS width threshold parameter to be set to a value in a range from 100 ms to 180 ms.

In examples, in the AIN robust mode, the processor can measure peak amplitudes to determine the average R wave amplitude. An increased R wave amplitude can indicate cardiac hypertrophy. In implementations, a threshold R wave amplitude can be determined over the course of a predetermined number of QRS complexes (e.g., 5 to 10 QRS complexes, user configurable), an average value that exceeds a predetermined R wave amplitude threshold. For example, in one configuration, depending on the average ECG signal voltage ranges, the pre-configured R wave amplitude threshold may be set to be 1.5 mV. A caregiver or other authorized person may, via a user interface configure a R wave amplitude threshold parameter to be set to a value in a range from 1 mV to 5 mV.

The T wave represents the repolarization of the ventricles. Abnormalities of the ST segment and T wave represent the abnormalities of the ventricular repolarization or secondary abnormalities in ventricular depolarization. In examples, in the AIN robust mode, the processor can measure T wave amplitudes over multiple ECG cycles to determine the average T wave amplitude and direction. In implementations, the processor can be configured to determine whether the T wave deflection is in a same direction as the QRS complex in at least one or more ECG channels. An increased T wave amplitude can indicate cardiac abnormalities that warrant further examination. In implementations, a threshold T wave amplitude can be determined over the course of a predetermined number of ECG cycles (e.g., 5 to 10 ECG cycles, user configurable), an average value that exceeds a predetermined T wave amplitude threshold. For example, in one configuration, depending on the average ECG signal voltage ranges, the pre-configured T wave amplitude threshold may be set to be 1 mV. A caregiver or other authorized person may, via a user interface configure a T wave amplitude threshold parameter to be set to a value in a range from 0.1 mV to 1 mV.

As noted above, one object of activity recognition can be to apply a label to a patient at any point in time, the label indicating whether the patient was engaged in a physical activity at the time and, if possible, what type of activity was the patient participating in. To recognize or identify an activity, a process can include dividing an input series into overlapping time periods to which labels can be applied. For example, the overlapping time periods can include five to ten second ranges with 50% overlap between adjacent time periods. Based upon the overlapping portions, common features can be extracted and analyzed to determine activity type. For example, features can include acceleration mean, standard deviation of acceleration between time periods, derivatives of acceleration (including, for example, velocity, acceleration, jerking motions), energy in fast Fourier transform frequency bands, wavelet coefficients, and angle correlation. Based upon analysis of these features over time, a type of activity can be determined from accelerometer data.

One technique for determining the type of activity is using supervised machine learning. As described herein, supervised machine learning techniques are used to derive classifiers that can be used to correctly, or highly accurately, label patient activity as described herein. Supervised machine learning relies on the idea that a high percentage of the time points to be classified are assigned the correct label during the learning process. For example, depending upon the type of machine learning technique used, a training set can include 95% of the time points having the correct label during the learning process. In other examples, the training set can include 90%-100% of the time points having the correct label. Thus, as described herein, in order to accurately train a motion classifier as described herein, a high percentage of the training data (e.g., accelerometer data) should be accurately labeled with the corresponding physical activity information.

To create a training data set, activity information including accelerometer data and label information can be collected or otherwise obtained from a trusted source. If the activity data is collected for a group of patients, the information can also include additional data such as patient medical history information and patient classification information such as demographic information.

Figure 7A:
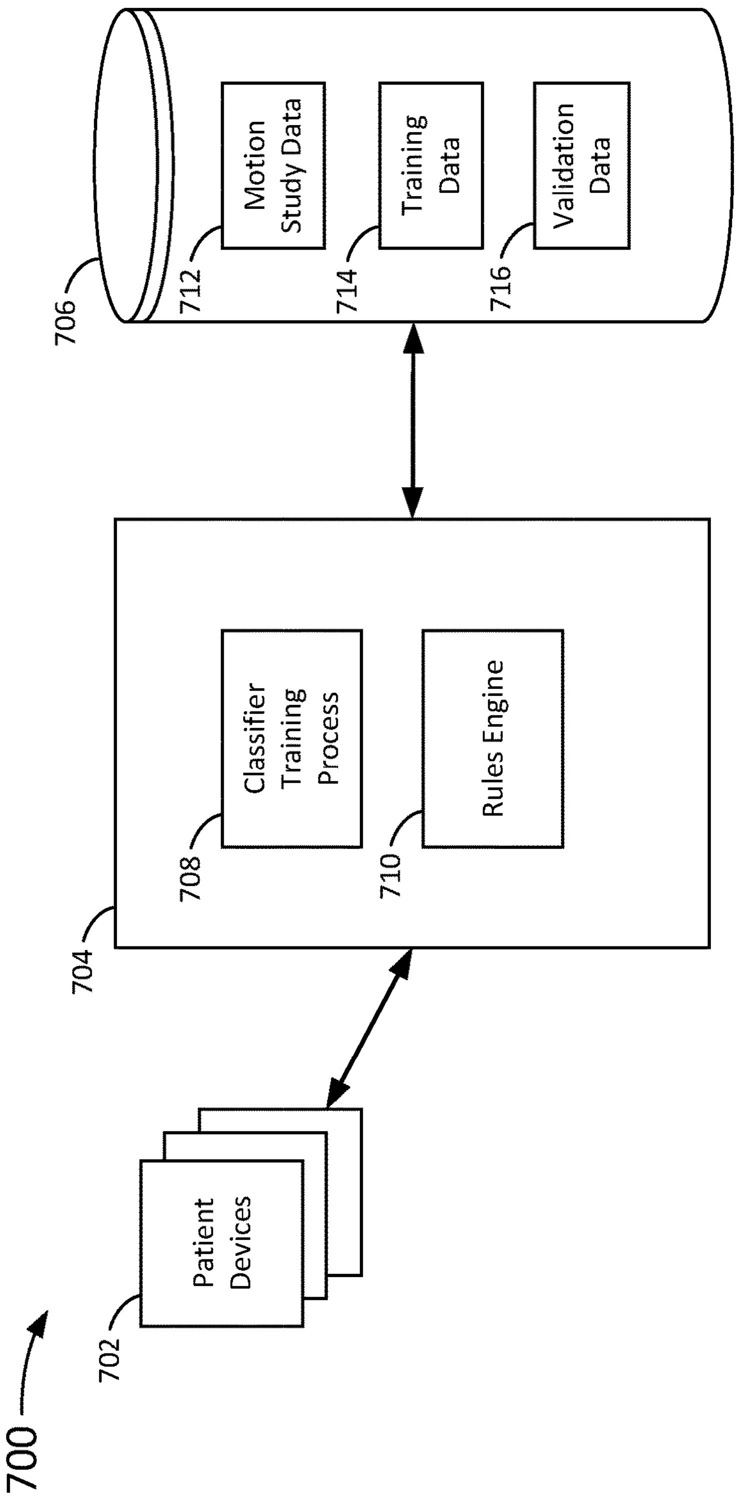
FIGS. 7A and 7B illustrate a schematic views of a system for training a classifier, in accordance with an example of the present disclosure.

FIG. 7A illustrates a sample overview of a distributed system 700 for training a motion classifier as described herein. As shown in FIG. 7, a set of patient devices can be operably coupled to a remote computing device 704. The remote computing device can be operably connected to a data repository 706 that is configured to store various information. As further shown in FIG. 7, the remote computing device can include a classifier training process 708 and a rules engine 710. As described herein, the classifier training processor 708 can be configured to generate a motion classifier based upon a set of training data and any rules for the classifier as defined in the rules engine 710. For example, the rules engine 710 can include a set of relational rules that can be defined during the classifier training process to collectively represent the knowledge of the classifier training processor 708. Once defined, the set of relational rules can be combined into one or more classifier models. For example, to generate the training data, the data repository 706 can include a set of motion study data 712. As described above, the motion study data 712 can include time-based accelerometer data for various physical activities as well as activity label information for the accelerometer data. In certain implementations, the motion study data can also include accelerometer location information defining where on a person's body the accelerometers were positioned when collecting the motion data. The data repository can also include a set of training data 714 generated from the motion study data 712 and a set of validation data also generated from the motion study data. The training data 714 can be used by the remote computer 704 to train the motion classifier using the classifier training process 708. After training, the remote computer 704 can use the validation data 716 to gauge the sensitivity and specificity of the generated motion classifier. The motion classifier can then be pushed to one or more patient devices 702 for use in classifying patient motion as described below. Examples of implementing the motion classifier to identify patient activity type is described below in the discussion of FIGS. 9A and 9B.

Figure 7B:
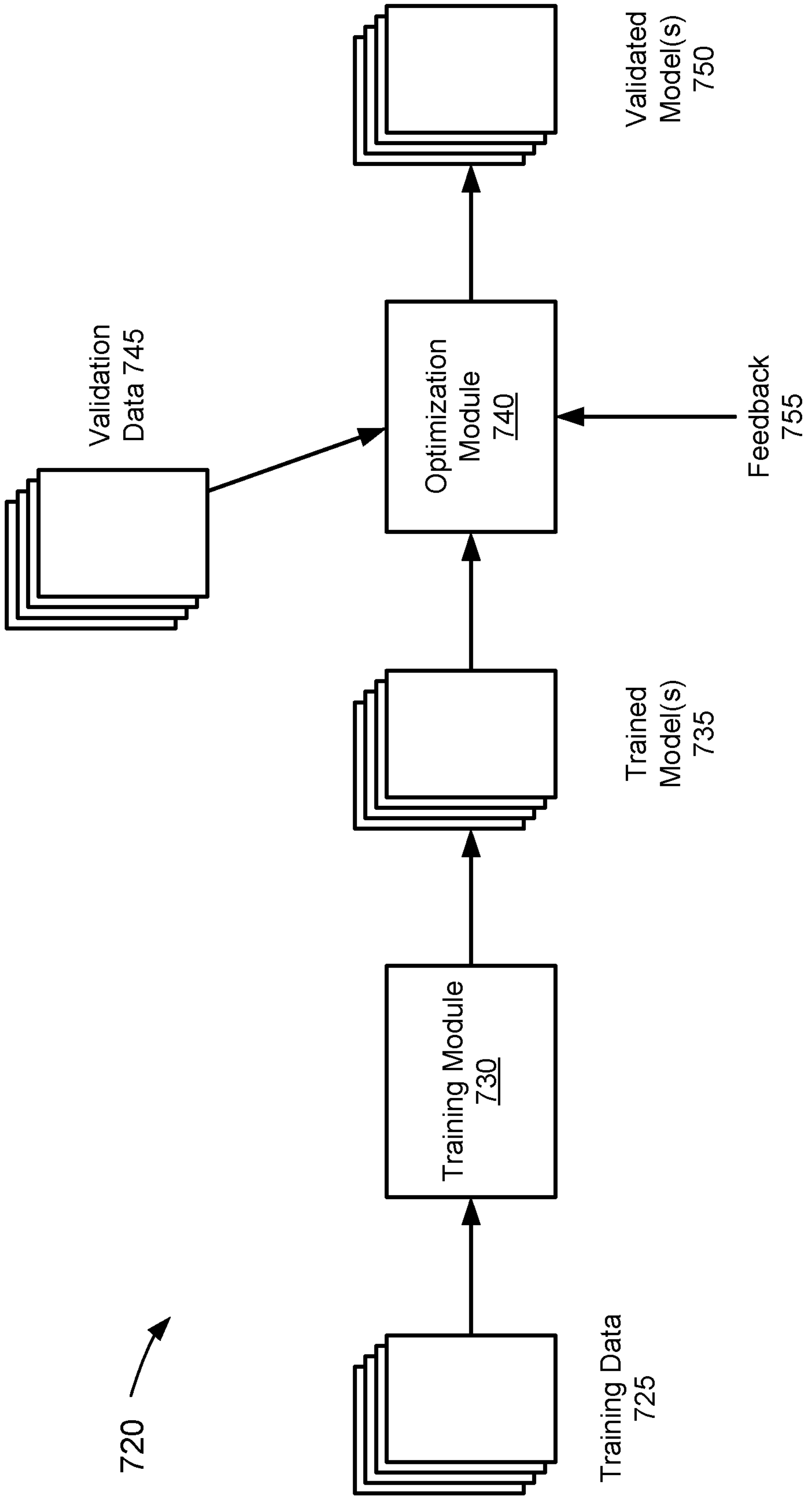

FIG. 7B illustrates a sample process 720 for training and validating one or more motion classification models for a supervised machine learning process as described above. A set or population of known records (e.g., motion study data 712) can be provided as the data set used to train and validate the classification models. For example, the training data can include training variables extracted from data such as raw accelerometer signals contained within the motion study data 712 as described above and any associated label information related to physical activity labels associated with the raw accelerometer signals.

The training data set 725 can be fed into a training module 730. The training module 730 can include one or more untrained data structures such as a series of data trees (e.g., organized using a random forest tool). Using the known input variables and known outcomes from the training data set 725, the training module 730 can iteratively process each data point in the training set, thereby training the data structures to more accurately produce the expected (and known) outcomes.

Once the training module 730 has exhausted the training data set 725, the training module can output one or more trained classifier models 735. The one or more trained classifier models 735 can represent a set of models that provide the most accurate classification and generation of an outcome for a known set of input variables that could be generated from the training data set 725. An optimization module 740 can be configured to further refine the trained classifier models 735 using additional known records. For example, a validation data set 745 can be input into the optimization module 740 for further optimization of the one or more trained classifier or regression models 735.

As shown in FIG. 7B, the optimization module 740 can process the validation data set 745 to optimize the trained classifier models 735 by, for example, refining thresholds, tuning learning parameters (e.g., learning rate and regularization constant information), and other similar optimization processes. The optimization module 740 can produce one or more validated classifier models 750. Depending upon the intended purpose of the validated classifier models 750, the models can have certain classifier parameters (e.g., a certain specificity and/or sensitivity).

As the validated classifier models 750 are used to classify or provide output values for patient motion data (e.g., to produce new outputs for a set of patient motion as described herein), the produced outcomes can be used to better validate the process using a closed loop feedback system. For example, as a patient's motion is classified, the classified motion can be verified by, for example, the patient. The patient's record, now updated to include a known outcome of patient motion, can then be provided as feedback 755 to the optimization module 740. The validation module can process the feedback 755, comparing a generated output against the known outcome for the patient's classified motion. Based upon this comparison, the optimization module 740 can further refine the validated classifier models 750, thereby providing a closed loop system where the models are updated and upgraded regularly. It should be noted that, in process 720 as shown in FIG. 7B, the feedback is shown as being provided to the optimization module 740 by way of example only. In some examples, the feedback 755 can be sued to supplement or add to the training data 725 as well to provide for personalization of the classifier models 750 to an individual patient or a specific patient population.

Figure 7C:
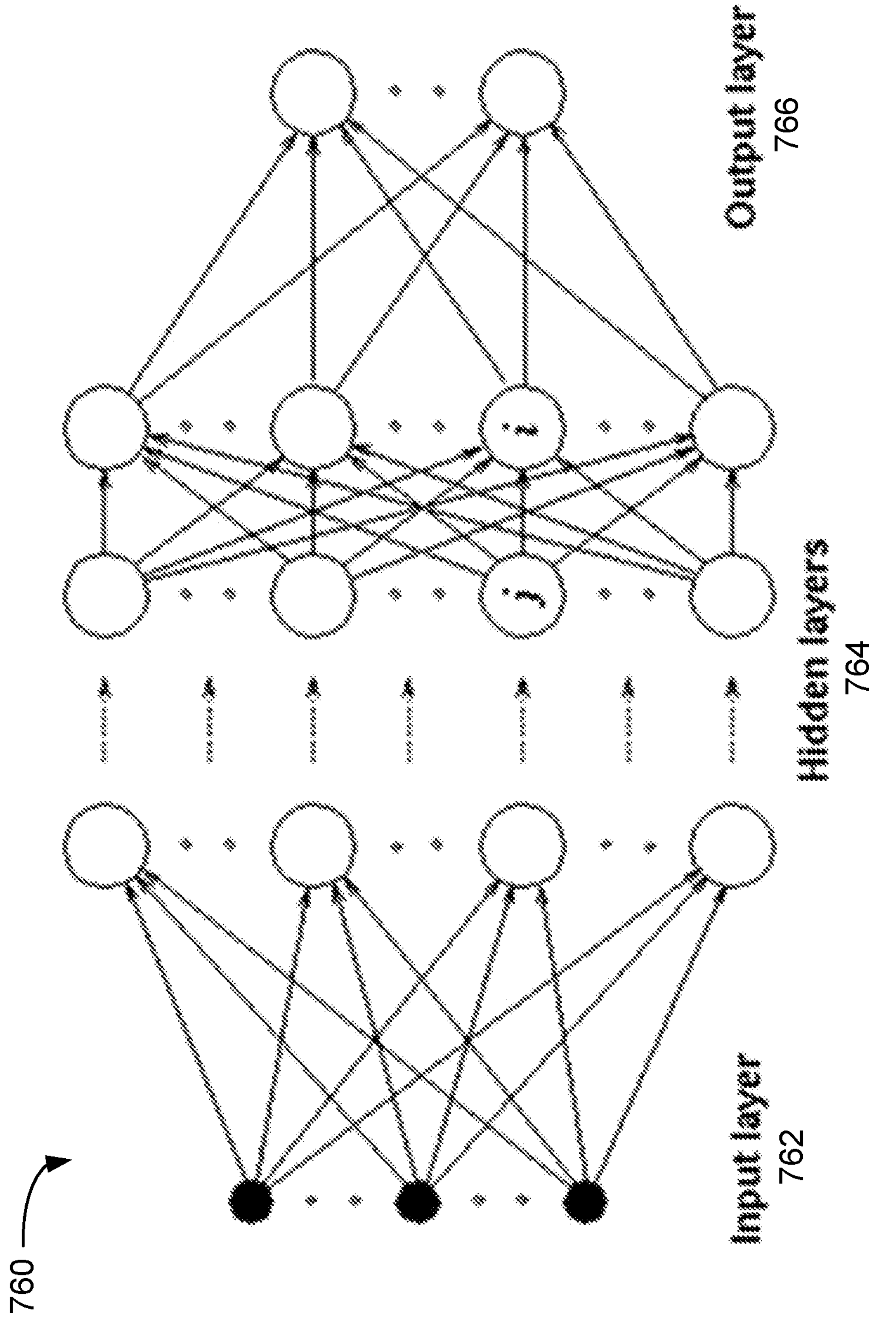
FIG. 7C illustrates an overview of a sample artificial neural network, in accordance with an example of the present disclosure.

In a specific example, a process such as the motion classifier model as described herein can be implemented as a network of nodes interconnected to form an artificial neural network. For example, FIG. 7C illustrates a topography for a sample artificial neural network 760. The artificial neural network 760 can include, for example, one or more nodes organized into an input layer 762, a series of hidden layers 764, and one or more nodes organized into an output layer 766.

In an artificial neural network, the nodes include a plurality of artificial neurons, each artificial neuron having at least one input with an associated weight. The artificial neural network parameters (e.g., weights) can be trained by the inputting of different sets of patient physiological data from the training data and comparing the network output with a ground truth output from the training data. The training process can modify the network parameters to minimize the difference between the network output and the ground truth output. This results in the artificial neural network being trained to produce a patient condition classification.

An artificial neural network may be a mathematical or computational model that can compute a wide variety of functions and are inspired by the structure and/or functional aspects of a biological neural network. In embodiments, the nodes of the artificial neural network include at least one input, at least one neuron and at least one output. The neuron may be present in a single hidden layer of the artificial neural network and may take two or more inputs. In examples where the artificial neural network has a plurality of neurons, the plurality of neurons may be distributed across one or more hidden layers. Where there is more than one layer, each layer may be interconnected with a previous and a subsequent layer.

The artificial neural network may be an adaptive system, where it changes based on external or internal information that flows through the artificial neural network during the training or learning phase. Specifically, the weight (or strength) of the connections (such as between adjacent artificial neurons, or between an input and an artificial neuron) within the artificial neural network is adapted to change to match the known outputs.

As noted above, once the motion classifier has been trained and verified, it can be pushed to another device such as a patient's wearable medical device or a gateway device in communication with a patient's wearable medical device for analysis and classification of a patient's movement. As used herein, a gateway device refers to a separate computing device operably connected to the patient's wearable medical device. For example, a gateway device can include a personal computer, a tablet computing device, a smartphone, a base station associated with the wearable medical device that includes, for example, a battery charger and network communication circuitry, and other similar computing devices. In other examples, the processing could also be performed on a remotely located device such as a server or multiple servers arranged in, for example, a cloud computing environment.

Figure 8A:
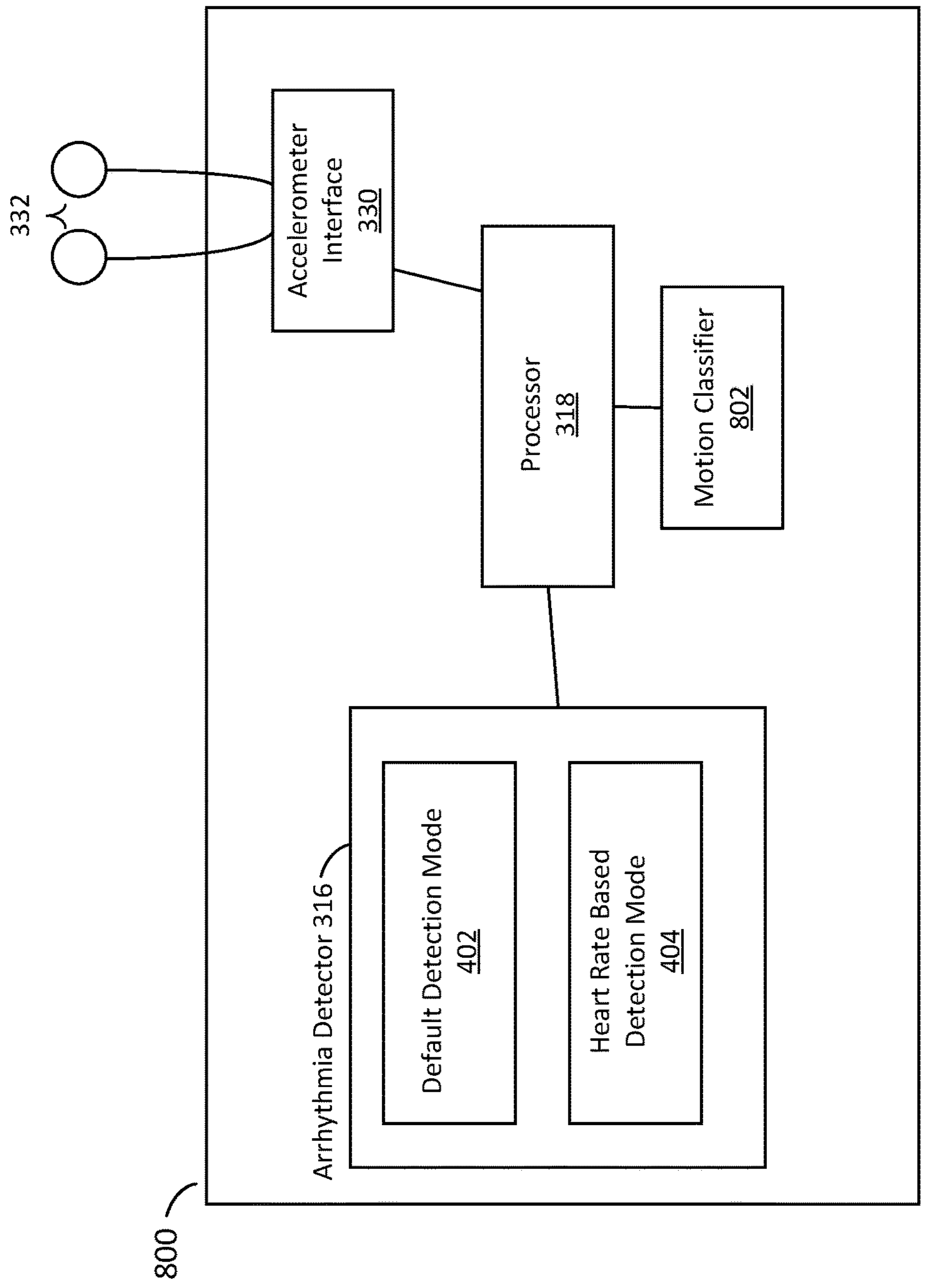
FIG. 8A illustrates a schematic view of a sample controller including an integrated motion classifier, in accordance with an example of the present disclosure.

FIG. 8A illustrates a sample medical device controller 800 that includes a local motion classifier 802. Additionally, similar to medical device controller 300 as described above, controller 800 includes a processor 318 operably configured to interact with the motion classifier 802, an arrhythmia detector 316 configured to perform both an AIN sensitive mode 402 and an AIN robust mode 404 as described above, an accelerometer interface 330, and a set of accelerometers 332.

Figure 8B:
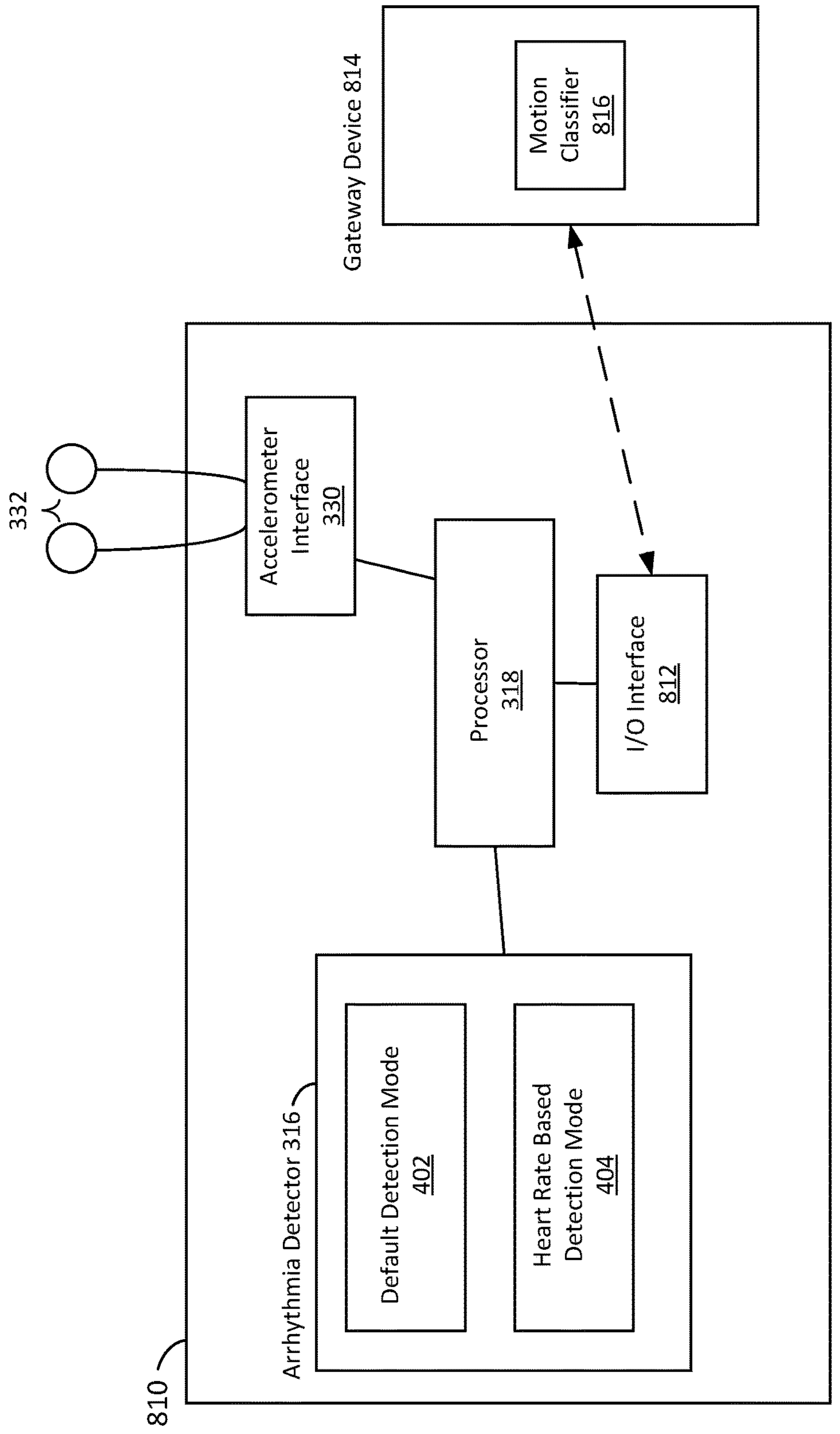
FIG. 8B illustrates a schematic view of a sample controller in communication with a gateway device including an integrated motion classifier, in accordance with an example of the present disclosure.

FIG. 8B illustrates a sample medical device controller 810. As shown in FIG. 8B, the controller 810 includes an input-output interface 812 that is configured to operably couple to and communication with a gateway device 814. The controller 810 includes a processor 318 operably coupled to and configured to communicate with the I/O interface 812, an arrhythmia detector 316 configured to perform both an AIN sensitive mode 402 and an AIN robust mode 404 as described above, an accelerometer interface 330, and a set of accelerometers 332.

As further shown in FIG. 8B, the gateway device includes a motion classifier 816 as described herein. The processor 318 can be configured to transmit motion data received from the accelerometer interface 330 to the gateway device 814 for classification using the motion classifier 816. The processor 318 can be further configured to receive motion classification information from the gateway device 814.

Figure 9A:
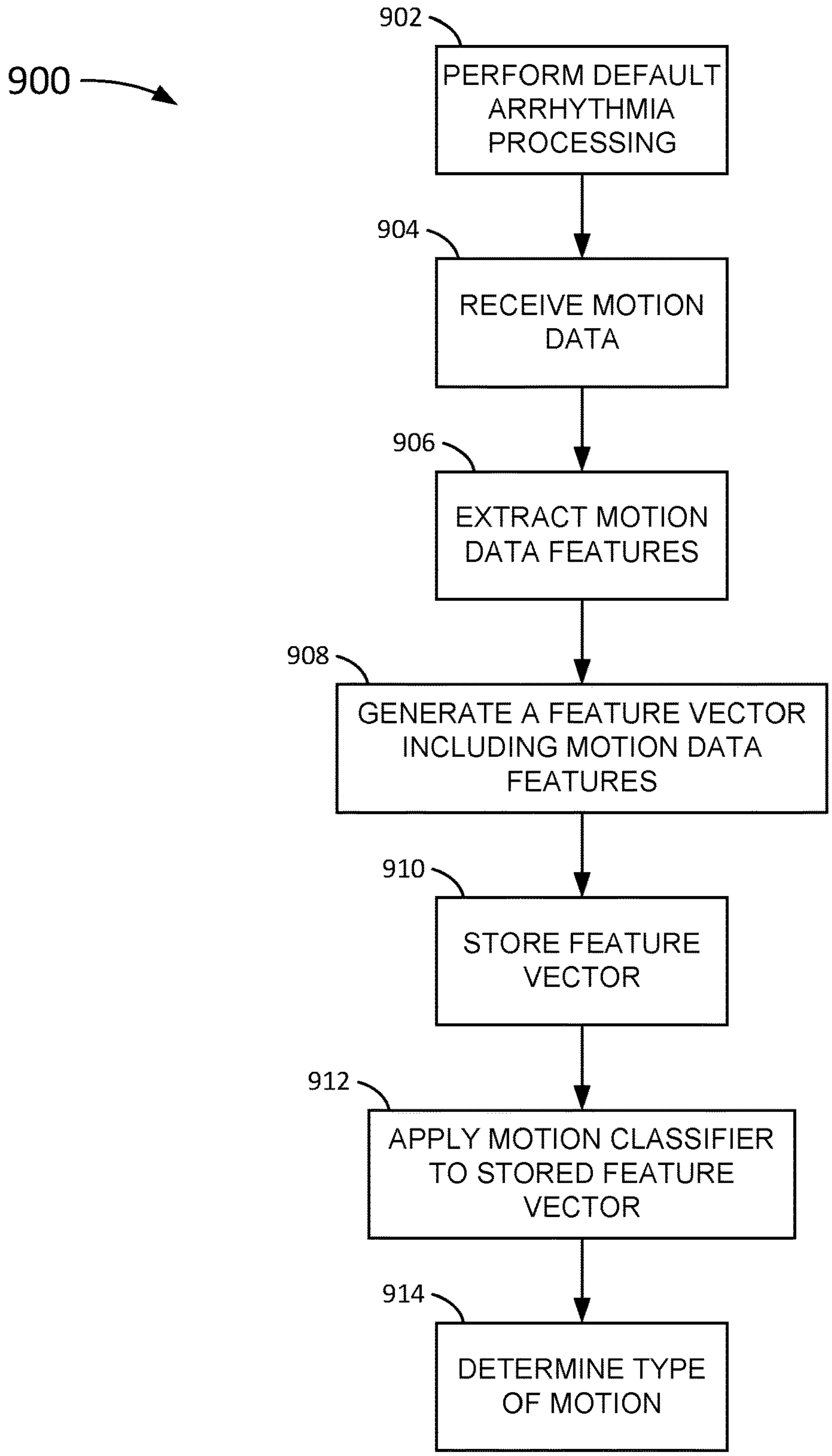
FIGS. 9A and 9B illustrate process flows for determining motion type using a motion classifier, in accordance with examples of the present disclosure.

FIG. 9A illustrates a sample process 900 for using a motion classifier as described herein to determine what activity a patient is currently engaged in. For example, the process 900 as described herein can be implemented by processor 318 as included in either controller 800 and controller 810 as described above.

As shown in FIG. 9A, process 900 can include a processor performing 902 arrhythmia processing in AIN sensitive mode. During processing, the processor can receive 904 motion data from, for example, an accelerometer interface such as accelerometer interface 330. The processor can extract 906 one or more motion data features from the motion data. For example, the motion data features can include values for accelerometer outputs such as pitch and roll outputs and outputs representing acceleration values in the x-axis, the y-axis, and the z-axis as described herein. The processor can generate 908*a* feature vector including the motion data features extracted from the motion data. As used herein, a feature vector can include a numerical string of values that represent the motion data features extracted from the motion data.

In some examples, extracting 906 one or more motion data features from the motion data can including calculating one or more an entropy of the motion data, a mean of the motion data, a standard deviation of the motion data, energy within one or more frequency bands of the motion data, one or more wavelet coefficients of the motion data, one or more correlations between directional components within the motion data, angles between consecutive motion signals of the motion data, jerk of the motion data, slippage of the motion data, and other similar motion data features.

As further shown in FIG. 9A, the processor can store 910 the feature vector on a local memory operably coupled to the processor. The processor can also apply 912 the motion classifier to the stored feature vector. For example, applying 912 the motion classifier can include inputting each piece of data stored on the feature vector into the motion classifier and running the motion classifier. In certain implementations, the motion classifier can include an artificial neural network based motion classifier. Upon completion of the motion classifier, the processor can receive the output of the motion classifier and determine 914 what type of motion is represented by the received motion data. For example, based upon the motion classification, the processor can determine 914 that the patient is performing one or a walking activity and a running activity. Based upon the classification of the patient motion, the processor can suspend providing an arrhythmia alert to the patient for a predetermined period of time including, for example, 30 seconds, one minute, two minutes, five minutes, ten minutes, 15 minutes, 20 minutes, and 30 minutes. Similarly, the processor can suspend providing an alert to the patient if the patient is performing a particular activity such as walking, and the patient has noisy ECG data as described above.

In some examples, the classification as determined by the motion classifier can include a confidence metric. The confidence metric can be, for example, a number on a scale that is indicative of how likely the output of the motion classifier is correct. For example, the confidence metric can be on a scale of 0.0 to 1.0, wherein 0.0 is no confidence and 1.0 is complete confidence. In some examples, a classification can include multiple confidence metrics. For example, the motion classifier can include a set of confidence metrics in a single motion classification indicating whether the patient is walking, running, or climbing the stairs.

Figure 9B:
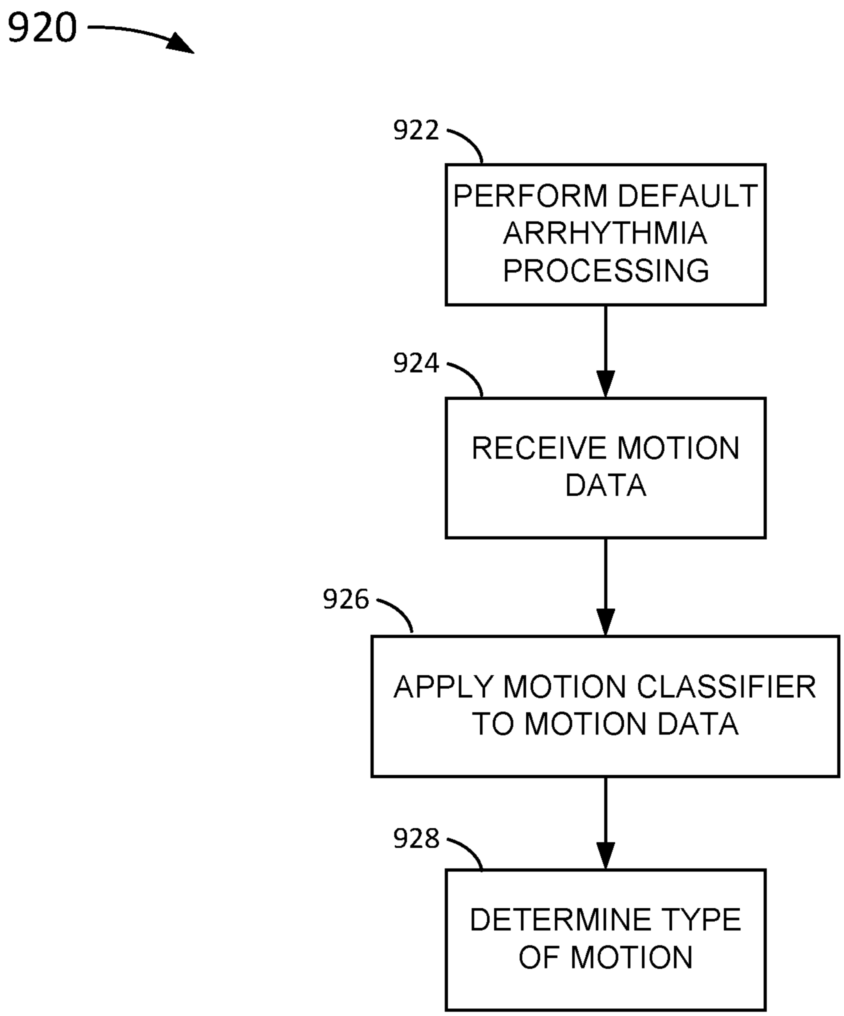

It should be noted that processing the motion data from the accelerometers and extracting motion data features is shown by way of an example only. Depending upon the training of the motion classifier, the motion classifier can be configured to interpret output data as received directly from one or more accelerometers. For example, as shown in FIG. 9B, process 920 includes inputting data directly from the accelerometers to the motion classifier without any preprocessing or feature extraction. As shown, process 920 includes the processor performing 922 arrhythmia processing in AIN sensitive mode as in process 900. During arrhythmia processing, the processor can receive motion data 924. However, rather than process and extract features from the motion data as described above, the processor can apply 926 the motion classifier to the motion data by inputting the motion data directly into the motion classifier. As before, based upon the output of the motion classifier, the processor can determine 928 the type of patient motion.

Figure 10A:
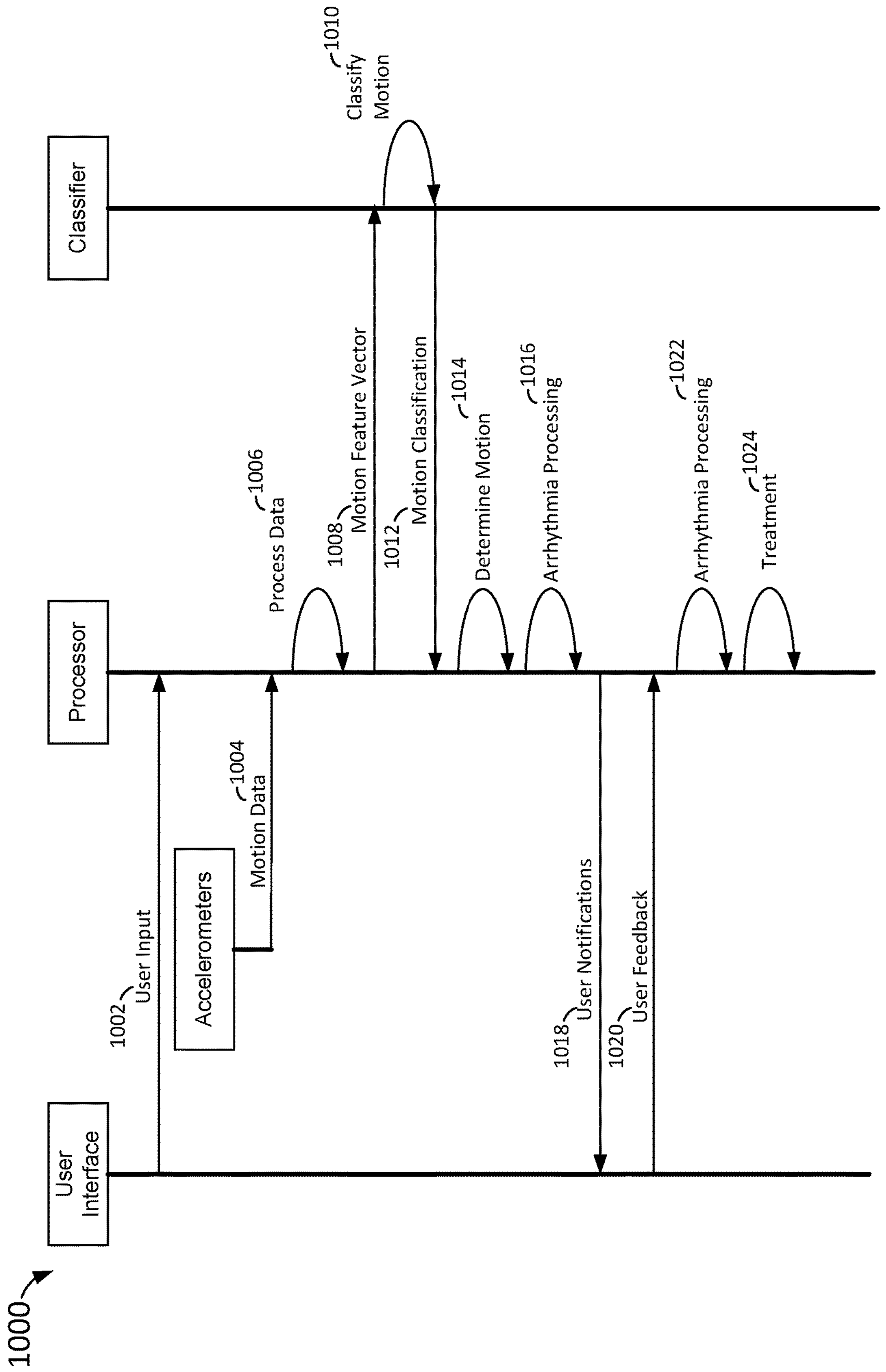
FIGS. 10A, 10B, 11A, and 11B illustrate sequence diagrams for classifying motion, in accordance with examples of the present disclosure.
Figure 10B:
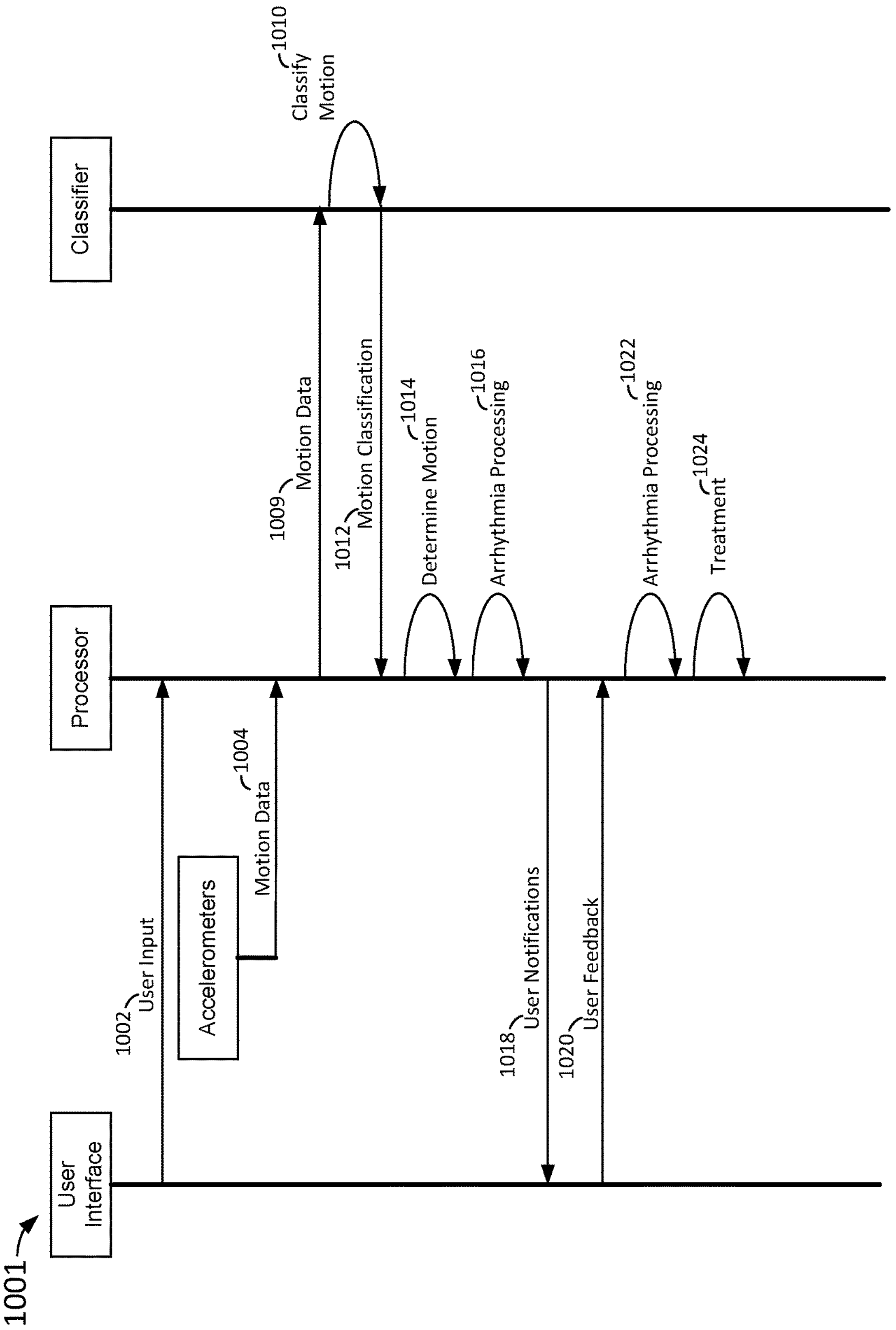
Figure 11A:
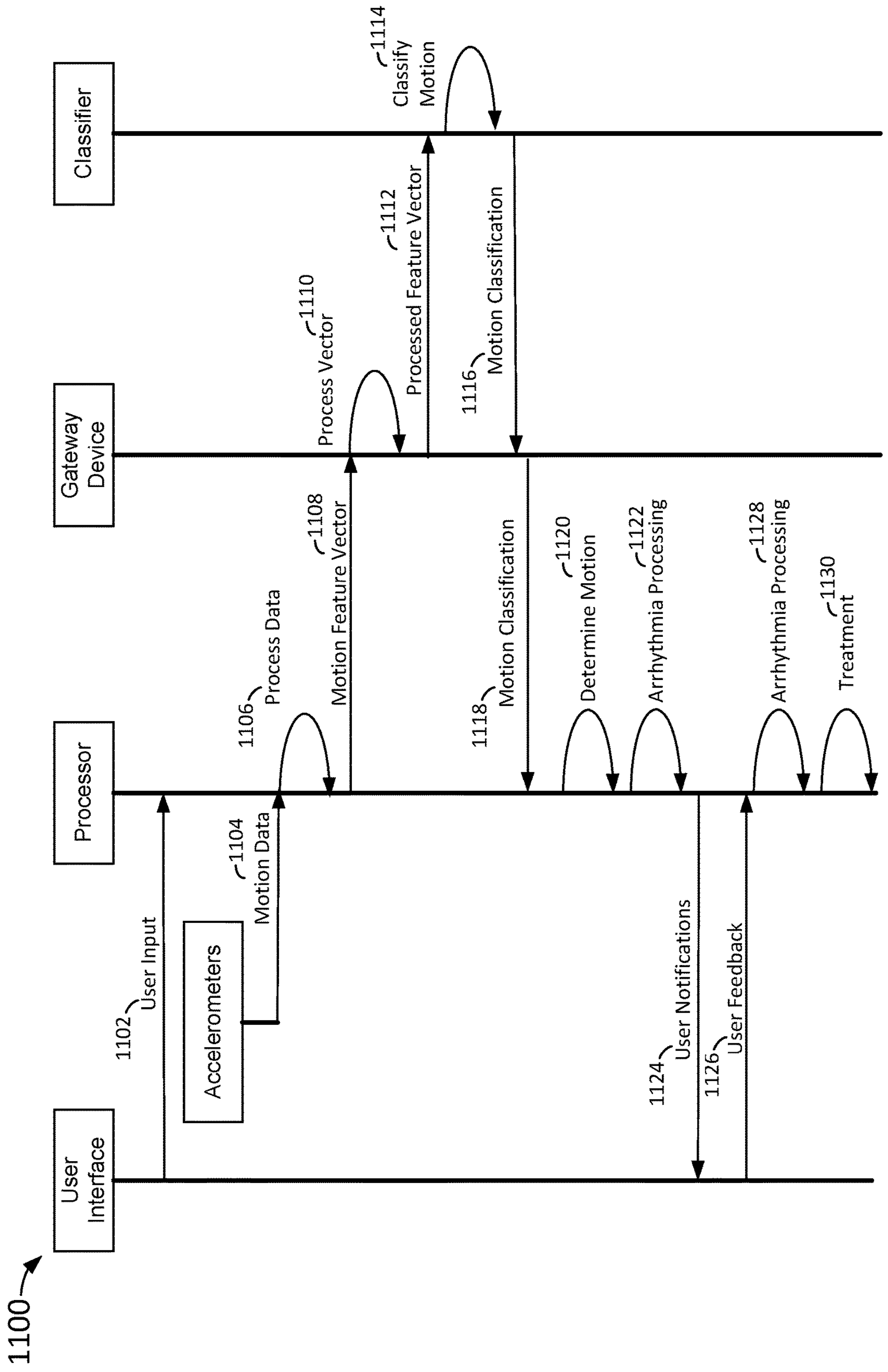
Figure 11B:
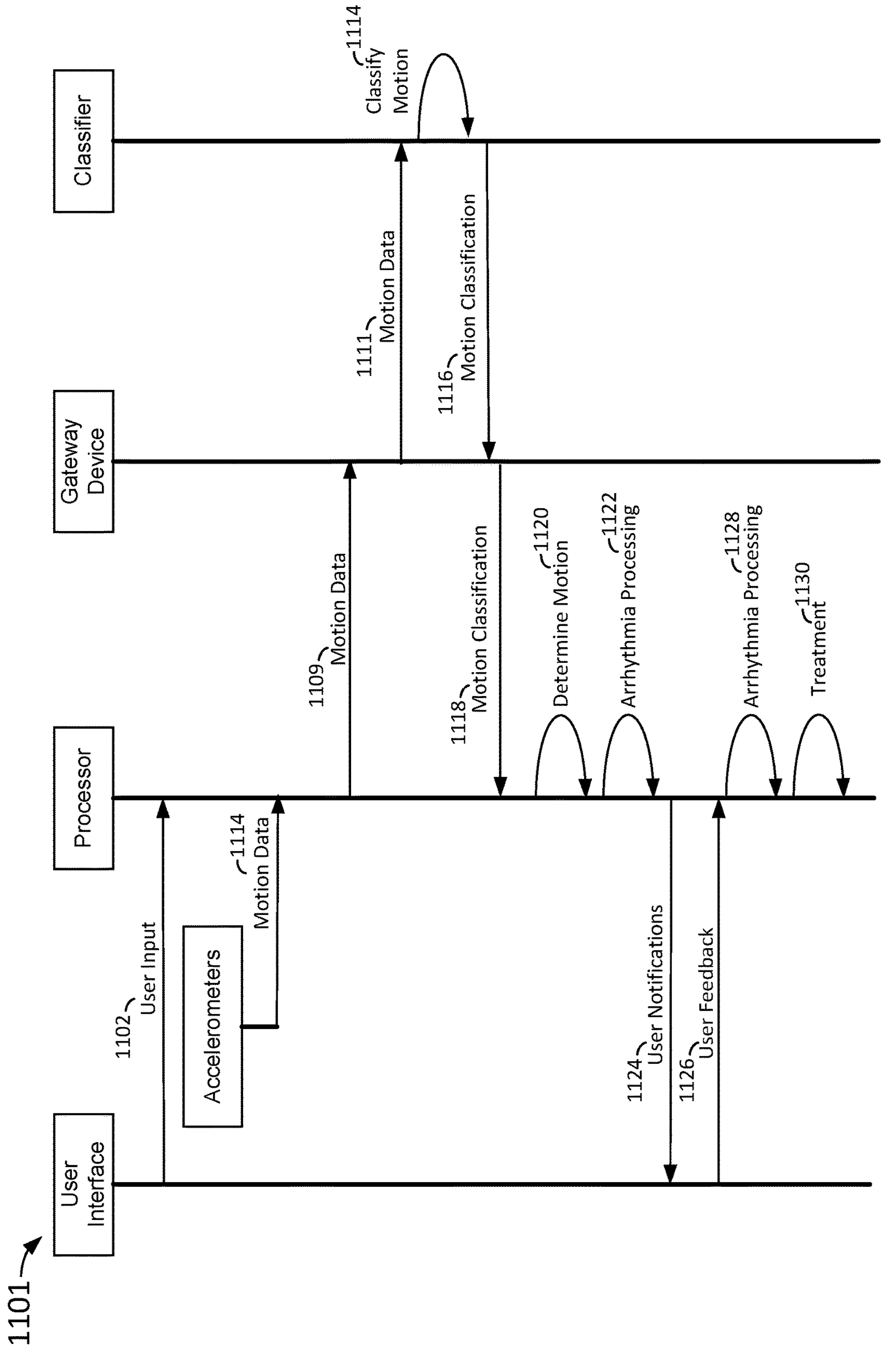

FIGS. 10A, 10B, 11A, and 11B illustrate sample sequence diagrams for determining motion classifications using a similar process as process 900 and process 910 as described above. More specifically, FIGS. 10A and 10B illustrate a process as implemented by a medical device controller processor where the motion classifier is stored locally on the medical device and FIGS. 11A and 11B illustrate a process as implemented by a medical device controller processor where the motion classifier is remotely stored on, for example, a gateway device.

As shown in FIG. 10A, a sample sequence 1000 of interactions between a user interface (e.g., user interface 308 as described herein), one or more accelerometers (e.g., one or more of accelerometers 332 as described herein), a processor (e.g., processor 318 as described herein), and a classifier (e.g., motion classifier 802 as described herein) is provided. As shown in sequence 1000, the processor can receive 1002 any user input from the user interface. For example, the user can provide a notification that they are about to engage in a physical activity or provide confirmation that they are currently engaged in a physical activity. The processor can also receive 1004 motion data from the one or more accelerometers. The processor can process 1006 the data to generate a motion feature vector as described above. The processor can input 1008 the motion feature vector to the motion classifier and the motion classifier can classify 1010 the motion. The processor can receive 1012 the motion classification from the motion classifier and determine 1014 what type of motion the patient is currently engaged in. Based upon the classification, the processor can adjust 1016 the arrhythmia processing as described herein.

As further shown in FIG. 10A, throughout the arrhythmia processing the processor can provide 1018 user notifications to the user interface and receive 1020 user feedback from the user interface. The processor can continue to perform 1022 arrhythmia processing and, if needed, provide 1024 treatment to the patient.

As shown in FIG. 10B, a sample sequence 1001 of interactions between a user interface (e.g., user interface 308 as described herein), one or more accelerometers (e.g., one or more of accelerometers 332 as described herein), a processor (e.g., processor 318 as described herein), and a classifier (e.g., motion classifier 802 as described herein) is provided. As noted above in the discussion of FIG. 9B and process 920, depending upon the functionality and training of the motion classifier, the processor does not need to perform any processing of the motion data to extract motion data features. As such, sequence 1001 as shown in FIG. 10B includes similar steps as sequence 1000 shown in FIG. 10A and described above with the exception of the processor sending 1009 the motion data to the motion classifier for processing. As such, rather than include the processor processing the motion data to extract motion data features, the processor can send 1009 the raw accelerometer data to the motion classifier for processing.

As shown in FIG. 11A, a sample sequence 1100 of interactions between a user interface (e.g., user interface 308 as described herein), one or more accelerometers (e.g., one or more of accelerometers 332 as described herein), a processor (e.g., processor 318 as described herein), a gateway device (e.g., gateway device 814 as described above) and a classifier installed on the gateway device (e.g., motion classifier 816 as described herein) is provided. As shown in sequence 1100, the processor can receive 1102 any user input from the user interface. For example, the user can provide a notification that they are about to engage in a physical activity or provide confirmation that they are currently engaged in a physical activity. The processor can also receive 1104 motion data from the one or more accelerometers. The processor can process 1106 the data to generate a motion feature vector as described above. The processor can transmit 1108 the motion feature vector to the gateway device. The gateway device can process 1110 the motion feature vector and input 1112 the processed motion feature vector to the motion classifier and the motion classifier can classify 1114 the motion. The gateway device can receive 1116 the motion classification from the motion classifier and transmit 1118 the motion classification to the processor. The processor can determine 1120 what type of motion the patient is currently engaged in. Based upon the classification, the processor can adjust 1122 the arrhythmia processing as described herein.

As further shown in FIG. 11A, throughout the arrhythmia processing the processor can provide 1124 user notifications to the user interface and receive 1126 user feedback from the user interface. The processor can continue to perform 1128 arrhythmia processing and, if needed, provide 1130 treatment to the patient.

As shown in FIG. 11B, a sample sequence 1101 of interactions between a user interface (e.g., user interface 308 as described herein), one or more accelerometers (e.g., one or more of accelerometers 332 as described herein), a processor (e.g., processor 318 as described herein), a gateway device (e.g., gateway device 814 as described above), and a classifier (e.g., motion classifier 816 as described herein). As noted above in the discussion of FIG. 9B and process 920, depending upon the functionality and training of the motion classifier, the processor does not need to perform any processing of the motion data to extract motion data features. As such, sequence 1101 as shown in FIG. 11B includes similar steps as sequence 1100 shown in FIG. 11A and described above with the exception of the processor sending 1109 the motion data to the gateway device, and the gateway device sending 1111 the motion data to the motion classifier for processing. As such, rather than include the processor processing the motion data to extract motion data features, the processor can send 1109 the raw accelerometer data to the gateway device for further processing.

Figure 12A:
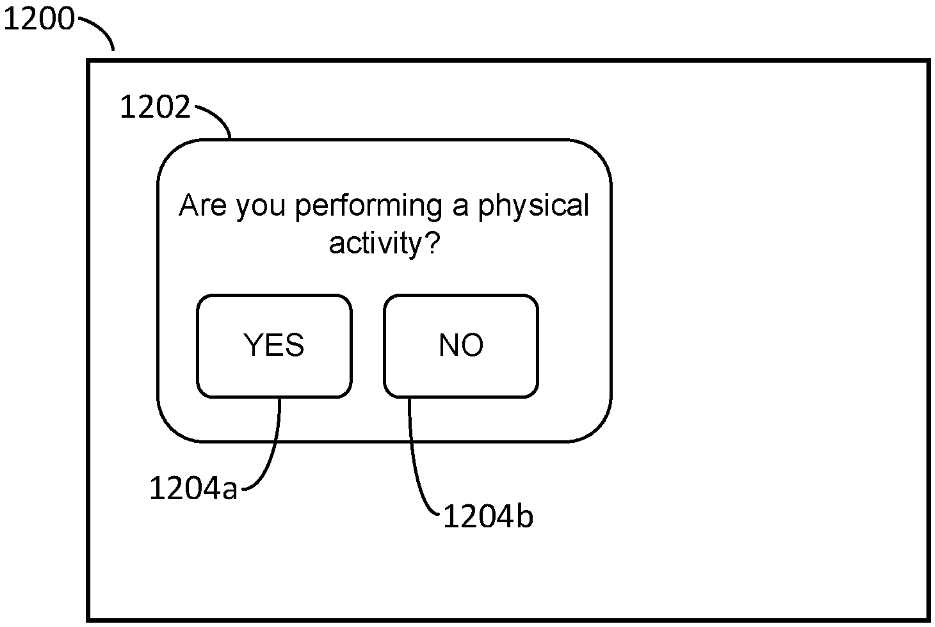
FIGS. 12A, 12B, 13A, and 13B illustrate sample user interfaces, in accordance with examples of the present disclosure.
Figure 12B:
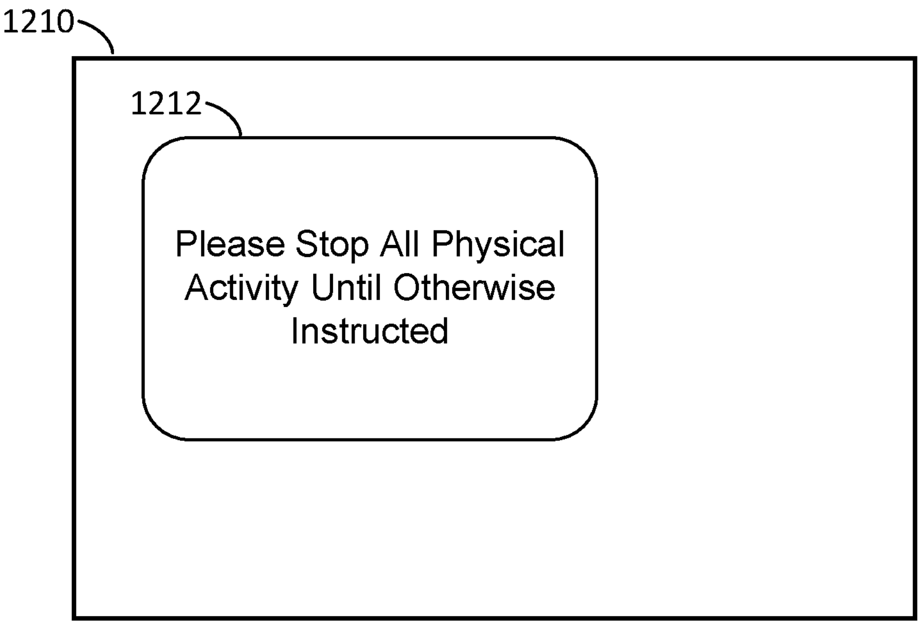

As noted above, for example, in the discussion of processes 500 and 600 as shown in FIGS. 5 and 6, a user such as a patient wearing a medical device can be prompted to provide additional information related to physical activities that the patient may be performing. FIG. 12A illustrates a sample view of a user interface screen 1200 that can be presented on a user interface to a patient or wearer of a medical device to determine if the patient is performing a physical activity. For example, as shown in FIG. 12A, the user interface screen 1200 can include a user interface text box 1202 that includes a query for the patient about whether they are performing a physical activity. The user interface text box 1202 can include user interface controls 1204*a* and 1204*b* for responding to the query. The patient can interact with one of user interface control 1204*a* and 1204*b* to answer the query as shown in user interface text box 1202. Depending upon the answer to the query, the processor of the medical device controller can update the user interface screen 1202. For example, as shown in FIG. 12B, if the patient has responded in the affirmative to the query (i.e., selected user interface control 1204*a*), an updated user interface screen 1210 can be displayed. The user interface screen 1210 can include a user interface text box 1212 that includes instructions to the patient to stop all physical activity. Depending upon the current condition of the patient, the user interface text box 1212 can include additional information such as contact your physician or to seek immediate medical assistance.

In some implementations, a patient or user of a medical device can proactively provide information to the medical device about an upcoming physical activity. For example, immediately prior to engaging in the physical activity, the patient can provide information about the activity such as activity type and activity duration. Based upon this information, the processor of the medical device controller can adjust what monitoring mode to use during the activity.

Figure 13A:
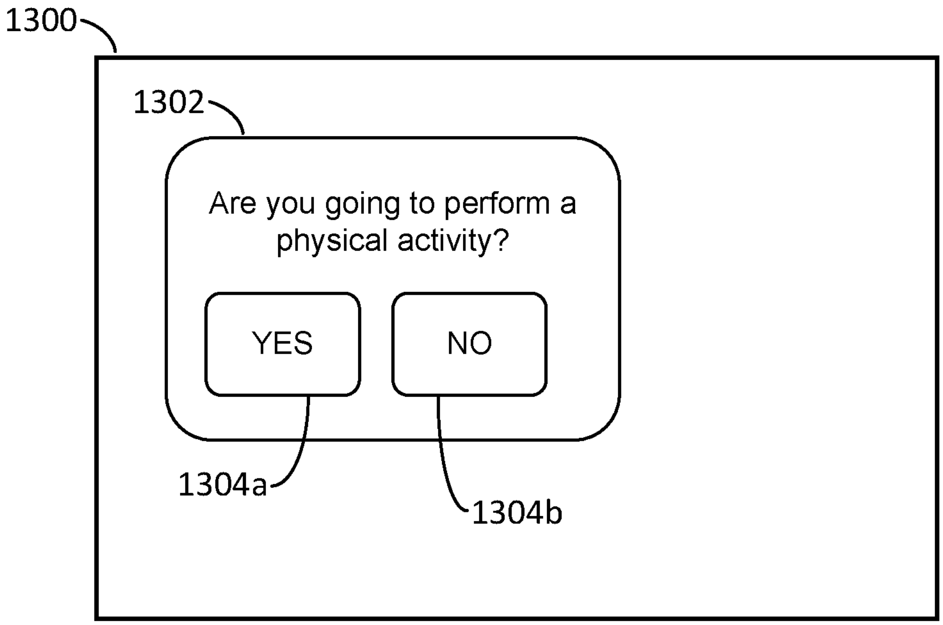
Figure 13B:
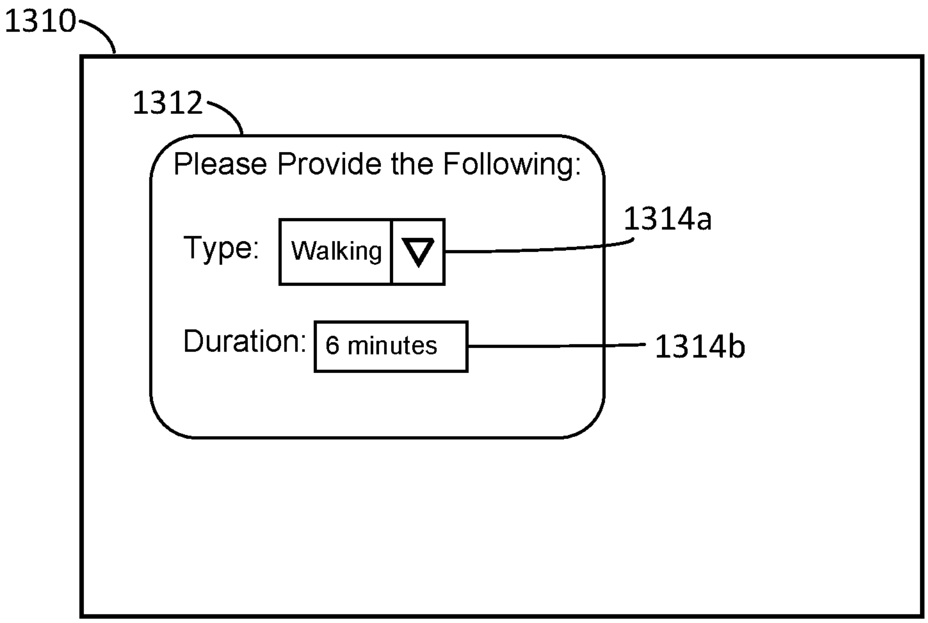

For example, FIG. 13A illustrates a sample view of a user interface screen 1300 that can be presented on a user interface to a patient or wearer of a medical device to prompt the user to provide information related to the physical activity. For example, as shown in FIG. 13A, the user interface screen 1300 can include a user interface text box 1302 that includes a query for the patient about whether they are going to perform a physical activity. The user interface text box 1302 can include user interface controller 1304*a* and 1304*b* for responding to the query. The patient can interact with one of user interface control 1304*a* and 1304*b* to answer the query as shown in user interface text box 1302. Depending upon the answer to the query, the processor of the medical device controller can update the user interface screen 1302. For example, as shown in FIG. 13B, if the patient has responded in the affirmative to the query (i.e., selected user interface control 1304*a*), an updated user interface screen 1310 can be displayed. The user interface screen 1310 can include a user interface text box 1312 that includes additional user interface controls 1314*a* and 1314*b*. The patient can interact with user interface control 1314*a* to select the type of activity they are about to perform. For example, as shown in FIG. 13B, the user interface control 1314*a* can include a drop-down menu from which the patient can define an activity type within the user interface control. However, it should be noted that a drop-down menu is shown by way of example only and other user interface controls 1314*a* can be included. Additionally, the patient can interact with user interface control 1314*b* to define duration information for the selected activity within the user interface control. As shown in FIG. 13B, the patient has selected walking as the type of activity and six minutes as the expected duration.

Applicants have conducted experiments using the techniques as described herein to classify subject movement when a test subject is wearing a device including one or more accelerometers as is described herein. In the experiments, the output from one or more accelerometers can be used as input data for a motion classifier. In some experiments, rather than attempt to classify every single data point (e.g., at a 50 Hz sampling rate), applicants have performed feature extraction as described herein to compute features of the motion data that are based on a temporal window. This can reduce the computation burden of the motion classification process, reduce the effect of noise, and reduce the temporal dependence of subsequent examples. For example, feature extraction was performed on temporal windows with 50% overlap. In some examples, window sizes included 512 samples with 256 samples of overlap at a sampling rate of 76.25 Hz, resulting in a temporal window of about 6.7 seconds. In another experiment, feature extraction was performed with window sizes of 256 samples with 128 samples of overlap at a sampling rate of 50 Hz, resulting in a temporal window of about 5.12 seconds.

In some experiments, the extracted features were split into two distinct types. The first type included time domain features such as the mean, standard deviation, and correlation within the temporal window. The second type included frequency domain features such as entropy, energy, and coherence (i.e., correlation in the frequency domain).

Additionally, various positions of the accelerometers on the subject's body were considered during the experiments. For example, sample accelerometer placements included on the hip (e.g., on a belt worn by the subject), on the wrist, on the upper arm, on the ankle, on the chest/trunk, near the armpit, on the upper chest, on the thigh, on the shoulder, on the back, and other similar positions on the subject's body.

In a specific experiment, a test subject wore a cardiac monitoring device and an accelerometer position on the center of the subjects back. The accelerometer used included pitch and roll outputs as well as outputs representing x-axis acceleration, y-axis acceleration, and z-axis acceleration.

Throughout the test, the subject performed various activities such as laying down, transitioning from laying to sitting, talking, running, and other various tasks. Table 2 below includes a detailed overview of the task taken, a time the subject recorded the task beginning, a time the subject recorded the task ending, and any details about the task.

TABLE 2

| Initial manual recording time | Task | Post-task manual recording time | Details |
|---|---|---|---|
| 4:15 pm | Patient laying down | 4:18 pm | Laying on bed |
| 4:20 pm | Patient transition from laying down to sitting/standing position | 4:23 pm | Transition from laying on bed to sitting on bed |
| 4:23 pm | Patient sitting or standing | 4:26 pm | Sitting on bed |
| 4:27 pm | Patient transition from sitting/ standing position to walking | 4:30 pm | Transition from sitting on bed to walking - back and forth from bedroom into hallway |
| 4:30 pm | Patient walking | 4:33/4:34 pm | Walking outside (some elevation) |
| 4:34 pm | Patient running (step count/min increases?) | 4:37 pm | Running outside (some elevation). Treatment alarm at ~4:36 pm |
| 4:40 pm | Patient climbing up/down stairs | 4:43 pm | Walking up and down stairs of 3 story multi-level home. 4:41 pm bent over to pick something up |

Additionally, motion classifier models as described herein were used to classify the subject's activities throughout the test. The output of the motion classifier models can be configured, for example, as a table or matrix that includes numerical values from 0.0 (low) to 1.0 (high) indicating a confidence value as determined by the model. For example, Table 3 illustrates a sample output matrix for a motion classifier model as described herein. In Table 3, both the row and column labels can include a listing of the activities that the motion classifier model is trained to identify. Individual cells in the table can indicate a combination of two possible activities as indicated by coordinate pair (e.g., row, column). For example, a high value close to 1.0 in the cell walking, running can indicate that the subject is transitioning from walking to running.

TABLE 3

| | Laying Down | Sitting | Standing | Walking | Running | Climbing Stairs |
|---|---|---|---|---|---|---|
| Laying Down | 0.0-1.0 | 0.0-1.0 | 0.0-1.0 | 0.0-1.0 | 0.0-1.0 | 0.0-1.0 |
| Sitting | 0.0-1.0 | 0.0-1.0 | 0.0-1.0 | 0.0-1.0 | 0.0-1.0 | 0.0-1.0 |
| Standing | 0.0-1.0 | 0.0-1.0 | 0.0-1.0 | 0.0-1.0 | 0.0-1.0 | 0.0-1.0 |
| Walking | 0.0-1.0 | 0.0-1.0 | 0.0-1.0 | 0.0-1.0 | 0.0-1.0 | 0.0-1.0 |
| Running | 0.0-1.0 | 0.0-1.0 | 0.0-1.0 | 0.0-1.0 | 0.0-1.0 | 0.0-1.0 |
| Climbing Stairs | 0.0-1.0 | 0.0-1.0 | 0.0-1.0 | 0.0-1.0 | 0.0-1.0 | 0.0-1.0 |

FIGS. 14A-14D provide examples of accelerometer output when a patient is measured while the test subject performed one or more tasks as shown in Table 2 above.

Figure 14A:
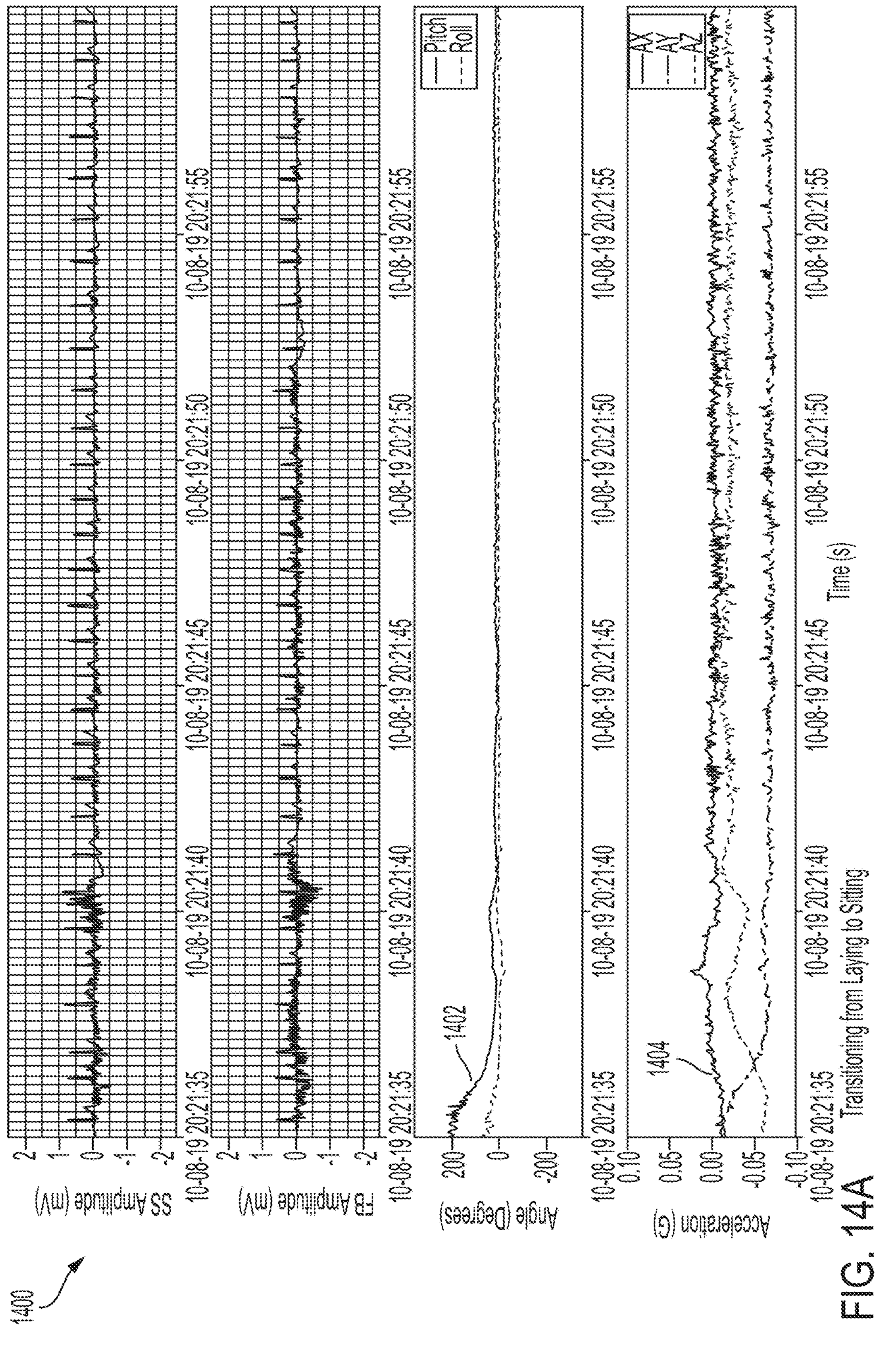
FIGS. 14A-14D illustrate sample accelerometer data, in accordance with an example of the present disclosure.

As shown in FIG. 14A, accelerometer data 1400 shows sample output data as the test subject transitions from laying down to a sitting position. For example, at point 1402, the pitch signal drops from about 200 degrees to about 0 degrees indicating that the accelerometer has moved from a horizontal position to a vertical position. Similarly, at point 1404, the y-axis output and z-axis output swap values, the y-axis going from about 0 g to about −0.05 g and the z-axis output going from about −0.05 g to about 0 g. Using a motion classifier model such as those described above, the output of the accelerometer as shown in FIG. 14A was classified as transitioning from a laying to a sitting position. For example, Table 4 illustrates a set of sample data as output by the motion classifier model indicating that the subject was transitioning from laying down to a sitting position. As shown in Table 4, the cell having a (row, column) value of (laying down, sitting) has a value of 0.95, indicating that the output of the motion classifier model indicates that the subject is transitioning from laying down to a sitting position.

TABLE 4

| | Laying Down | Sitting | Standing | Walking | Running | Climbing Stairs |
|---|---|---|---|---|---|---|
| Laying Down | 0.2 | 0.95 | 0.1 | 0.0 | 0.0 | 0.0 |
| Sitting | 0.1 | 0.4 | 0.05 | 0.0 | 0.0 | 0.0 |
| Standing | 0.05 | 0.0 | 0.1 | 0.0 | 0.0 | 0.0 |
| Walking | 0.0 | 0.0 | 0.0 | 0.0 | 0.0 | 0.0 |
| Running | 0.0 | 0.0 | 0.0 | 0.0 | 0.0 | 0.0 |
| Climbing Stairs | 0.0 | 0.0 | 0.0 | 0.0 | 0.0 | 0.0 |

Figure 14B:
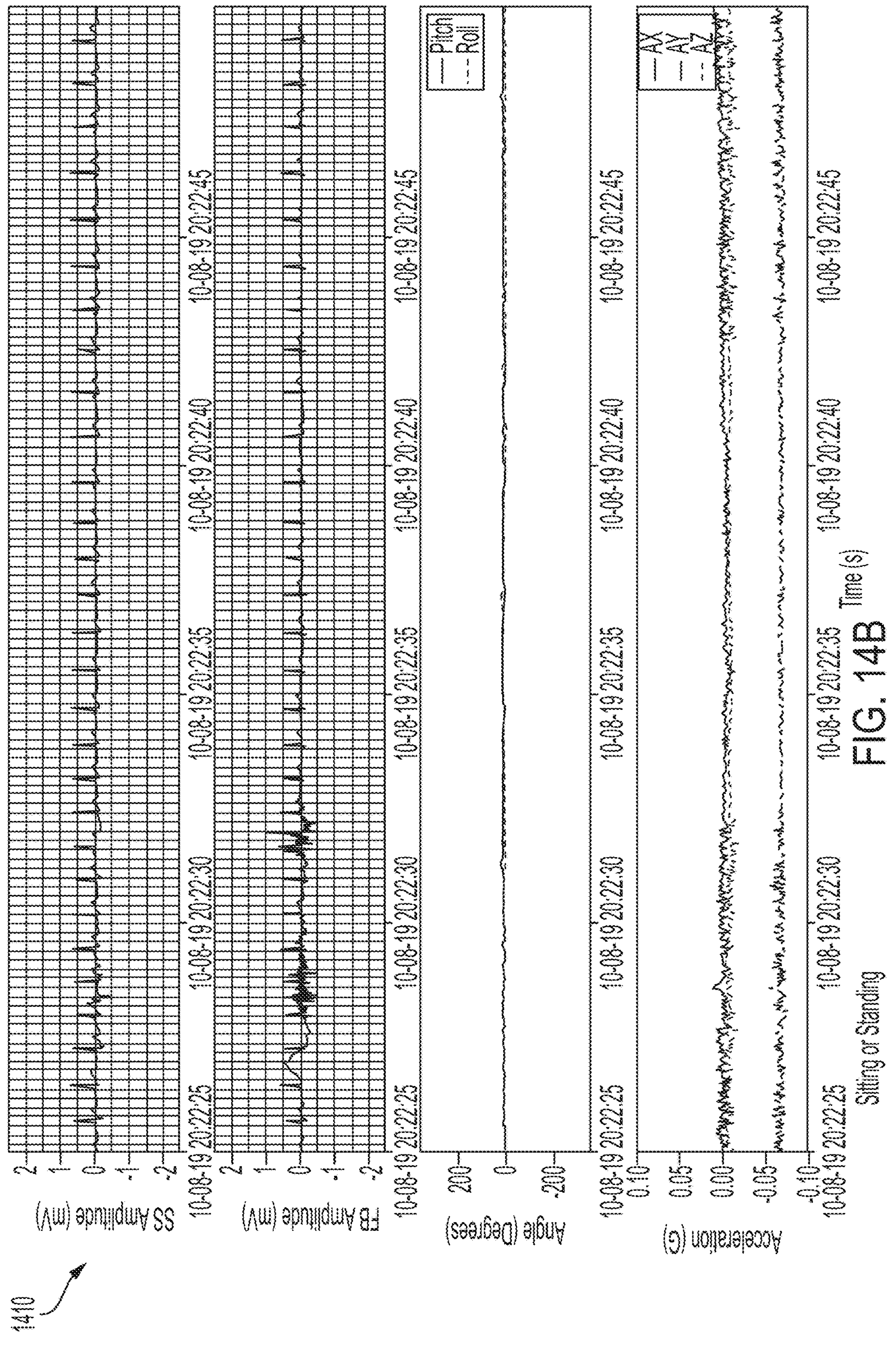

As shown in FIG. 14B, accelerometer data 1410 shows sample output data as the test subject stays in a sifting position for a period of time. As shown in FIG. 14B, the accelerometer used provides pitch and roll outputs as well as outputs for each of the x-axis, the y-axis, and the z-axis. For example, as time progresses, the pitch and roll outputs remain nearly steady as do the outputs for the x-axis, the y-axis, and the z-axis. Using a motion classifier model such as those described above, the output of the accelerometer as shown in FIG. 14B was classified as sitting or standing. For example, Table 5 illustrates a set of sample data as output by the motion classifier model indicating that the subject was in a sifting position. As shown in Table 5, the cell having a (row, column) value of (sifting, sifting) has a value of 1.0, indicating that the output of the motion classifier model is indicating that the subject is in a sifting position.

TABLE 5

| | Laying Down | Sit-ting | Stand-ing | Walk-ing | Run-ning | Climbing Stairs |
|---|---|---|---|---|---|---|
| Laying Down | 0.05 | 0.1 | 0.1 | 0.0 | 0.0 | 0.0 |
| Sitting | 0.1 | 1.0 | 0.05 | 0.0 | 0.0 | 0.0 |
| Standing | 0.05 | 0.0 | 0.25 | 0.0 | 0.0 | 0.0 |
| Walking | 0.0 | 0.0 | 0.0 | 0.0 | 0.0 | 0.0 |
| Running | 0.0 | 0.0 | 0.0 | 0.0 | 0.0 | 0.0 |
| Climbing Stairs | 0.0 | 0.0 | 0.0 | 0.0 | 0.0 | 0.0 |

Figure 14C:
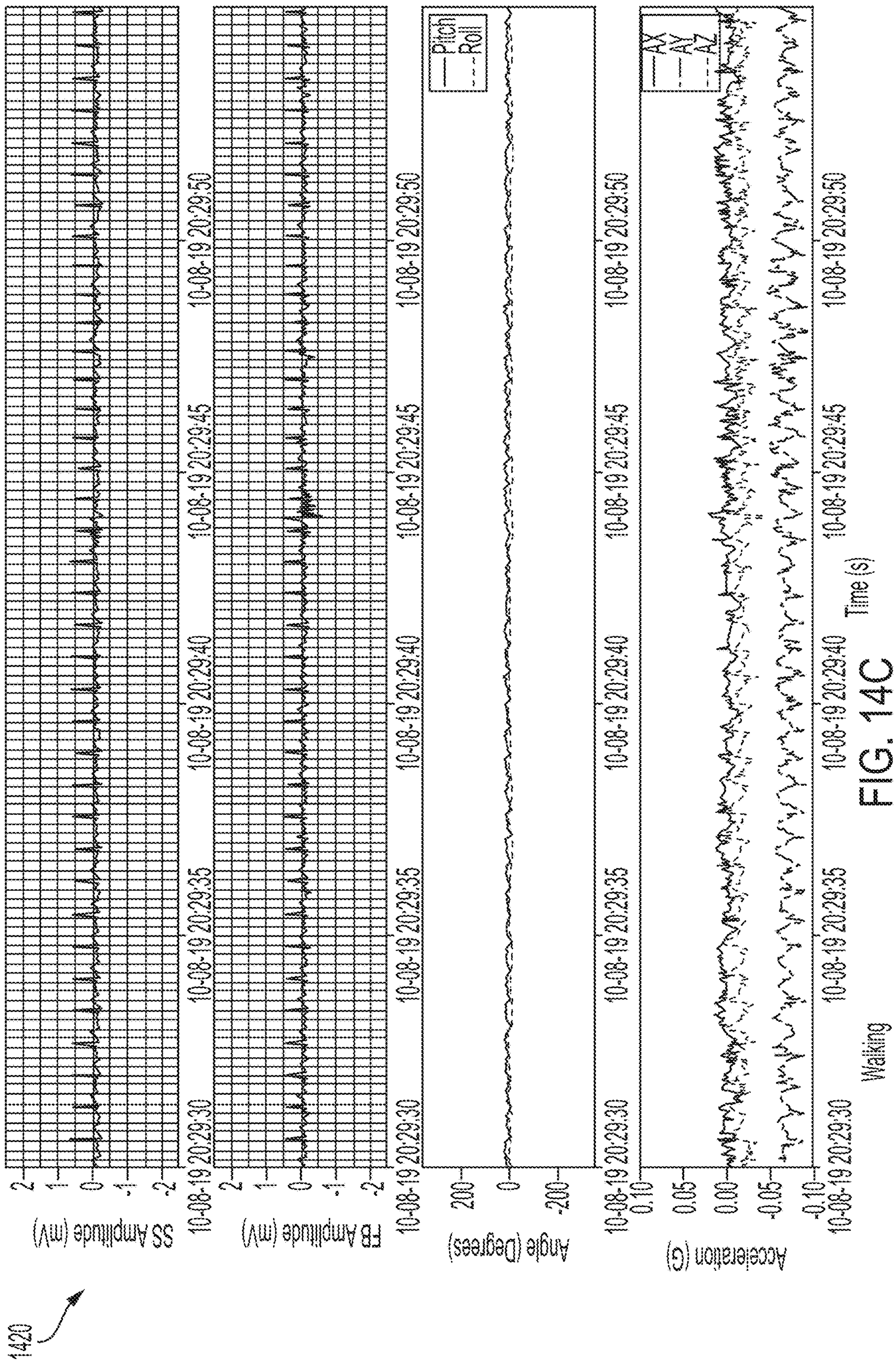

As shown in FIG. 14C, accelerometer data 1420 shows sample output data as the test subject is walking. For example, as time progresses, the pitch and roll outputs slightly transition above and below 0 degrees. As further shown, the output representing the x-axis transitions slightly above and below about 0 g, the output representing the y-axis transitions slightly above and below about −0.075 g, and the output representing the z-axis transitions slightly above and below about −0.025 g. Using a motion classifier model such as those described above, the output of the accelerometer as shown in FIG. 14C was classified as walking. For example, Table 6 illustrates a set of sample data as output by the motion classifier model indicating that the subject was walking. As shown in Table 6, the cell having a (row, column) value of (walking, walking) has a value of 1.0, indicating that the output of the motion classifier model is indicating that the subject is walking.

TABLE 6

| | Laying Down | Sit-ting | Stand-ing | Walk-ing | Run-ning | Climbing Stairs |
|---|---|---|---|---|---|---|
| Laying Down | 0.0 | 0.0 | 0.0 | 0.0 | 0.0 | 0.0 |
| Sitting | 0.0 | 0.0 | 0.0 | 0.0 | 0.0 | 0.0 |
| Standing | 0.05 | 0.0 | 0.0 | 0.1 | 0.05 | 0.05 |
| Walking | 0.0 | 0.0 | 0.0 | 1.0 | 0.2 | 0.1 |
| Running | 0.0 | 0.0 | 0.0 | 0.1 | 0.2 | 0.1 |
| Climbing Stairs | 0.0 | 0.0 | 0.0 | 0.1 | 0.1 | 0.2 |

Figure 14D:
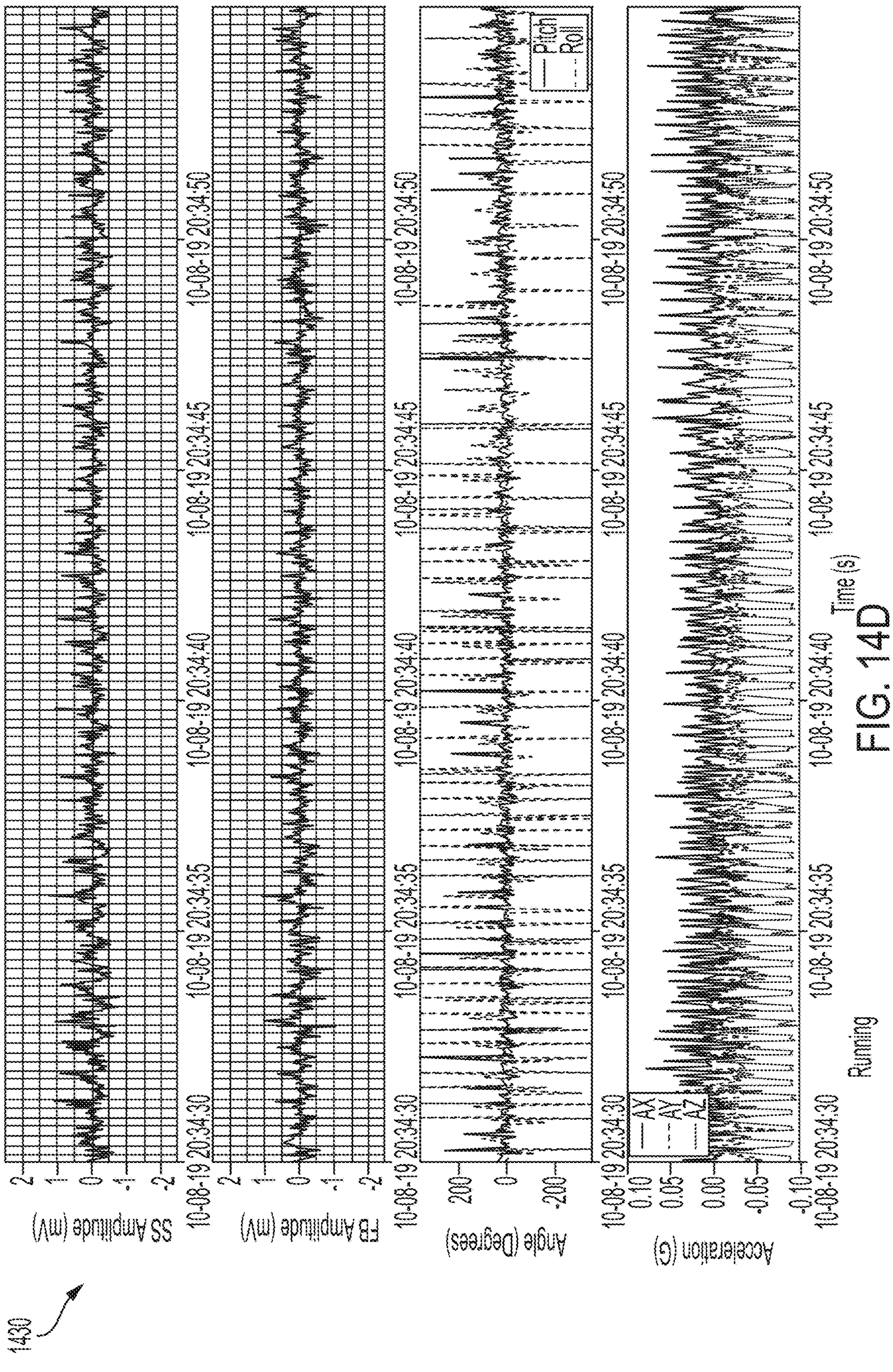

As shown in FIG. 14D, accelerometer data 1430 shows sample output data as the test subject is running. For example, as time progresses, the pitch and roll outputs transition quickly above and below zero degrees, sometimes exceeding plus and minus 200 degrees from zero. As further shown, the output representing the x-axis, the y-axis, and the z-axis are transitioning quickly between about 0.1 g and −0.1 g. Using a motion classifier model such as those described above, the output of the accelerometer as shown in FIG. 14D was classified as running. For example, Table 7 illustrates a set of sample data as output by the motion classifier model indicating that the subject was running. As shown in Table 7, the cell having a (row, column) value of (running, running) has a value of 0.95, indicating that the output of the motion classifier model is indicating that the subject is running.

TABLE 7

| | Laying Down | Sit-ting | Stand-ing | Walk-ing | Run-ning | Climbing Stairs |
|---|---|---|---|---|---|---|
| Laying Down | 0.0 | 0.0 | 0.0 | 0.0 | 0.0 | 0.0 |
| Sitting | 0.0 | 0.0 | 0.0 | 0.0 | 0.0 | 0.0 |
| Standing | 0.05 | 0.0 | 0.0 | 0.0 | 0.1 | 0.05 |
| Walking | 0.0 | 0.0 | 0.0 | 0.1 | 0.2 | 0.0 |
| Running | 0.0 | 0.0 | 0.0 | 0.1 | 0.95 | 0.1 |
| Climbing Stairs | 0.0 | 0.0 | 0.0 | 0.0 | 0.1 | 0.1 |

It should be noted that running, walking, riding a bicycle, laying, sitting, and climbing stairs are described herein in specific examples as types of activities by way of example only. The motion classification techniques as described herein can be used to determine additional activities such as, for example, sleeping, eating, playing a sport, pushing a shopping cart, driving a car, brushing teeth and other grooming activities, kneeling, washing, cleaning, folding laundry, riding an elevator, jumping, and other similar physical activities.

In an example, a patient may be prescribed a wearable medical device such as a WCD. While prescribed the WCD, the patient may also be given a physical rehabilitation plan that includes, for example, daily walking exercises. Prior to starting the walking exercise, the patient can access a menu on a user interface of the WCD to indicate that they are about to begin a physical activity. Upon receiving the notification, a processor of the WCD can transition an arrhythmia detection process from an AIN sensitive mode to an AIN robust mode. During the physical activity, the processor can monitor the patient's heart rate for any indications of a potentially life-threatening situation. In examples, during the AIN robust mode, the processor can monitor the QRS width, R-wave amplitude, and/or T-wave amplitude, for predetermined changes or other abnormalities indicating a potentially life-threatening situation. If such a situation occurs, the processor can provide a notification to the patient to stop the physical activity immediately. Once the patient has stopped the physical activity, the processor can transition back to the AIN sensitive mode to confirm the life-threatening situation. Based upon the confirmation, the processor can notify the patient it is safe to resume the physical activity, instruct the patient to not continue the physical activity, or notify the patient to seek medical assistance.

In another example, a patient may be prescribed a wearable medical device such as a WCD. While prescribed the WCD, the patient may also be given a physical rehabilitation plan that includes, for example, daily walking exercises. Prior to starting the walking exercise, the patient can access a menu on a user interface of the WCD to indicate that they are about to begin a physical activity. Upon receiving the notification, a processor of the WCD can transition an arrhythmia detection process from a default and full arrhythmia detection mode to a heart rate based arrhythmia detection mode. However, the patient prematurely stops or never begins the rehabilitation exercise. Upon a certain time without recognized physical activity, the device may provide a notification that no activity is observed before transitioning back to full arrhythmia detection mode.

In another example, a patient prescribed a wearable medical device may be cutting their grass using a push lawnmower. Due to the movement of their body while pushing the lawnmower and the noise of the lawnmower, the patient may not hear a notification to confirm that they are performing a physical activity. However, motion data collected by various motion sensors such as accelerometers as described herein can be input into a motion classifier by a processor of the WCD. Based upon the output of the motion classifier, the processor can determine that the patient is performing a physical activity such as walking/running or pushing an object and, as such, any potential noise in any ECG signals is likely due to the physical activity.

In a similar example, a patient prescribed a wearable medical device may be cutting their grass using a push lawnmower. Due to the movement of their body while pushing the lawnmower and the noise of the lawnmower, the patient may not hear a notification to confirm that they are performing a physical activity. However, motion data collected by various motion sensors such as accelerometers as described herein can be input into a motion classifier by a processor of the WCD. Based upon the output of the motion classifier, the processor may not be able to definitively determine that the patient is performing a physical activity such as walking/running or pushing an object. However, the motion classifier may indicate a higher risk of difficulty hearing and alarms may be adjusted accordingly. For example, the device controller can automatically adjust the alarm volume and alarm duration to account for the detected motion and possible difficulty of hearing.

In some examples, the motion analysis may be further refined to be able to distinguish motions generating AIN or motions that are more likely to generate AIN from motions that may not or are likely not to generate AIN. In one example, a spectral analysis may be performed on the motion signal, dividing the spectrum into at least two bands: at least one band, the "in-band", that is the band in which it is predetermined that is in the range typical of the frequency distribution of ECG signals; and at least one band, the "ex-band", that is not in the range typical of the frequency distribution of ECG signals. The spectral energy content is then computed for the in-bands and ex-bands of the spectrum. If more than a predetermined threshold is exceeded for the relative energy content for the in-band range, then the algorithm will switch to the AIN robust mode. In example implementations, the threshold can be 5%, 10%, 20%, 40%, 50%, 75%, a predetermined value in the range of around 0.1 to around 75%, or a user set value in a range of around 0.1 to around 75%.

Alternatively or additionally, the spectrum of the motion signal is compared to the spectrum of the ECG via known spectrum comparison techniques such as a cross-correlation method, a bin method, a correlation coefficient comparison, and other similar spectrum comparison techniques to determine a similarity threshold. For example, a cross-correlation comparison method includes measuring the similarity of two particular functions such as the spectrum of a motion signal and the spectrum of an ECG signal as described herein. The cross-correlation of the two functions, represented by f(t) and g(t), can be defined as $$(f * g)(\tau) \triangleq \int_{-\infty}^{\infty} \overline{f(t-\tau)}\, g(t)\, dt$$

where $\overline{f(t)}$ is the complex conjugate of f(t) and z represents displacement or lag between the functions. The cross-correlation of the two functions can be represented as a set of values between 0.0 and 1.0 that represent the similarity between the two functions at specific time periods. For example, a cross-correlation value of 0.90 at time $t_1$ can represent 90% similarity at time $t_1$. The cross-correlation values can be computed for the functions and an average percent cross-correlation can be determined representing an overall similarity between the two functions.

When using a bin method, the functions can be split into a number of bins representing discrete timing periods. In each of the bins, the average frequency value for each of the two functions can be compared and a difference value between 0.0 and 1.0 can be calculated. The difference values for each of the bins can be added and divided by the number of bins to calculate an average difference between the two functions. The average difference value can be subtracted from 1.0 and the resulting value can represent the overall similarity of the two functions represented as a value between 0.0 and 1.0 which can be converted to a percentage between 0% and 100%. When using the bin method, including a higher number of smaller bins (e.g., using smaller timing periods) can provide more accurate overall similarity values.

When using a correlation coefficient comparison, the linear correlation between two functions can be computed over a particular time period. The time period can be divided into a number of equal portions and a linear correlation value for each time period can be computed. The linear correlation values can be between −1.0 and 1.0 where −1.0 is a total negative linear correlation, 0.0 is no linear correlation, and 1.0 is total positive correlation. The linear correlation values for each of the time periods can be added together and divided by the total number of time periods to calculate an average linear correlation between −1.0 and 1.0. The average linear correlation can be converted to a percentage of linear correlation that is between −100% and 100%, thereby representing an overall similarity between the two functions. Similar to the bin method, when using a correlation coefficient comparison, a higher number of timing periods can provide more accurate overall similarity values.

If, after performing a spectrum comparison, the overall similarity exceeds a predetermined threshold, then the algorithm will switch to the AIN robust mode. In example implementations, the similarity threshold can be 30%, 40%, 50%, 60%, 75%, 100%, a predetermined value in the range of around 30% to around 100%, or a user set value in a range of around 30% to around 100%.

The teachings of the present disclosure can be generally applied to external medical monitoring and/or treatment devices that include one or more accelerometers as described herein. Such external medical devices can include, for example, ambulatory medical devices as described herein that are capable of and designed for moving with the patient as the patient goes about his or her daily routine. An example ambulatory medical device can be a wearable medical device such as a WCD, a wearable cardiac monitoring device, an in-hospital device such as an in-hospital wearable defibrillator (HWD), a short-term wearable cardiac monitoring and/or therapeutic device, mobile cardiac event monitoring devices, and other similar wearable medical devices.

The wearable medical device can be capable of continuous use by the patient. In some implementations, the continuous use can be substantially or nearly continuous in nature. That is, the wearable medical device can be continuously used, except for sporadic periods during which the use temporarily ceases (e.g., while the patient bathes, while the patient is refit with a new and/or a different garment, while the battery is charged/changed, while the garment is laundered, etc.). Such substantially or nearly continuous use as described herein may nonetheless be considered continuous use. For example, the wearable medical device can be configured to be worn by a patient for as many as 24 hours a day. In some implementations, the patient can remove the wearable medical device for a short portion of the day (e.g., for half an hour to bathe).

Further, the wearable medical device can be configured as a long term or extended use medical device. Such devices can be configured to be used by the patient for an extended period of several days, weeks, months, or even years. In some examples, the wearable medical device can be used by a patient for an extended period of at least one week. In some examples, the wearable medical device can be used by a patient for an extended period of at least 30 days. In some examples, the wearable medical device can be used by a patient for an extended period of at least one month. In some examples, the wearable medical device can be used by a patient for an extended period of at least two months. In some examples, the wearable medical device can be used by a patient for an extended period of at least three months. In some examples, the wearable medical device can be used by a patient for an extended period of at least six months. In some examples, the wearable medical device can be used by a patient for an extended period of at least one year. In some implementations, the extended use can be uninterrupted until a physician or other HCP provides specific instruction to the patient to stop use of the wearable medical device.

Regardless of the extended period of wear, the use of the wearable medical device can include continuous or nearly continuous wear by the patient as described above. For example, the continuous use can include continuous wear or attachment of the wearable medical device to the patient, e.g., through one or more of the electrodes as described herein, during both periods of monitoring and periods when the device may not be monitoring the patient but is otherwise still worn by or otherwise attached to the patient. The wearable medical device can be configured to continuously monitor the patient for cardiac-related information (e.g., ECG information, including arrhythmia information, cardio-vibrations, etc.) and/or non-cardiac information (e.g., blood oxygen, the patient's temperature, glucose levels, tissue fluid levels, and/or lung vibrations). The wearable medical device can carry out its monitoring in periodic or aperiodic time intervals or times. For example, the monitoring during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), and/or tissue fluids (e.g., using radio-frequency transmitters and sensors), among others.

Other example wearable medical devices include automated cardiac monitors and/or defibrillators for use in certain specialized conditions and/or environments such as in combat zones or within emergency vehicles. Such devices can be configured so that they can be used immediately (or substantially immediately) in a life-saving emergency. In some examples, the ambulatory medical devices described herein can be pacing-enabled, e.g., capable of providing therapeutic pacing pulses to the patient. In some examples, the ambulatory medical devices can be configured to monitor for and/or measure ECG metrics including, for example, heart rate (such as average, median, mode, or other statistical measure of the heart rate, and/or maximum, minimum, resting, pre-exercise, and post-exercise heart rate values and/or ranges), heart rate variability metrics, PVC burden or counts, atrial fibrillation burden metrics, pauses, heart rate turbulence, QRS height, QRS width, changes in a size or shape of morphology of the ECG information, cosine R-T, artificial pacing, QT interval, QT variability, T wave width, T wave alternans, T-wave variability, and ST segment changes.

As noted above, FIG. 3 illustrates an example component-level view of a medical device controller 300 included in, for example, a wearable medical device. As further shown in FIG. 3, the therapy delivery circuitry 302 can be coupled to one or more electrodes 320 configured to provide therapy to the patient. For example, the therapy delivery circuitry 302 can include, or be operably connected to, circuitry components that are configured to generate and provide an electrical therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuitry and under control of one or more processors (e.g., processor 318) to provide, for example, at least one therapeutic shock to the patient including one or more pacing, cardioversion, or defibrillation therapeutic pulses.

Pacing pulses can be used to treat cardiac arrhythmia conditions such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). In some examples, the capacitors can include a single film or electrolytic capacitor as a series connected device including a bank of the same capacitors. These capacitors can be switched into a series connection during discharge for a defibrillation pulse. For example, a single capacitor of approximately 140 uF or larger, or four capacitors of approximately 650 uF can be used. The capacitors can have a 1600 VDC or higher rating for a single capacitor, or a surge rating between approximately 350 to 500 VDC for paralleled capacitors and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuitry 302 can be configured to perform the switching and pulse delivery operations, e.g., under control of the processor 318. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

In certain examples, the therapy delivery circuitry 302 can be configured to deliver a set of cardioversion pulses to correct, for example, an improperly beating heart. When compared to defibrillation as described above, cardioversion typically includes a less powerful shock that is delivered at a certain frequency to mimic a heart's normal rhythm.

The data storage 304 can include one or more of non-transitory computer-readable media, such as flash memory, solid state memory, magnetic memory, optical memory, cache memory, combinations thereof, and others. The data storage 304 can be configured to store executable instructions and data used for operation of the medical device controller 300. In certain examples, the data storage can include executable instructions that, when executed, are configured to cause the processor 318 to perform one or more operations. In some examples, the data storage 304 can be configured to store information such as ECG data as received from, for example, the sensing electrode interface.

In some examples, the network interface 306 can facilitate the communication of information between the medical device controller 300 and one or more other devices or entities over a communications network. For example, where the medical device controller 300 is included in an ambulatory medical device, the network interface 306 can be configured to communicate with a remote computing device such as a remote server or other similar computing device. The network interface 306 can include communications circuitry for transmitting data in accordance with a Bluetooth® wireless standard for exchanging such data over short distances to an intermediary device. For example, such an intermediary device can be configured as a base station, a "hotspot" device, a smartphone, a tablet, a portable computing device, and/or other devices in proximity of the wearable medical device including the medical device controller 300. The intermediary device(s) may in turn communicate the data to a remote server over a broadband cellular network communications link. The communications link may implement broadband cellular technology (e.g., 2.5G, 2.75G, 3G, 4G, and/or 5G cellular standards) and/or Long-Term Evolution (LTE) technology or GSM/EDGE and UMTS/HSPA technologies for high-speed wireless communication. In some implementations, the intermediary device (s) may communicate with a remote server over a Wi-Fi™ communications link based on the IEEE 802.11 standard.

In certain examples, the user interface 308 can include one or more physical interface devices such as input devices, output devices, and combination input/output devices and a software stack configured to drive operation of the devices. These user interface elements can render visual, audio, and/or tactile content. Thus, the user interface 308 can receive input or provide output, thereby enabling a user to interact with the medical device controller 300.

The medical device controller 300 can also include at least one rechargeable battery 310 configured to provide power to one or more components integrated in the medical device controller 300. The rechargeable battery 310 can include a rechargeable multi-cell battery pack. In one example implementation, the rechargeable battery 310 can include three or more 2200 mAh lithium ion cells that provide electrical power to the other device components within the medical device controller 100. For example, the rechargeable battery 310 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 300.

The sensor interface 312 can include physiological signal circuitry that is coupled to one or more sensors configured to monitor one or more physiological parameters of the patient. As shown, the sensors can be coupled to the medical device controller 300 via a wired or wireless connection. The sensors can include one or more ECG sensing electrodes 322, and non-ECG physiological sensors 323 such as vibration sensor 324, tissue fluid monitors 326 (e.g., based on ultra-wide band radiofrequency devices), and motion sensors (e.g., accelerometers, gyroscopes, and/or magnetometers). In some implementations, the sensors can include a plurality of conventional ECG sensing electrodes in addition to digital sensing electrodes.

The sensing electrodes 322 can be configured to monitor a patient's ECG information. For example, by design, the digital sensing electrodes 322 can include skin-contacting electrode surfaces that may be deemed polarizable or non-polarizable depending on a variety of factors including the metals and/or coatings used in constructing the electrode surface. All such electrodes can be used with the principles, techniques, devices, and systems described herein. For example, the electrode surfaces can be based on stainless steel, noble metals such as platinum, or Ag—AgCl.

In some examples, the electrodes 322 can be used with an electrolytic gel dispersed between the electrode surface and the patient's skin. In certain implementations, the electrodes 322 can be dry electrodes that do not need an electrolytic material. As an example, such a dry electrode can be based on tantalum metal and have a tantalum pentoxide coating as is described above. Such dry electrodes can be more comfortable for long term monitoring applications.

Referring back to FIG. 3, the vibration sensors 324 can be configured to detect cardiac or pulmonary vibration information. For example, the vibration sensors 324 can detect a patient's heart valve vibration information. For example, the vibration sensors 324 can be configured to detect cardio-vibrational signal values including any one or all of S1, S2, S3, and S4. From these cardio-vibrational signal values or heart vibration values, certain heart vibration metrics may be calculated, including any one or more of electromechanical activation time (EMAT), average EMAT, percentage of EMAT (% EMAT), systolic dysfunction index (SDI), and left ventricular systolic time (LVST). The vibration sensors 324 can also be configured to detect heart wall motion, for instance, by placement of the sensor in the region of the apical beat. The vibration sensors 324 can include a vibrational sensor configured to detect vibrations from a subject's cardiac and pulmonary system and provide an output signal responsive to the detected vibrations of a targeted organ, for example, being able to detect vibrations generated in the trachea or lungs due to the flow of air during breathing. In certain implementations, additional physiological information can be determined from pulmonary-vibrational signals such as, for example, lung vibration characteristics based on sounds produced within the lungs (e.g., stridor, crackle, etc.). The vibration sensors 324 can also include a multi-channel accelerometer, for example, a three-channel accelerometer configured to sense movement in each of three orthogonal axes such that patient movement/body position can be detected and correlated to detected cardio-vibrations information. The vibration sensors 324 can transmit information descriptive of the cardio-vibrations information to the sensor interface 312 for subsequent analysis.

The tissue fluid monitors 326 can use radio frequency (RF) based techniques to assess fluid levels and accumulation in a patient's body tissue. For example, the tissue fluid monitors 326 can be configured to measure fluid content in the lungs, typically for diagnosis and follow-up of pulmonary edema or lung congestion in heart failure patients. The tissue fluid monitors 326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 326 can transmit information descriptive of the tissue fluid levels to the sensor interface 312 for subsequent analysis.

In certain implementations, the cardiac event detector 316 can be configured to monitor a patient's ECG signal for an occurrence of a cardiac event such as an arrhythmia or other similar cardiac event. The cardiac event detector can be configured to operate in concert with the processor 318 to execute one or more methods that process received ECG signals from, for example, the sensing electrodes 322 and determine the likelihood that a patient is experiencing a cardiac event. The cardiac event detector 316 can be implemented using hardware or a combination of hardware and software. For instance, in some examples, cardiac event detector 316 can be implemented as a software component that is stored within the data storage 304 and executed by the processor 318. In this example, the instructions included in the cardiac event detector 316 can cause the processor 318 to perform one or more methods for analyzing a received ECG signal to determine whether an adverse cardiac event is occurring. In other examples, the cardiac event detector 316 can be an application-specific integrated circuit (ASIC) that is coupled to the processor 318 and configured to monitor ECG signals for adverse cardiac event occurrences. Thus, examples of the cardiac event detector 316 are not limited to a particular hardware or software implementation.

In some implementations, the processor 318 includes one or more processors (or one or more processor cores) that each are configured to perform a series of instructions that result in manipulated data and/or control the operation of the other components of the medical device controller 300. In some implementations, when executing a specific process (e.g., cardiac monitoring), the processor 318 can be configured to make specific logic-based determinations based on input data received and be further configured to provide one or more outputs that can be used to control or otherwise inform subsequent processing to be carried out by the processor 318 and/or other processors or circuitry with which processor 318 is communicatively coupled. Thus, the processor 318 reacts to specific input stimulus in a specific way and generates a corresponding output based on that input stimulus. In some example cases, the processor 318 can proceed through a sequence of logical transitions in which various internal register states and/or other bit cell states internal or external to the processor 318 can be set to logic high or logic low. As referred to herein, the processor 318 can be configured to execute a function where software is stored in a data store coupled to the processor 318, the software being configured to cause the processor 118 to proceed through a sequence of various logic decisions that result in the function being executed. The various components that are described herein as being executable by the processor 318 can be implemented in various forms of specialized hardware, software, or a combination thereof. For example, the processor 318 can be a digital signal processor (DSP) such as a 24-bit DSP. The processor 318 can be a multi-core processor, e.g., having two or more processing cores. The processor 318 can be an Advanced RISC Machine (ARM) processor such as a 32-bit ARM processor or a 64-bit ARM processor. The processor 318 can execute an embedded operating system, and include services provided by the operating system that can be used for file system manipulation, display & audio generation, basic networking, firewalling, data encryption and communications.

As noted above, an ambulatory medical device such as a WCD can be designed to include a digital front-end where analog signals sensed by skin-contacting electrode surfaces of a set of digital sensing electrodes are converted to digital signals for processing. Typical ambulatory medical devices with analog front-end configurations use circuitry to accommodate a signal from a high source impedance from the sensing electrode (e.g., having an internal impedance range from approximately 100 Kiloohms to one or more Megaohms). This high source impedance signal is processed and transmitted to a monitoring device such as processor 318 of the controller 300 as described above for further processing. In certain implementations, the monitoring device, or another similar processor such as a microprocessor or another dedicated processor operably coupled to the sensing electrodes, can be configured to receive a common noise signal from each of the sensing electrodes, sum the common noise signals, invert the summed common noise signals and feed the inverted signal back into the patient as a driven ground using, for example, a driven right leg circuit to cancel out common mode signals.

Figure 15A:
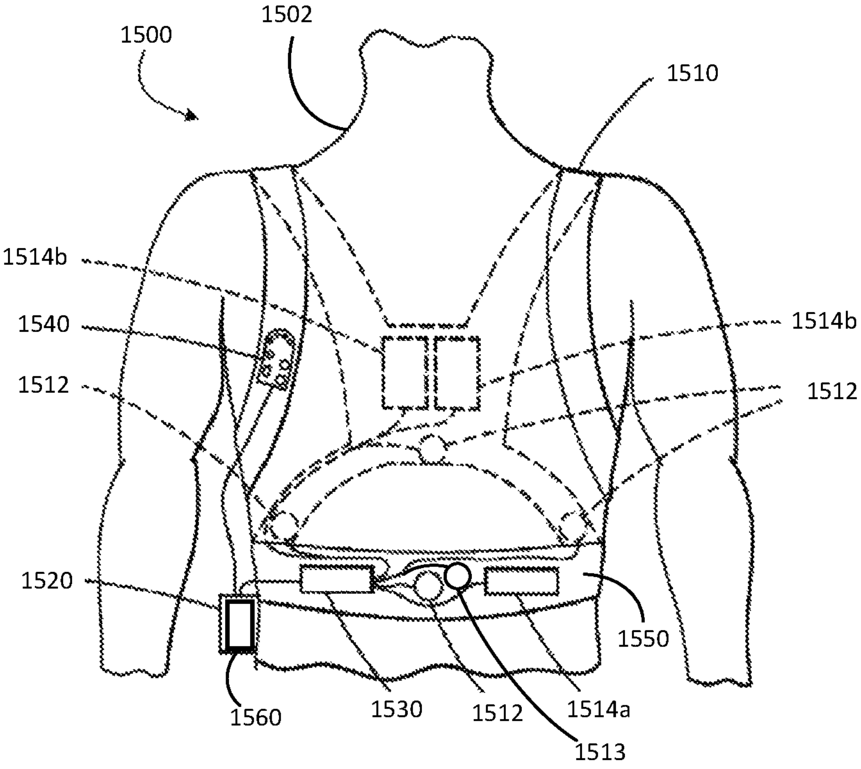
FIGS. 15A-15D illustrate sample ambulatory medical devices that may be prescribed to a heart failure patient, in accordance with an example of the present disclosure.

FIG. 15A illustrates an example medical device 1500 that is external, ambulatory, and wearable by a patient 1502, and configured to implement one or more configurations described herein. For example, the medical device 1500 can be a non-invasive medical device configured to be located substantially external to the patient. Such a medical device 1500 can be, for example, an ambulatory medical device that is capable of and designed for moving with the patient as the patient goes about his or her daily routine. For example, the medical device 1500 as described herein can be bodily-attached to the patient such as the LifeVest® wearable cardioverter defibrillator available from ZOLL® Medical Corporation. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1500 can include one or more of the following: a garment 1510, one or more ECG sensing electrodes 1512, one or more non-ECG physiological sensors 1513, one or more therapy electrodes 1514*a* and 1514*b* (collectively referred to herein as therapy electrodes 1514), a medical device controller 1520 (e.g., controller 300 as described above in the discussion of FIG. 3), a connection pod 1530, a patient interface pod 1540, a belt 1550, or any combination of these. In some examples, at least some of the components of the medical device 1500 can be configured to be affixed to the garment 1510 (or in some examples, permanently integrated into the garment 1510), which can be worn about the patient's torso.

The medical device controller 1520 can be operatively coupled to the sensing electrodes 1512, which can be affixed to the garment 1510, e.g., assembled into the garment 1510 or removably attached to the garment, e.g., using hook and loop fasteners. In some implementations, the sensing electrodes 1512 can be permanently integrated into the garment 1510. The medical device controller 1520 can be operatively coupled to the therapy electrodes 1514. For example, the therapy electrodes 1514 can also be assembled into the garment 1510, or, in some implementations, the therapy electrodes 1514 can be permanently integrated into the garment 1510. In an example, the medical device controller 1520 includes a patient user interface 1560 to allow a patient interface with the externally-worn device. For example, the patient can use the patient user interface 1560 to respond to activity related questions, prompts, and surveys as described herein.

Component configurations other than those shown in FIG. 15A are possible. For example, the sensing electrodes 1512 can be configured to be attached at various positions about the body of the patient 1502. The sensing electrodes 1512 can be operatively coupled to the medical device controller 1520 through the connection pod 1530. In some implementations, the sensing electrodes 1512 can be adhesively attached to the patient 1502. In some implementations, the sensing electrodes 1512 and at least one of the therapy electrodes 1514 can be included on a single integrated patch and adhesively applied to the patient's body.

The sensing electrodes 1512 can be configured to detect one or more cardiac signals. Examples of such signals include ECG signals and/or other sensed cardiac physiological signals from the patient. In certain examples, as described herein, the non-ECG physiological sensors 1513 include accelerometers, vibrational sensors, and other measuring devices for recording additional non-ECG physiological parameters. For example, as described above, the such non-ECG physiological sensors are configured to detect other types of patient physiological parameters and acoustic signals, such as tissue fluid levels, cardio-vibrations, lung vibrations, respiration vibrations, patient movement, etc.

In some examples, the therapy electrodes 1514 can also be configured to include sensors configured to detect ECG signals as well as other physiological signals of the patient. The connection pod 1530 can, in some examples, include a signal processor configured to amplify, filter, and digitize these cardiac signals prior to transmitting the cardiac signals to the medical device controller 1520. One or more of the therapy electrodes 1514 can be configured to deliver one or more therapeutic defibrillating shocks to the body of the patient 1502 when the medical device 1500 determines that such treatment is warranted based on the signals detected by the sensing electrodes 1512 and processed by the medical device controller 1520. Example therapy electrodes 1514 can include metal electrodes such as stainless-steel electrodes that include one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1514 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a patient. Alternatively, the optional therapeutic elements can be deactivated (e.g., via a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 15B:
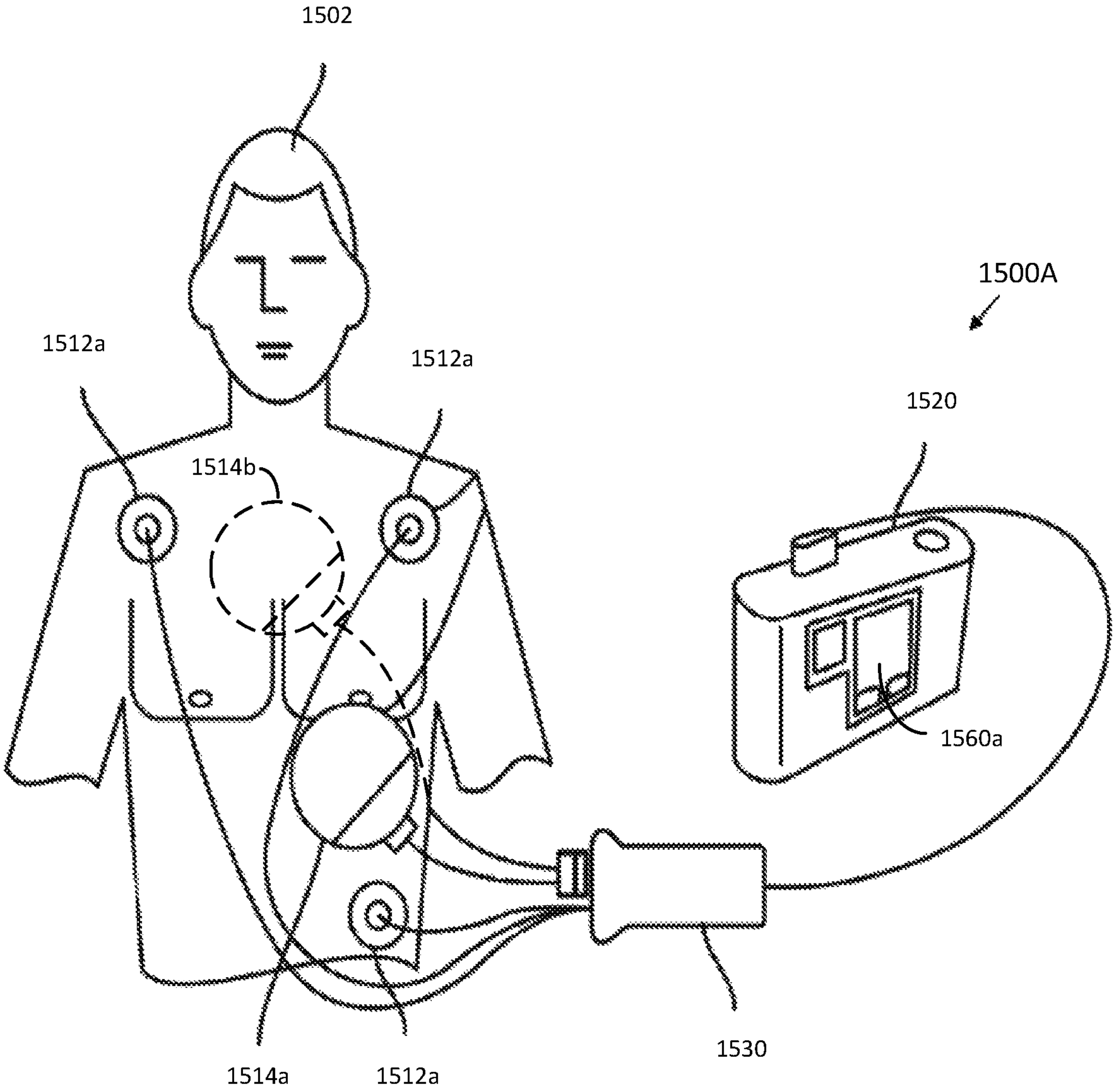

FIG. 15B illustrates a hospital wearable defibrillator 1500A that is external, ambulatory, and wearable by a patient 1502. Hospital wearable defibrillator 1500A can be configured in some implementations to provide pacing therapy, e.g., to treat bradycardia, tachycardia, and asystole conditions. The hospital wearable defibrillator 1500A can include one or more ECG sensing electrodes 1512*a*, one or more therapy electrodes 1514*a* and 1514*b*, a medical device controller 1520 and a connection pod 1530. For example, each of these components can be structured and function as like number components of the medical device 1500. For example, the electrodes 1512*a*, 1514*a*, 1514*b* can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. For example, the front adhesively attachable therapy electrode 1514*a* attaches to the front of the patient's torso to deliver pacing or defibrillating therapy. Similarly, the back adhesively attachable therapy electrode 1514*b* attaches to the back of the patient's torso. In an example scenario, at least three ECG adhesively attachable sensing electrodes 1512*a* can be attached to at least above the patient's chest near the right arm, above the patient's chest near the left arm, and towards the bottom of the patient's chest in a manner prescribed by a trained professional.

A patient being monitored by a hospital wearable defibrillator and/or pacing device may be confined to a hospital bed or room for a significant amount of time (e.g., 75% or more of the patient's stay in the hospital). As a result, a user interface 1560*a* can be configured to interact with a user other than the patient, e.g., a nurse, for device-related functions such as initial device baselining, setting and adjusting patient parameters, and changing the device batteries.

In some implementations, an example of a therapeutic medical device that includes a digital front-end in accordance with the systems and methods described herein can include a short-term defibrillator and/or pacing device. For example, such a short-term device can be prescribed by a physician for patients presenting with syncope. A wearable defibrillator can be configured to monitor patients presenting with syncope by, e.g., analyzing the patient's physiological and cardiac activity for aberrant patterns that can indicate abnormal physiological function. For example, such aberrant patterns can occur prior to, during, or after the onset of syncope. In such an example implementation of the short-term wearable defibrillator, the electrode assembly can be adhesively attached to the patient's skin and have a similar configuration as the hospital wearable defibrillator described above in connection with FIG. 15A.

Figure 15C:
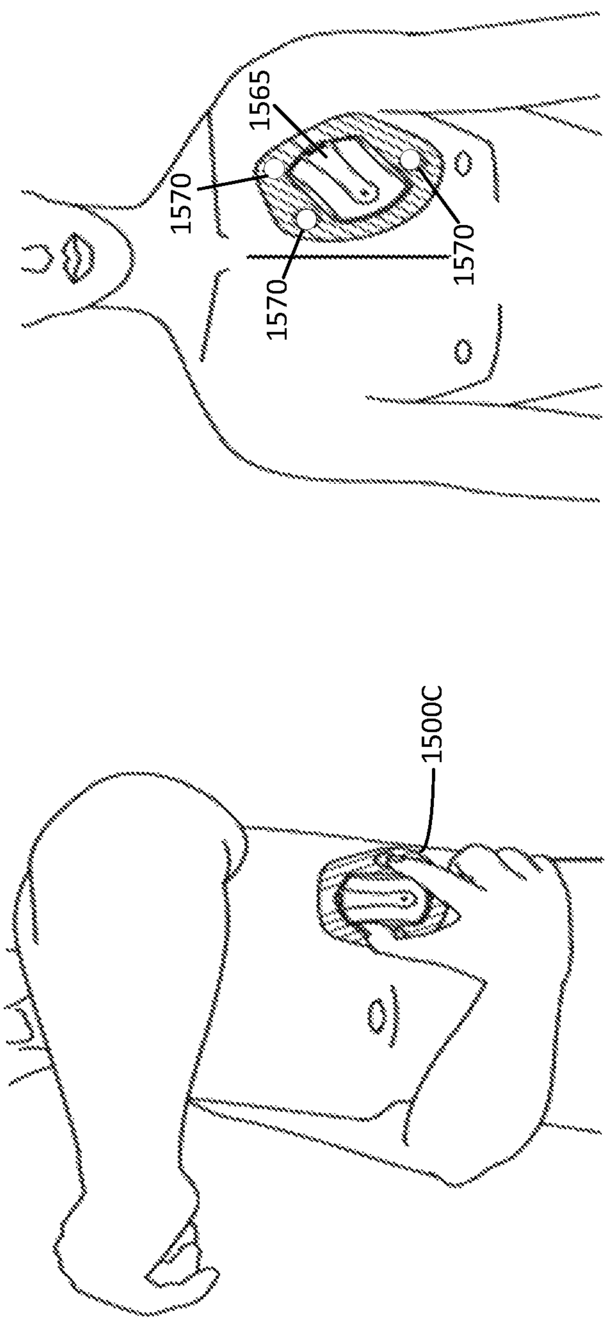
Figure 15D:
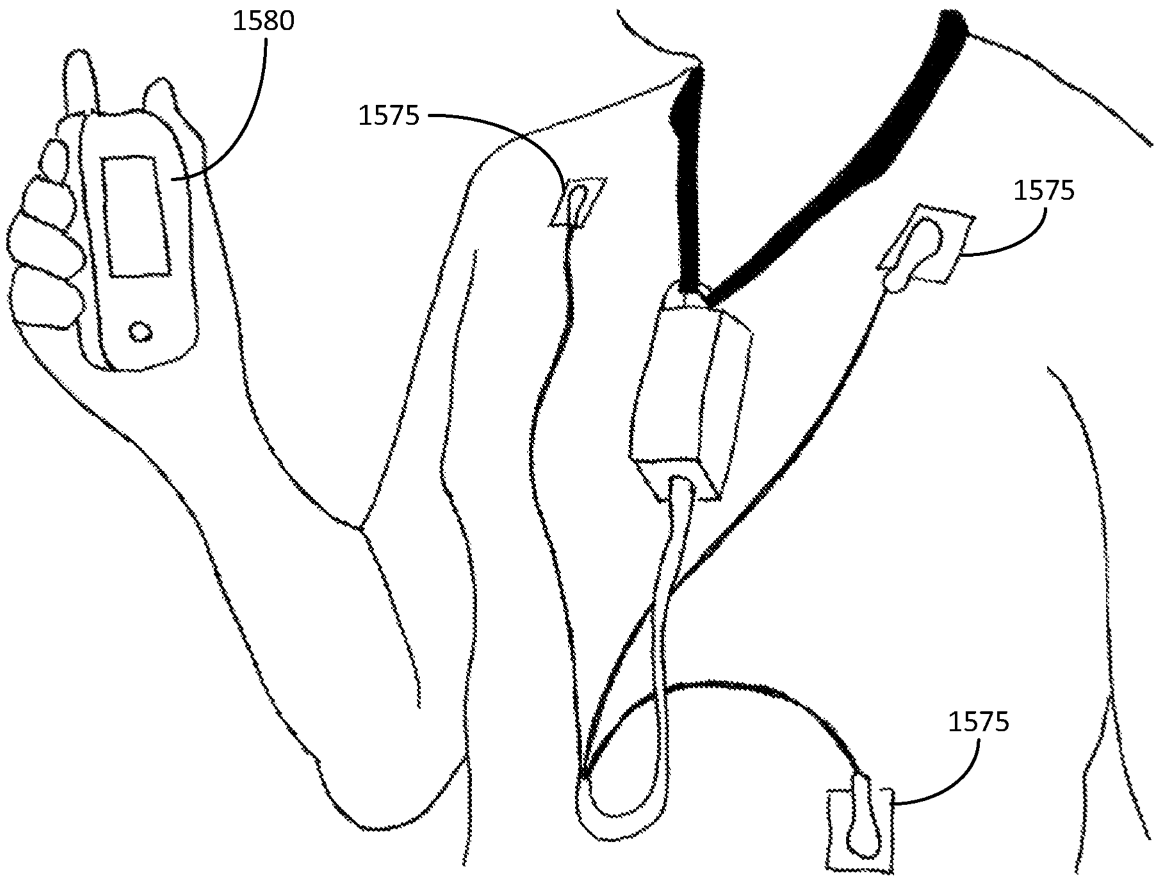

FIGS. 15C and 15D illustrate example wearable patient monitoring devices with no treatment or therapy functions. For example, such devices are configured to monitor one or more physiological parameters of a patient, e.g., for remotely monitoring and/or diagnosing a condition of the patient. For example, such physiological parameters can include a patient's ECG information, tissue (e.g., lung) fluid levels, cardio-vibrations (e.g., using accelerometers or microphones), and other related cardiac information. A cardiac monitoring device is a portable device that the patient can carry around as he or she goes about their daily routine.

Referring to FIG. 15C, an example wearable patient monitoring device 1500C can include tissue fluid monitors 1565 that use radio frequency (RF) based techniques to assess fluid levels and accumulation in a patient's body tissue. Such tissue fluid monitors 1565 can be configured to measure fluid content in the lungs, typically for diagnosis and follow-up of pulmonary edema or lung congestion in heart failure patients. The tissue fluid monitors 1565 can include one or more antennas configured to direct RF waves through a patient's tissue and measure output RF signals in response to the waves that have passed through the tissue. In certain implementations, the output RF signals include parameters indicative of a fluid level in the patient's tissue. In examples, device 1500C may be a cardiac monitoring device that also includes digital sensing electrodes 1570 for sensing ECG activity of the patient. Device 1500C can pre-process the ECG signals via one or more ECG processing and/or conditioning circuits such as an ADC, operational amplifiers, digital filters, and/or signal amplifiers under control of a microprocessor. Device 1500C can transmit information descriptive of the ECG activity and/or tissue fluid levels via a network interface to a remote server for analysis.

Referring to FIG. 15D, another example wearable cardiac monitoring device 1500D can be attached to a patient via at least three adhesive digital cardiac sensing electrodes 1575 disposed about the patient's torso. Cardiac devices 1500C and 1500D are used in cardiac monitoring and telemetry and/or continuous cardiac event monitoring applications, e.g., in patient populations reporting irregular cardiac symptoms and/or conditions. These devices can transmit information descriptive of the ECG activity and/or tissue fluid levels via a network interface to a remote server for analysis. Example cardiac conditions that can be monitored include atrial fibrillation (AF), bradycardia, tachycardia, atrio-ventricular block, Lown-Ganong-Levine syndrome, atrial flutter, sino-atrial node dysfunction, cerebral ischemia, pause (s), and/or heart palpitations. For example, such patients may be prescribed a cardiac monitoring for an extended period of time, e.g., 10 to 30 days, or more. In some ambulatory cardiac monitoring and/or telemetry applications, a portable cardiac monitoring device can be configured to substantially continuously monitor the patient for a cardiac anomaly, and when such an anomaly is detected, the monitor can automatically send data relating to the anomaly to a remote server. The remote server may be located within a 24-hour manned monitoring center, where the data is interpreted by qualified, cardiac-trained reviewers and/or HCPs, and feedback provided to the patient and/or a designated HCP via detailed periodic or event-triggered reports. In certain cardiac event monitoring applications, the cardiac monitoring device is configured to allow the patient to manually press a button on the cardiac monitoring device to report a symptom. For example, a patient can report symptoms such as a skipped beat, shortness of breath, light headedness, racing heart rate, fatigue, fainting, chest discomfort, weakness, dizziness, and/or giddiness. The cardiac monitoring device can record predetermined physiologic parameters of the patient (e.g., ECG information) for a predetermined amount of time (e.g., 1-30 minutes before and 1-30 minutes after a reported symptom). As noted above, the cardiac monitoring device can be configured to monitor physiologic parameters of the patient other than cardiac related parameters. For example, the cardiac monitoring device can be configured to monitor, for example, cardio-vibrational signals (e.g., using accelerometers or microphones), pulmonary-vibrational signals, breath vibrations, sleep related parameters (e.g., snoring, sleep apnea), and tissue fluids, among others.

In some examples, the devices described herein (e.g., FIGS. 15A-15D) can communicate with a remote server via an intermediary or gateway device 1580 such as that shown in FIG. 15D. For instance, devices such as shown in FIGS. 15A-D can be configured to include a network interface communications capability as described herein in reference to, for example, FIG. 3.

Additionally, the devices described herein (e.g., FIGS. 15A-15D) can be configured to include one or more accelerometers as described herein. For example, as noted above in the discussion of FIGS. 1A-1C, one or more accelerometers can be integrated into various components of a wearable device or included as a standalone accelerometer configured to measure movement of a patient.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the scope of the appended claims. For example, it is to be understood that the present disclosure contemplates that, to the extent possible, one or more features of any embodiment can be combined with one or more features of any other embodiment.

Other examples are within the scope of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A wearable medical device for monitoring arrhythmias during different types of patient activities, comprising:

one or more sensing electrodes configured to sense electrical signals that are indicative of cardiac activity of a patient;

one or more accelerometers configured to generate a plurality of motion signals representative of movement of the patient;

at least one memory configured to store an arrhythmia detection process configured to execute in one of an activity-induced noise (AIN) sensitive mode and an AIN robust mode, and a motion classifier trained on motion signals annotated with a plurality of motion classifications; and at least one processor coupled to the at least one memory and configured to:

receive the electrical signals from the one or more sensing electrodes, determine electrocardiogram (ECG) data for the patient based upon the electrical signals, cause the arrhythmia detection process to execute in the AIN sensitive mode, wherein the AIN sensitive mode comprises
analyzing a first plurality of ECG metrics based on the ECG data to detect an arrhythmia,
responsive to detecting the arrhythmia, initiating a process for determining whether treatment is warranted, and
if it is determined that treatment is warranted, initiating the treatment,
analyze motion signals of the one or more accelerometers to determine initiation of a high-noise activity, wherein analyzing comprises
extracting, from the plurality of motion signals, a plurality of features relating to a current state or activity of the patient based on the plurality of motion signals,
applying the motion classifier to a feature vector comprising the plurality of features to generate a respective classification of the plurality of motion classifications, and
storing, to the at least one memory, the respective classification,
cause, in response to determining the initiation of the high-noise activity, the arrhythmia detection process to execute in the AIN robust mode, wherein the AIN robust mode comprises
analyzing a second plurality of ECG metrics based on the ECG data to detect the arrhythmia, wherein the second plurality of ECG metrics comprises a subset of the first plurality of ECG metrics, and
responsive to detecting the arrhythmia,
providing a notification to the patient to stop the high-noise activity, and
causing the arrhythmia detection process to execute in the AIN sensitive mode,
determine a termination of the high-noise activity based on one or more of a predetermined time out condition occurring after a predetermined time period, patient input, or the plurality of motion signals, and
cause, in response to determining the termination of the high-noise activity, the arrhythmia detection process to execute in the AIN sensitive mode.

2. The wearable medical device of claim 1, wherein the at least one processor is configured to, when the predetermined time out condition occurs, prompt the patient to indicate whether the high-noise activity has terminated.

3. The wearable medical device of claim 2, wherein the predetermined time period is a first predetermined time period and the at least one processor is configured to suspend determination of the termination of the high-noise activity for a second predetermined time period if the patient indicates that the high-noise activity has not terminated.

4. The wearable medical device of claim 3, wherein the first or second predetermined time period comprises one or more of thirty seconds, one minute, two minutes, five minutes, ten minutes, fifteen minutes, twenty minutes, or thirty minutes.

5. The wearable medical device of claim 1, wherein the plurality of motion classifications comprises a walking activity and a running activity.

6. The wearable medical device of claim 1, wherein the at least one processor is further configured to:
determine a portion of the ECG data that is noisy ECG data caused by patient activity; and
determine the patient activity is a high-noise activity if the portion of ECG data that is noisy ECG data exceeds a predetermined noise threshold.

7. The wearable medical device of claim 6, wherein the predetermined noise threshold comprises one of:
one or more of a detected ECG noise peak more than 25% greater than a calculated R-wave mean value, a detected noise peak more than 50% greater than a calculated R-wave mean value, or a detected noise peak more than 100% greater than a calculated R-wave mean value; or
a threshold number of ECG noise peaks that are more than 25% greater than a calculated R-wave mean value in a predetermined period of time, wherein the threshold number of ECG noise peaks comprises one or more of 3 peaks, 5 peaks, 10 peaks, or 15 peaks, and the predetermined period of time comprises at least one of 30 seconds, 45 seconds, 60 seconds, 75 seconds, 90 seconds, 3 minutes, 5 minutes, 10 minutes, 15 minutes, or 30 minutes.

8. The wearable medical device of claim 6, wherein: the portion of the ECG data is transformed in a frequency domain; and the predetermined noise threshold comprises a dominant frequency of one or more of less than 1 Hz or in excess of 20 Hz.

9. The wearable medical device of claim 1, wherein to analyze the first plurality of ECG metrics comprises monitoring at least two or more of heart rate, heart rate variability, premature ventricular contraction burden or counts, atrial fibrillation burden, pauses, heart rate turbulence, QRS height, QRS width, changes in ECG morphology, cosine R-T, QT interval, QT variability, T-wave width, T-wave alternans, T-wave amplitude, T-wave variability, R-wave amplitude, and ST segment changes.

10. The wearable medical device of claim 9, wherein to analyze the second plurality of ECG metrics comprises monitoring the patient for at least changes in one or more metrics in the subset of the first plurality of ECG metrics for the patient.

11. The wearable medical device of claim 10, wherein the subset of the first plurality of ECG metrics comprises one or more of heart rate, QRS width, R-wave amplitude, or T-wave amplitude.

12. A wearable cardioverter/defibrillator apparatus for monitoring arrhythmias during different types of patient activities, comprising:
one or more sensing electrodes configured to sense electrical signals that are indicative of cardiac activity of a patient;
one or more accelerometers configured to generate a plurality of motion signals representative of movement of the patient;
at least one memory configured to store
an arrhythmia detection process configured to execute in one of an activity-induced noise (AIN) sensitive mode and an AIN robust mode, and
a motion classifier trained on motion signals annotated with a plurality of motion classifications;
a user interface configured to receive patient input;
one or more accelerometers configured to generate a plurality of motion signals representative of movement of a patient; and
at least one processor coupled to the at least one memory and the one or more accelerometers and configured to:
receive the electrical signals from the one or more sensing electrodes, determine electrocardiogram (ECG) data for the patient based on the electrical signals, cause the arrhythmia detection process to execute in the AIN sensitive mode, wherein the AIN sensitive mode comprises analyzing a first plurality of ECG metrics based on the ECG data to detect an arrhythmia, responsive to detecting the arrhythmia, initiating a process for determining whether treatment is warranted, and if it is determined that treatment is warranted, initiating the treatment, analyze motion signals of the one or more accelerometers to determine initiation of a high-noise activity, wherein analyzing comprises extracting, from the plurality of motion signals, a plurality of features relating to a current state or activity of the patient based on the plurality of motion signals, applying the motion classifier to a feature vector comprising the plurality of features to generate a respective classification of the plurality of motion classifications, and storing, to the at least one memory, the respective classification, cause, in response to determining the initiation of the high-noise activity, the arrhythmia detection process to execute in the AIN robust mode, wherein the AIN robust mode comprises analyzing a second plurality of ECG metrics based on the ECG data to detect the arrhythmia, wherein the second plurality of ECG metrics comprises a subset of the first plurality of ECG metrics, and responsive to detecting the arrhythmia, providing a notification to the patient to stop the high-noise activity, and causing the arrhythmia detection process to execute in the AIN sensitive mode, determine a termination of the high-noise activity based on one or more of a predetermined time out condition occurring after a predetermined time period, the patient input, or the plurality of motion signals, and cause, in response to determining the termination of the high-noise activity, the arrhythmia detection process to execute in the AIN sensitive mode.

13. The wearable cardioverter/defibrillator apparatus of claim 12, wherein the at least one processor is further configured to determine the termination of the high-noise activity based on one or more of a predetermined time out condition occurring after a predetermined time period, the patient input, or the plurality of motion signals.

14. The wearable cardioverter/defibrillator apparatus of claim 13, wherein the at least one processor is configured to, when the predetermined time out condition occurs, prompt the patient to indicate whether the high-noise activity has terminated.

15. The wearable cardioverter/defibrillator apparatus of claim 14, wherein: the predetermined time period is a first predetermined time period; and the at least one processor is configured to suspend determination of the termination of the high-noise activity for a second predetermined time period if the patient indicates that the high-noise activity has not terminated.

16. The wearable cardioverter/defibrillator apparatus of claim 15, wherein: the first predetermined time period comprises one or more of thirty seconds, one minute, two minutes, five minutes, ten minutes, fifteen minutes, twenty minutes, or thirty minutes; and the second predetermined time period comprises one or more of thirty seconds, one minute, two minutes, five minutes, ten minutes, fifteen minutes, twenty minutes, or thirty minutes.

17. The wearable cardioverter/defibrillator apparatus of claim 12, wherein the plurality of motion classifications comprises a walking activity and a running activity.

18. The wearable cardioverter/defibrillator apparatus of claim 12, wherein to determine initiation of the high-noise activity further comprises:

determine a portion of the ECG data that is noisy ECG data caused by patient activity; and determine the patient activity is the high-noise activity if the portion of ECG data that is noisy ECG data exceeds a predetermined noise threshold.

19. The wearable cardioverter/defibrillator apparatus of claim 18, wherein the predetermined noise threshold comprises one or more of a threshold number of detected ECG noise peaks more than 25% greater than a calculated R-wave mean value, a detected noise peak more than 50% greater than a calculated R-wave mean value, or a detected noise peak more than 100% greater than a calculated R-wave mean value, the threshold number of detected ECG noise peaks being one or more of 1 peak, 3 peaks, 5 peaks, 10 peaks, or 15 peaks.

20. The wearable cardioverter/defibrillator apparatus of claim 18, wherein: the portion of the ECG data is transformed in a frequency domain; and the predetermined noise threshold comprises a dominant frequency of one or more of less than 1 Hz or in excess of 20 Hz.

21. The wearable cardioverter/defibrillator apparatus of claim 12, wherein to analyze the first plurality of ECG metrics comprises monitoring at least two or more of heart rate, heart rate variability, premature ventricular contraction burden or counts, atrial fibrillation burden, pauses, heart rate turbulence, QRS height, QRS width, changes in ECG morphology, cosine R-T, QT interval, QT variability, T-wave width, T-wave alternans, T-wave amplitude, T-wave variability, R-wave amplitude, and ST segment changes.

22. The wearable cardioverter/defibrillator apparatus of claim 21, wherein to analyze the second plurality of ECG metrics comprises monitoring the patient for changes in one or more metrics in the subset of the first plurality of ECG metrics.

23. The wearable cardioverter/defibrillator apparatus of claim 22, wherein the subset of the first plurality of ECG metrics comprises one or more of heart rate, QRS width, R-wave amplitude, or T-wave amplitude.

24. The wearable medical device of claim 1, wherein providing the notification to the patient comprises providing at least one of an audible alert, a tactile alert, or a visual alert.

* * * * *